(12) United States Patent
Jang et al.

(10) Patent No.: US 12,256,637 B2
(45) Date of Patent: Mar. 18, 2025

(54) ORGANIC OPTOELECTRONIC DEVICE AND DISPLAY DEVICE

(71) Applicant: SAMSUNG SDI CO., LTD., Yongin-si (KR)

(72) Inventors: Kipo Jang, Suwon-si (KR); Byungku Kim, Suwon-si (KR); Giwook Kang, Suwon-si (KR); Hanill Lee, Suwon-si (KR); Sung-Hyun Jung, Suwon-si (KR); Ho Kuk Jung, Suwon-si (KR); Youngkyoung Jo, Suwon-si (KR); Eun Sun Yu, Suwon-si (KR)

(73) Assignee: SAMSUNG SDI CO., LTD., Yongin-si (KR)

(*) Notice: Subject to any disclaimer, the term of this patent is extended or adjusted under 35 U.S.C. 154(b) by 0 days.

(21) Appl. No.: 18/229,899

(22) Filed: Aug. 3, 2023

(65) Prior Publication Data
US 2023/0389420 A1  Nov. 30, 2023

Related U.S. Application Data

(63) Continuation of application No. 16/629,671, filed as application No. PCT/KR2018/007516 on Jul. 3, 2018, now Pat. No. 11,723,270.

(30) Foreign Application Priority Data

Jul. 21, 2017  (KR) .................. 10-2017-0093029

(51) Int. Cl.
*H10K 85/60* (2023.01)
*C07D 405/14* (2006.01)
(Continued)

(52) U.S. Cl.
CPC ....... *H10K 85/6572* (2023.02); *C07D 405/14* (2013.01); *C07D 487/04* (2013.01);
(Continued)

(58) Field of Classification Search
None
See application file for complete search history.

(56) References Cited

U.S. PATENT DOCUMENTS

2014/0131676 A1   5/2014   Beers et al.
2014/0361269 A1  12/2014   Kim et al.
(Continued)

FOREIGN PATENT DOCUMENTS

CN    105679946 A    6/2016
CN    106661445 A    5/2017
(Continued)

OTHER PUBLICATIONS

International Search Report dated Oct. 5, 2018 for PCT/KR2018/007516.
(Continued)

*Primary Examiner* — Anthony J Frost
(74) *Attorney, Agent, or Firm* — Lee IP Law, P.C.

(57) ABSTRACT

Disclosed are an organic optoelectronic device includes an anode and a cathode facing each other and an organic layer disposed between the anode and the cathode, wherein the organic layer includes at least one of a hole injection layer, a hole transport layer, a light emitting layer, and an electron transport layer, and the light emitting layer includes a first host, a second host, and a phosphorescent dopant represented by Chemical Formula 4, and a display device including the same.

4 Claims, 1 Drawing Sheet

(51) Int. Cl.
| | |
|---|---|
| *C07D 487/04* | (2006.01) |
| *C07F 15/00* | (2006.01) |
| *C09K 11/06* | (2006.01) |
| *H10K 85/30* | (2023.01) |
| *H10K 50/11* | (2023.01) |
| *H10K 71/00* | (2023.01) |
| *H10K 71/16* | (2023.01) |
| *H10K 101/00* | (2023.01) |
| *H10K 101/10* | (2023.01) |
| *H10K 102/00* | (2023.01) |

(52) U.S. Cl.
CPC .......... *C07F 15/0033* (2013.01); *C09K 11/06* (2013.01); *H10K 85/342* (2023.02); *H10K 85/654* (2023.02); *H10K 85/6574* (2023.02); *C09K 2211/1029* (2013.01); *C09K 2211/1033* (2013.01); *C09K 2211/185* (2013.01); *H10K 50/11* (2023.02); *H10K 71/00* (2023.02); *H10K 71/164* (2023.02); *H10K 2101/10* (2023.02); *H10K 2101/90* (2023.02); *H10K 2102/351* (2023.02)

(56) References Cited

U.S. PATENT DOCUMENTS

| | | | |
|---|---|---|---|
| 2015/0171340 A1* | 6/2015 | Lee | H10K 85/6574 544/333 |
| 2015/0280136 A1 | 10/2015 | Ryu et al. | |
| 2016/0049597 A1 | 2/2016 | Ma et al. | |
| 2016/0163995 A1 | 6/2016 | Kang et al. | |
| 2017/0069848 A1* | 3/2017 | Zeng | C07F 15/0033 |

FOREIGN PATENT DOCUMENTS

| | | |
|---|---|---|
| JP | 5338184 B2 | 2/2010 |
| JP | 2011-151212 A | 8/2011 |
| JP | 2014-094941 A | 5/2014 |
| JP | 2016-147849 A | 8/2016 |
| JP | 2017-501127 A | 1/2017 |
| JP | 2017-503338 A | 1/2017 |
| KR | 10-2003-0038441 A | 5/2003 |
| KR | 10-2014-0083897 A | 7/2014 |
| KR | 2014-0087883 A | 7/2014 |
| KR | 10-2014-0144550 A | 12/2014 |
| KR | 10-2015-0042335 A | 4/2015 |
| KR | 10-2015-0070860 A | 6/2015 |
| KR | 10-2015-0135123 A | 12/2015 |
| KR | 10-2016-0046078 A | 4/2016 |
| KR | 10-2016-0064955 A | 6/2016 |
| KR | 10-2016-0107975 A | 9/2016 |
| KR | 10-2017-0041886 A | 4/2017 |
| KR | 10-2017-0065711 A | 6/2017 |
| TW | 201533038 A | 1/2015 |
| WO | WO 2012/070233 A1 | 5/2012 |
| WO | WO 2013/077362 A1 | 5/2013 |
| WO | WO 2015/084021 A1 | 6/2015 |
| WO | WO 2016/027938 A | 2/2016 |
| WO | WO 2016/148390 A1 | 9/2016 |

OTHER PUBLICATIONS

European Search Report dated Mar. 17, 2021.
Notice of Allowance with search report dated Jun. 21, 2023, from corresponding Chinese Application No. 201880044496.9.

* cited by examiner

[FIG. 1]
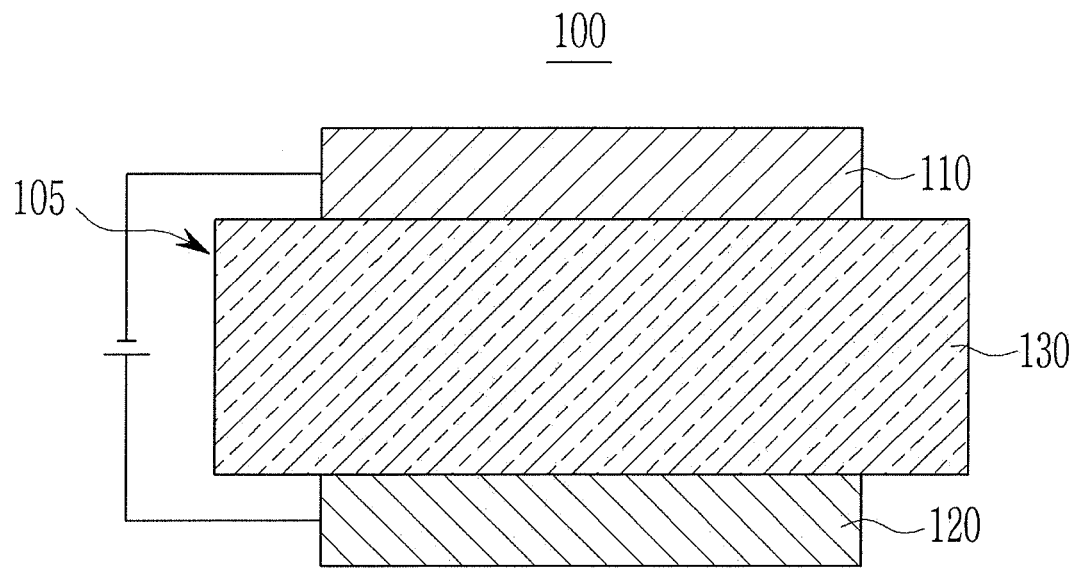
[FIG. 2]
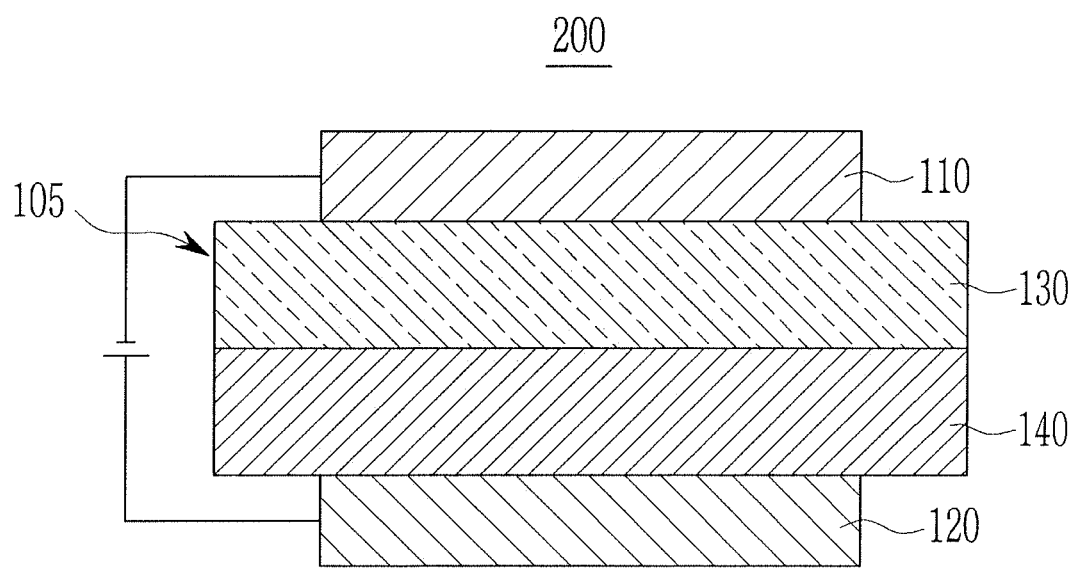

ORGANIC OPTOELECTRONIC DEVICE AND DISPLAY DEVICE

CROSS REFERENCE TO RELATED APPLICATIONS

This is a continuation application based on pending application Ser. No. 16/629,671, filed Jan. 9, 2020, the entire contents of which is hereby incorporated by reference.

application Ser. No. 16/629,671 is the U.S. national phase application based on PCT/KR2018/007516, filed Jul. 3, 2018, which is based on Korean Patent Application No. 10-2017-0093029 filed Jul. 21, 2017, the entire contents of both being hereby incorporated by reference.

FIELD OF THE INVENTION

An organic optoelectronic device and a display device are disclosed.

DESCRIPTION OF THE RELATED ART

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DESCRIPTION OF THE INVENTION

Technical Problem

An embodiment provides an organic optoelectronic device having high efficiency and long life-span.

Another embodiment provides a display device including the organic optoelectronic device.

Technical Solution

According to an embodiment, an organic optoelectronic device includes an anode and a cathode facing each other and an organic layer disposed between the anode and the cathode, wherein the organic layer includes at least one of a hole injection layer, a hole transport layer, a light emitting layer, and an electron transport layer, and the light emitting layer includes a first host represented by Chemical Formula 1, a second host represented by a combination of Chemical Formula 2 and Chemical Formula 3, and a phosphorescent dopant represented by Chemical Formula 4.

[Chemical Formula 1]

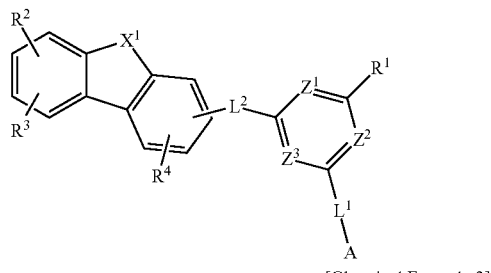

[Chemical Formula 2]

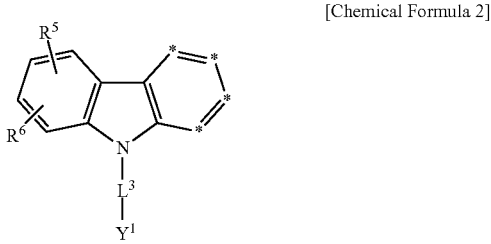

[Chemical Formula 3]

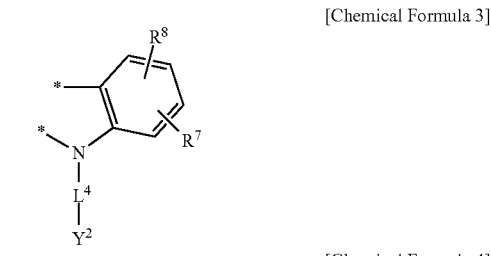

[Chemical Formula 4]

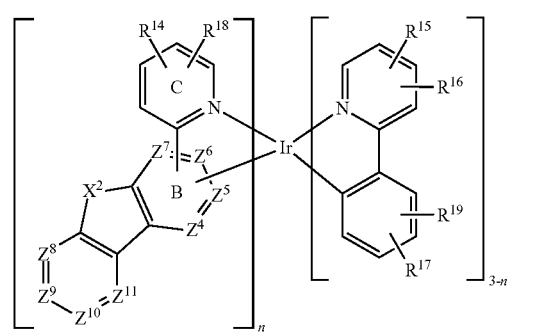

In Chemical Formula 1,
$X^1$ is O or S,
$Z^1$ to $Z^3$ are independently N or $CR^a$,
at least two of $Z^1$ to $Z^3$ are N,
$L^1$ and $L^2$ are independently a single bond, or a substituted or unsubstituted C6 to C20 arylene group, A is a substituted or unsubstituted carbazolyl group, $R^1$ is a substituted or unsubstituted C6 to C20 aryl group, a substituted or unsubstituted dibenzofuranyl group, or a substituted or unsubstituted dibenzothiophenyl group, and $R^a$ and $R^2$ to $R^4$ are independently hydrogen, deuterium, a cyano group, a substituted or unsubstituted C1 to C10 alkyl group, or a substituted or unsubstituted C6 to C20 aryl group; wherein, in Chemical Formula 2 and Chemical Formula 3, $Y^1$ and $Y^2$ are independently a substituted or unsubstituted C6 to C20 aryl group, or a substituted or unsubstituted C2 to C30 heterocyclic group, adjacent two *'s of Chemical Formula 2 are linked with Chemical Formula 3,

* of Chemical Formula 2 that are not linked with Chemical Formula 3 are independently C-$L^a$-$R^b$, $L^a$, $L^3$, and $L^4$ are independently a single bond, or a substituted or unsubstituted C6 to C20 arylene group, $R^b$ and $R^5$ to $R^8$ are independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group;

wherein in Chemical Formula 4, $Z^4$ to $Z^{11}$ are independently N, C or $CR^c$, the ring C is bound to the ring B through a C—C bond, iridium is bound to the ring B through a Ir—C bond, $X^2$ is O or S, $R^c$ and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is an integer ranging from 1 to 3.

According to another embodiment, a display device including the organic optoelectronic device is provided.

Advantageous Effect

An organic optoelectronic device having high efficiency and a long life-span may be realized.

BRIEF DESCRIPTION OF THE DRAWINGS

FIGS. 1 and 2 are cross-sectional views showing organic light emitting diodes according to embodiments.

DETAILED DESCRIPTION

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a C1 to C10 alkyl group, a C6 to C20 aryl group, or a C2 to C20 heterocyclic group. In addition, in specific examples of the present invention, "substituted" refers to replacement of at least one hydrogen of a substituent or a compound by deuterium, a C1 to C4 alkyl group, a C6 to C12 aryl group, or a C2 to C12 heterocyclic group. More specifically, "substituted" refers to replacement of at least one hydrogen of a substituent or a compound by deuterium, a C1 to C5 alkyl group, a phenyl group, a biphenyl group, a terphenyl group, a naphthyl group, a benzofuranyl group, a benzothiophenyl group, a dibenzofuranyl group, a dibenzothiophenyl group, or a carbazolyl group. In addition, in most specific examples of the present invention, "substituted" refers to replacement of at least one hydrogen of a substituent or a compound by deuterium, a methyl group, an ethyl group, a propanyl group, a butyl group, a phenyl group, a para-biphenyl group, a meta-biphenyl group, a dibenzofuranyl group, a dibenzothiophenyl group, or a carbazolyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic, or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may include a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinoxalinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or combination thereof, but are not limited thereto.

In the present specification, hole characteristics refer to an ability to donate an electron to form a hole when an electric field is applied and that a hole formed in the anode may be easily injected into the light emitting layer, a hole formed in the light emitting layer may be easily transported into the anode, and a hole may be easily transported in the light emitting layer due to conductive characteristics according to a highest occupied molecular orbital (HOMO) level.

In addition, electron characteristics refer to an ability to accept an electron when an electric field is applied and that an electron formed in the cathode may be easily injected into the light emitting layer, an electron formed in the light emitting layer may be easily transported into the cathode, and an electron may be easily transported in the light emitting layer due to conductive characteristics according to a lowest unoccupied molecular orbital (LUMO) level.

Hereinafter, an organic optoelectronic device according to an embodiment is described.

The organic optoelectronic device may be any device to convert electrical energy into photoenergy and vice versa without particular limitation, and may be for example an organic photoelectric device, an organic light emitting diode, an organic solar cell, and an organic photo conductor drum, and the like.

Herein, an organic light emitting diode as one example of an organic optoelectronic device is described referring to drawings.

FIGS. 1 and 2 are cross-sectional view showing organic light emitting diodes according to embodiments.

Referring to FIG. 1, an organic light emitting diode 100 according to an embodiment includes an anode 120 and a cathode 110 facing each other and an organic layer 105 interposed between the anode 120 and cathode 110.

The anode 120 may be made of a conductor having a large work function to help hole injection, and may be for example metal, metal oxide and/or a conductive polymer. The anode 120 may be, for example a metal such as nickel, platinum, vanadium, chromium, copper, zinc, gold and the like or an alloy thereof, metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al and $BaF_2$/Ca, but is not limited thereto.

The organic layer 105 includes a light emitting layer 130.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

An organic optoelectronic device according to an embodiment includes an anode and a cathode facing each other, and an organic layer disposed between the anode and the cathode, wherein the organic layer includes at least one of a hole injection layer, a hole transport layer, a light emitting layer, and an electron transport layer and the light emitting layer includes a first host represented by Chemical Formula 1, a second host represented by a combination of Chemical Formula 2 and Chemical Formula 3, and a phosphorescent dopant represented by Chemical Formula 4.

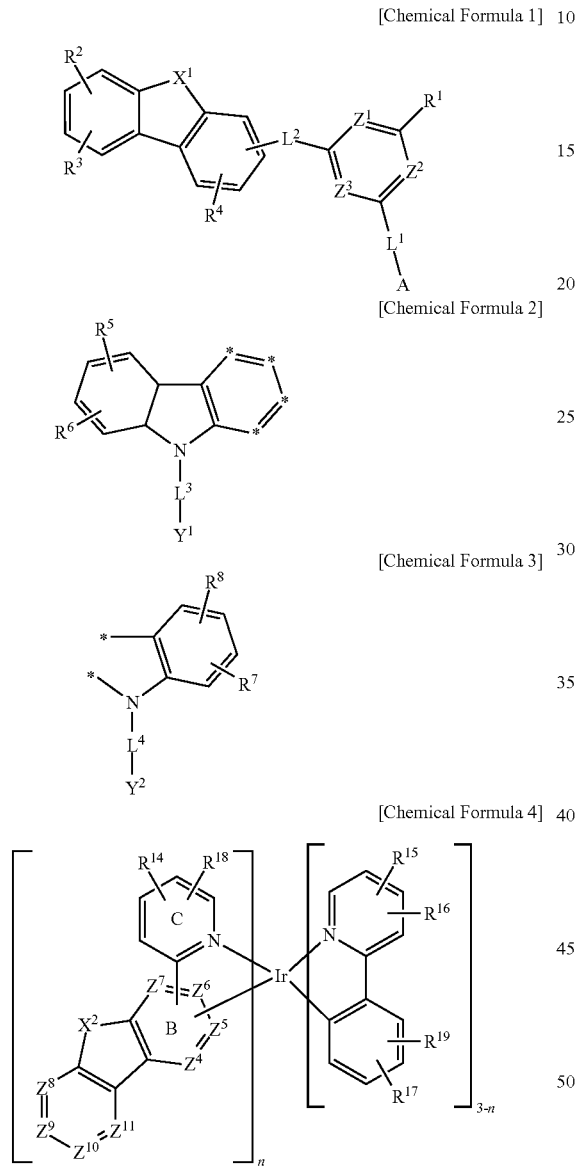

[Chemical Formula 1]

[Chemical Formula 2]

[Chemical Formula 3]

[Chemical Formula 4]

In Chemical Formula 1, $X^1$ is O or S, $Z^1$ to $Z^3$ are independently N or $CR^a$, at least two of $Z^1$ to $Z^3$ are N, $L^1$ and $L^2$ are independently a single bond, or a substituted or unsubstituted C6 to C20 arylene group, A is a substituted or unsubstituted carbazolyl group, $R^1$ is a substituted or unsubstituted C6 to C20 aryl group, a substituted or unsubstituted dibenzofuranyl group, or a substituted or unsubstituted dibenzothiophenyl group, and $R^a$ and $R^2$ to $R^4$ are independently hydrogen, deuterium, a cyano group, a substituted or unsubstituted C1 to C10 alkyl group, or a substituted or unsubstituted C6 to C20 aryl group;

wherein, in Chemical Formula 2 and Chemical Formula 3, $Y^1$ and $Y^2$ are independently a substituted or unsubstituted C6 to C20 aryl group, or a substituted or unsubstituted C2 to C30 heterocyclic group, adjacent two *'s of Chemical Formula 2 are linked with Chemical Formula 3,

* of Chemical Formula 2 that are not linked with Chemical Formula 3 are independently $C-L^a-R^b$, $L^a$, $L^3$, and $L^4$ are independently a single bond, or a substituted or unsubstituted C6 to C20 arylene group, and $R^b$ and $R^5$ to $R^8$ are independently hydrogen, deuterium, a cyano group, a substituted or unsubstituted C1 to C10 alkyl group, a substituted or unsubstituted C6 to C20 aryl group, or a substituted or unsubstituted C2 to C30 heterocyclic group;

wherein, in Chemical Formula 4, $Z^4$ to $Z^{11}$ are independently N, C or $CR^c$, the ring C is bound to the ring B through a C—C bond, iridium is bound to the ring B through a Ir—C bond, $X^2$ is O or S, $R^c$ and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is an integer ranging from 1 to 3.

The organic optoelectronic device according to the present invention increases material stability by introducing a triazine or pyrimidine moiety linked with dibenzofuran (or dibenzothiophene) and simultaneously introducing a carbazole moiety to obtain additional stability due to bipolar characteristics as the first host. A glass transition temperature relative to a molecular weight due to the carbazole moiety may be improved and thus heat resistance may be ensured.

Particularly, indolocarbazole is combined as the second host and thereby holes and electrons are balanced to realize long life-span, low driving voltage characteristics.

Simultaneously, a phosphorescent dopant including a dibenzofuranyl group, a dibenzothiophenyl group, or an N-containing analogous group thereof is additionally combined and thereby combination matching such as packing of host and dopant materials, energy transfer, and the like may be ensured.

The first host represented by Chemical Formula 1 may be for example represented by one of Chemical Formula 1-1 to Chemical Formula 1-4 according to a specific linking position of dibenzofuran (or dibenzothiophene) with the nitrogen-containing hexagonal ring through $L^2$.

[Chemical Formula 1-1]

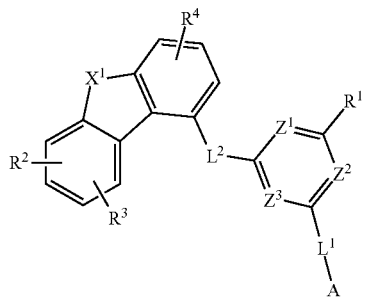

[Chemical Formula 1-2]

[Chemical Formula 1-3]

[Chemical Formula 1-4]

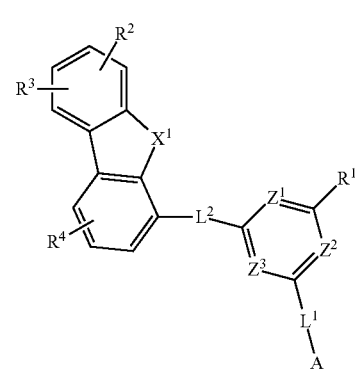

In Chemical Formula 1-1 to Chemical Formula 1-4, $X^1$, $Z^1$ to $Z^3$, $L^1$, $L^2$, A, and $R^1$ to $R^4$ are the same as described above.

In an example embodiment of the present invention, the first host may be represented by Chemical Formula 1-3 or Chemical Formula 1-4, preferably Chemical Formula 1-3, and more preferably Chemical Formula 1-3a wherein dibenzofuran (or dibenzothiophene) is directly linked with the nitrogen-containing hexagonal ring.

[Chemical Formula 1-3a]

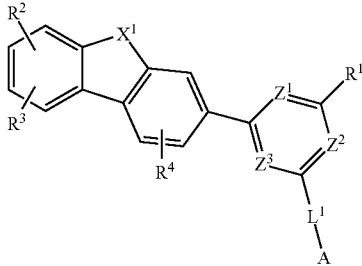

In Chemical Formula 1-3a, $X^1$, $Z^1$ to $Z^3$, $L^1$, A, and $R^1$ to $R^4$ are the same as described above.

The first host increases a hole and electron injection rate through a LUMO expansion and a planarity expansion of an ET moiety such as triazine, pyrimidine, and the like by including a structure where 3-dibenzofuran (or 3-dibenzothiophene) is directly linked with the triazine or pyrimidine moiety as shown in Chemical Formula 1-3a and secures additional stability and improves a glass transition temperature relative to a molecular weight and thus secures heat resistance by introducing a carbazole moiety to apply bipolar characteristics.

In addition, indolocarbazole as a second host may be combined with the first host material to balance the first host material having fast and stable electron transport characteristics and the second host material having fast and stable hole transport characteristics and thus to secure a low driving/long life-span host set having a high glass transition temperature relative to a molecular weight.

Simultaneously, the host set may be combined with a phosphorescent dopant to secure a combination/matching advantage of packing of the host and dopant materials, an energy transport, and the like and thereby obtain characteristics of a low driving, a long life-span, and high efficiency.

In an example embodiment of the present invention, the substituent A is a substituted or unsubstituted carbazolyl group, and may be represented by one of Chemical Formula A-1 to Chemical Formula A-5 according to specifice substitution points.

[Chemical Formula A-1]

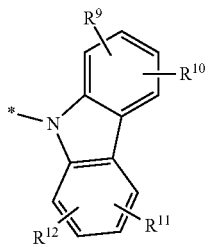

[Chemical Formula A-2]

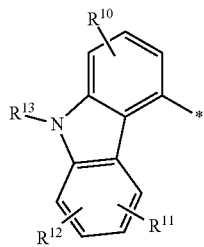

[Chemical Formula A-3]

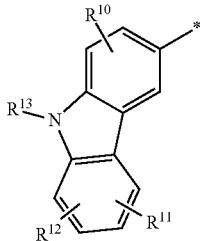

[Chemical Formula A-4]

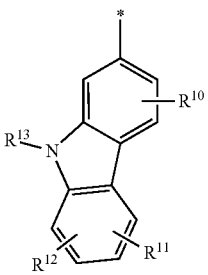

[Chemical Formula A-5]

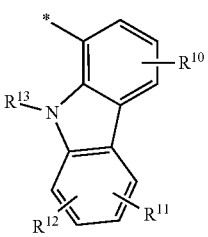

In Chemical Formula A-1 to Chemical Formula A-5, $R^9$ to $R^{13}$ are independently hydrogen, deuterium, a cyano group, a substituted or unsubstituted C1 to C10 alkyl group, or a substituted or unsubstituted C6 to C20 aryl group, and * is a linking point with $L^1$.

In a specific example embodiment, $R^9$ to $R^{13}$ may independently be hydrogen, or a substituted or unsubstituted C6 to C20 aryl group, and more specifically $R^9$ to $R^{13}$ may independently be hydrogen or a phenyl group, for example when A is represented by Chemical Formula A-1, $R^9$ to $R^{12}$ may be all hydrogen or one or two of $R^9$ to $R^{12}$ may be a phenyl group.

In addition, when A is represented by one of Chemical Formula A-2 to Chemical Formula A-5, $R^{13}$ may be a phenyl group and $R^{10}$ to $R^{12}$ are all hydrogen or at least one of $R^{11}$ and $R^{12}$ may be a phenyl group.

Particularly, Chemical Formula 1-3a may be for example represented by one of Chemical Formula 1-3a-I, Chemical Formula 1-3a-II, Chemical Formula 1-3a-III, Chemical Formula 1-3a-IV, and Chemical Formula 1-3a-V, and preferably Chemical Formula 1-3a-I, Chemical Formula 1-3a-II, Chemical Formula 1-3a-III, and Chemical Formula 1-3a-IV according to specific structure of the substituent A.

[Chemical Formula 1-3a-I]

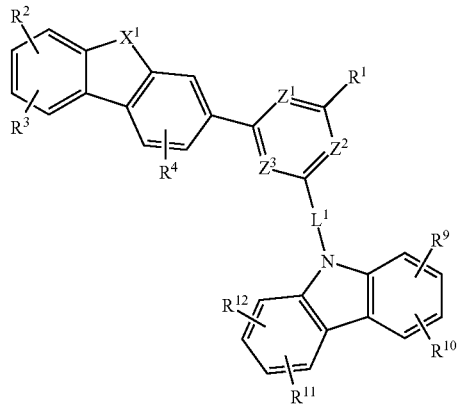

[Chemical Formula 1-3a-II]

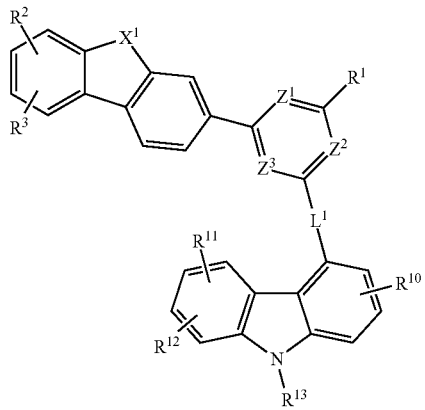

[Chemical Formula 1-3a-III]

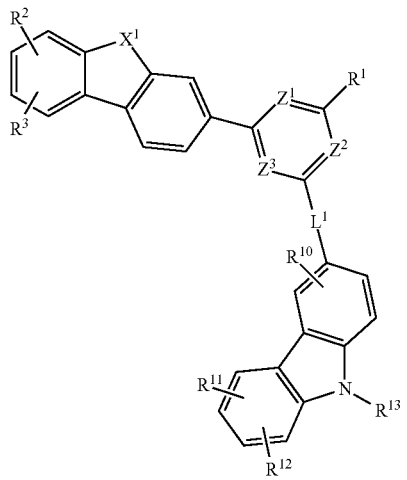

[Chemical Formula 1-3a-IV]

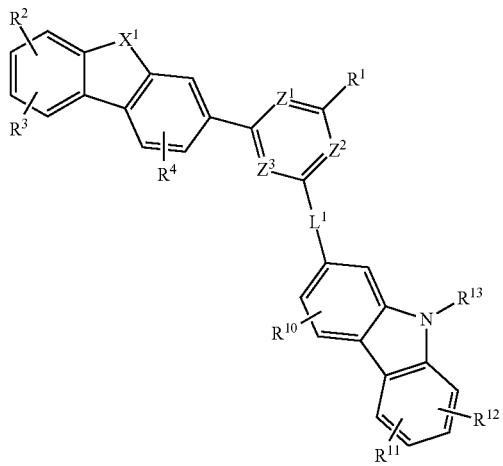

[Chemical Formula 1-3a-V]

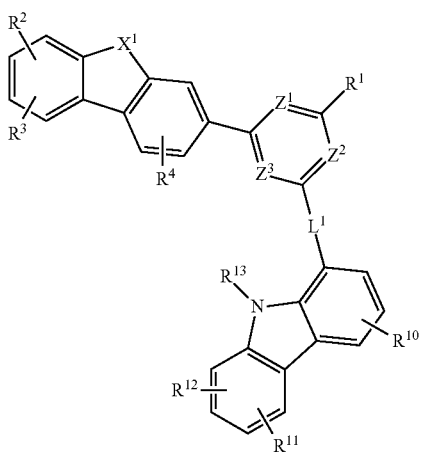

In Chemical Formula 1-3a-I, Chemical Formula 1-3a-II, Chemical Formula 1-3a-III, Chemical Formula 1-3a-IV and Chemical Formula 1-3a-V, $X^1$, $Z^1$ to $Z^3$, $L^1$, $R^1$ to $R^4$ and $R^9$ to $R^{13}$ are the same as described above.

On the other hand, in an example embodiment of the present invention, the hexagonal ring consisting of $Z^1$ to $Z^3$ may be pyrimidine or triazine, in a specific example embodiment, pyrimidine where $Z^1$ and $Z^2$ are N, pyrimidine where $Z^1$ and $Z^3$ are N, pyrimidine where $Z^2$ and $Z^3$ are N, or triazine where $Z^1$ to $Z^3$ are N, and preferably triazine where $Z^1$ to $Z^3$ are N.

In an example embodiment of the present invention, $R^1$ may be a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group, and more specifically $R^1$ may be a substituted or unsubstituted phenyl group, a substituted or unsubstituted dibenzofuranyl group, or a substituted or unsubstituted dibenzothiophenyl group, and may be for example selected from substituents of Group I.

[Group 1]

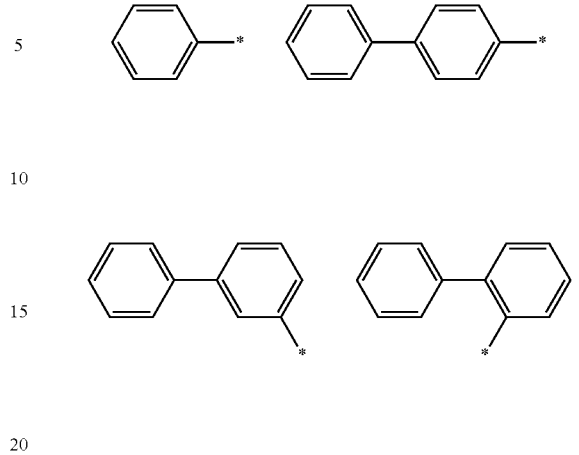

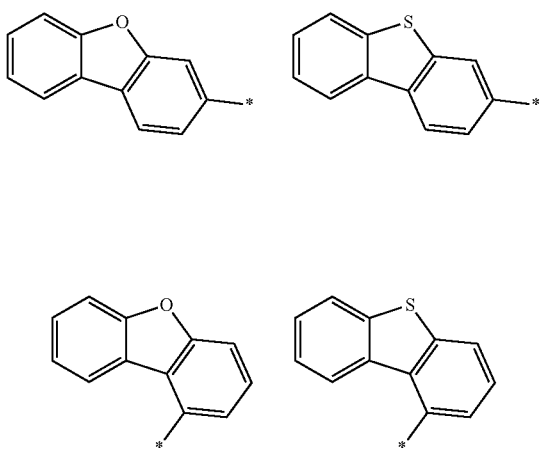

In Group I, * is a linking point with a nitrogen-containing hexagonal ring.

$R^1$ may be preferably a phenyl group, a dibenzofuranyl group, or a dibenzothiophenyl group.

In an example embodiment of the present invention, $R^a$ and $R^2$ to $R^4$ may independently be hydrogen, deuterium, a cyano group, or a substituted or unsubstituted C6 to C12 aryl group, more specifically $R^a$ and $R^2$ to $R^4$ may independently be hydrogen, deuterium, or a cyano group, and preferably $R^a$ and $R^2$ to $R^4$ may be all hydrogen.

In addition, in an example embodiment of the present invention, $L^1$ and $L^2$ may independently be a single bond, or a substituted or unsubstituted C6 to C12 arylene group, and more specifically $L^1$ and $L^2$ may independently be a single bond, a meta-phenylene group, or a para-phenylene group.

In addition, in an example embodiment of the present invention, $R^9$ to $R^{11}$ may independently be hydrogen, deuterium, a cyano group, or a substituted or unsubstituted C6 to C12 aryl group, more specifically $R^9$ to $R^{11}$ may independently be hydrogen, deuterium, a cyano group or a phenyl group, and preferably $R^9$ to $R^{11}$ are all hydrogen or at least one of $R^9$ to $R^{11}$ may be a phenyl group. More preferably, $R^9$ to $R^{11}$ may be all hydrogen or one of $R^9$ to $R^{11}$ may be a phenyl group.

The first host may be for example selected from compounds of Group 1, but is not limited thereto.
[Group 1]
[B-1]
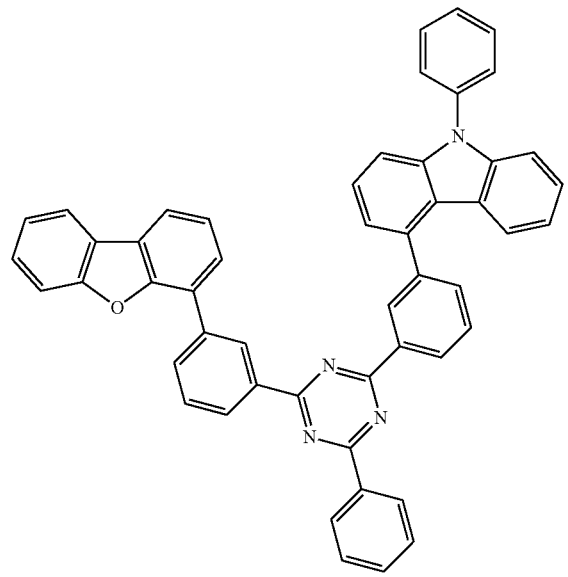
[B-2]
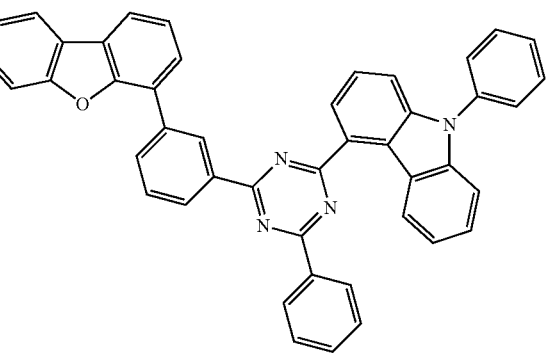
[B-3]
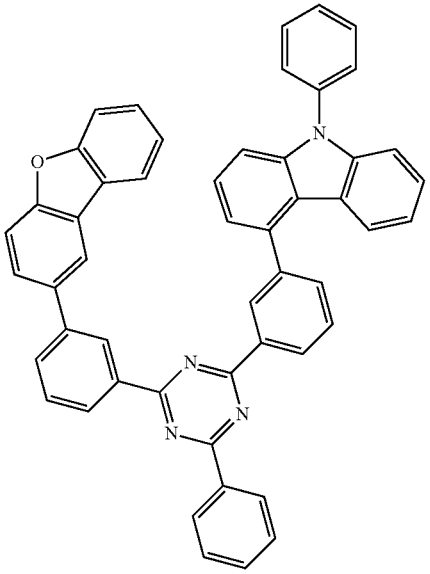
[B-4]
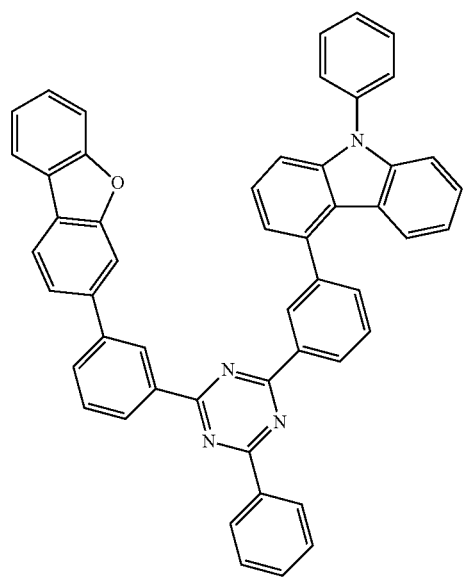
[B-5]

[B-6]
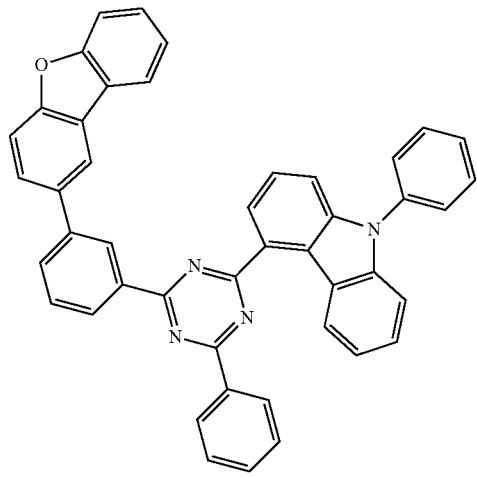
[B-7]
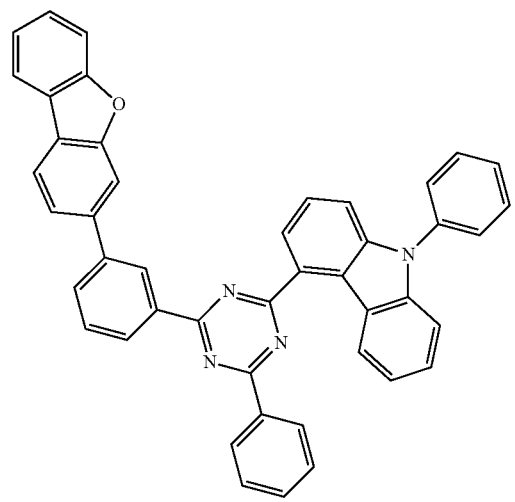
[B-8]
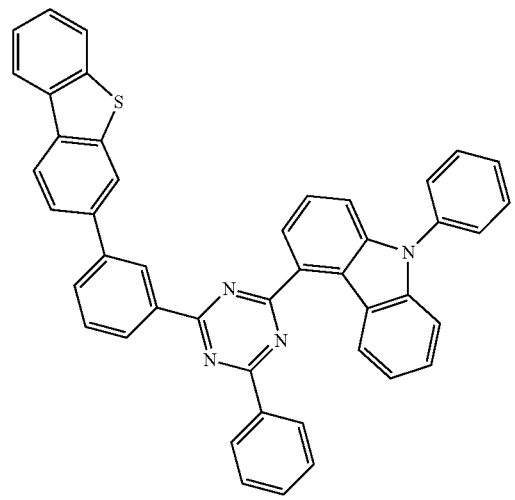
[B-9]
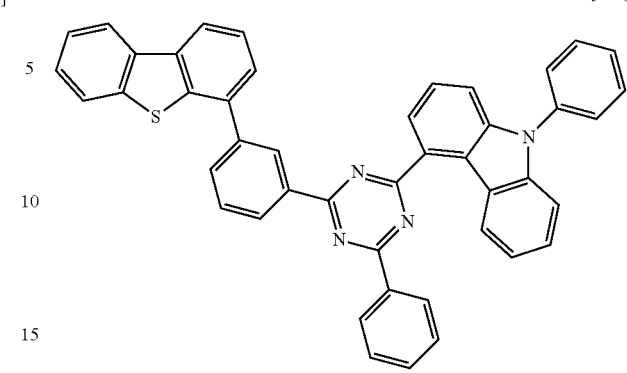
[B-10]
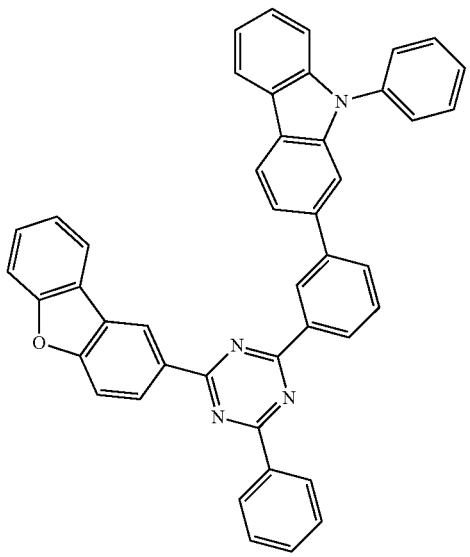
[B-11]
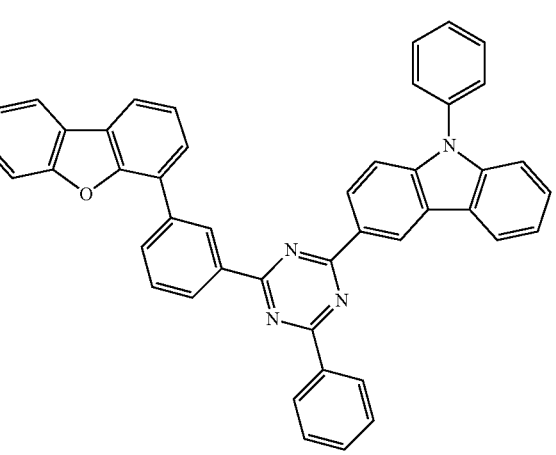

[B-12] 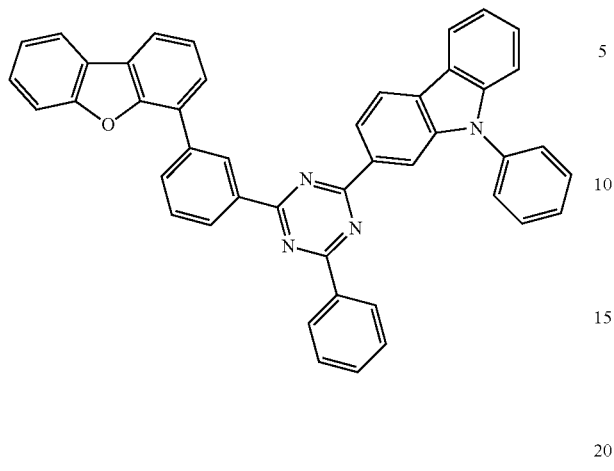
[B-13] 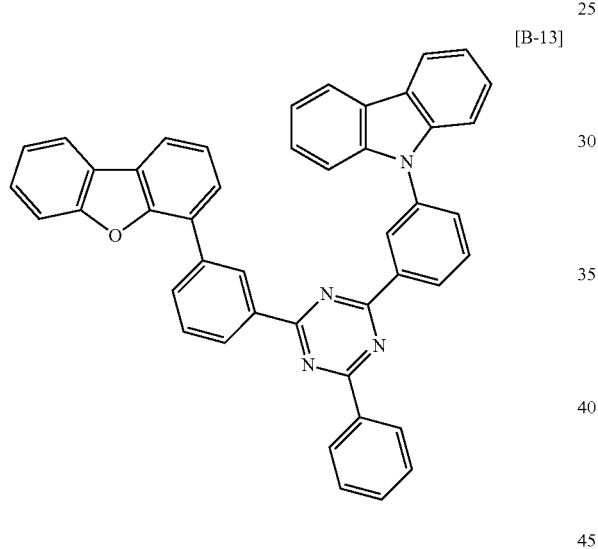
[B-14] 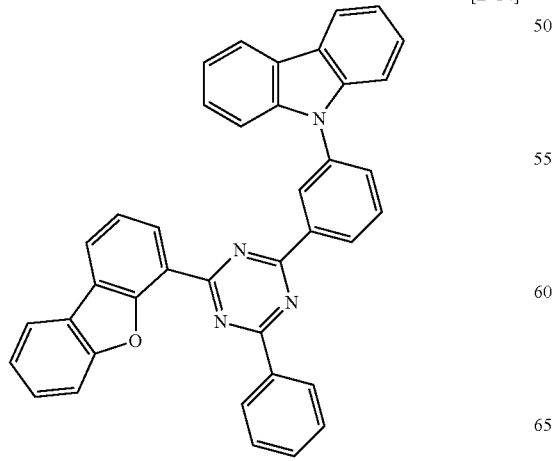
[B-15] 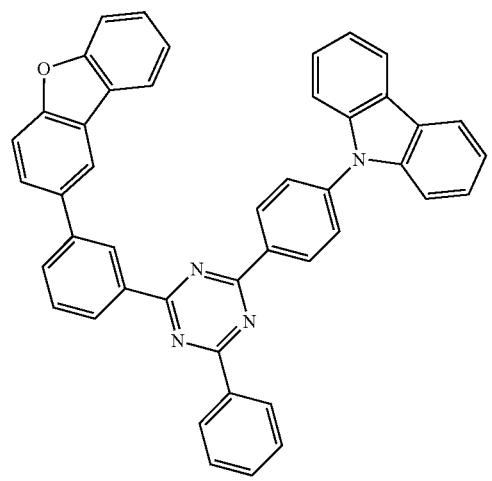
[B-16] 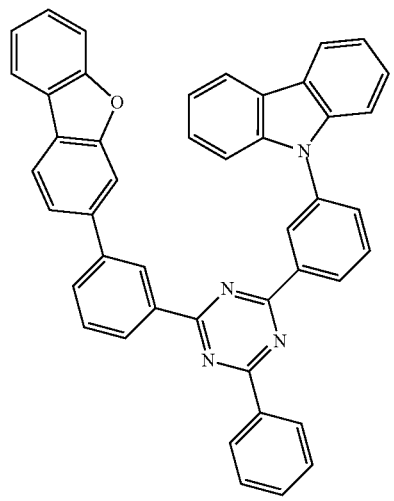
[B-17] 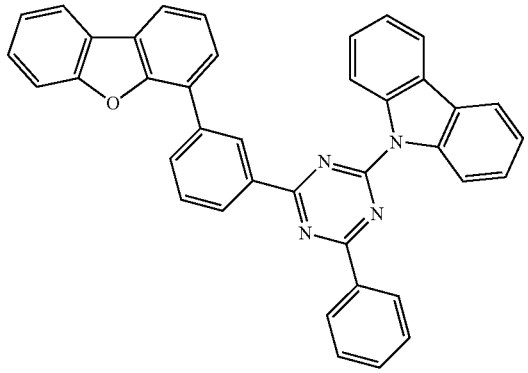

[B-18]
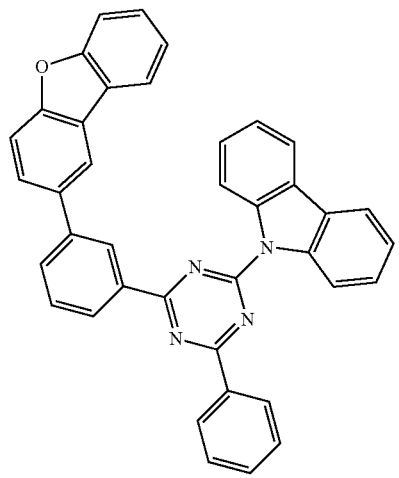
[B-21]
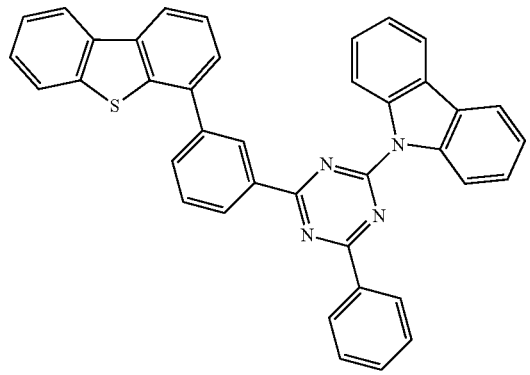
[B-19]
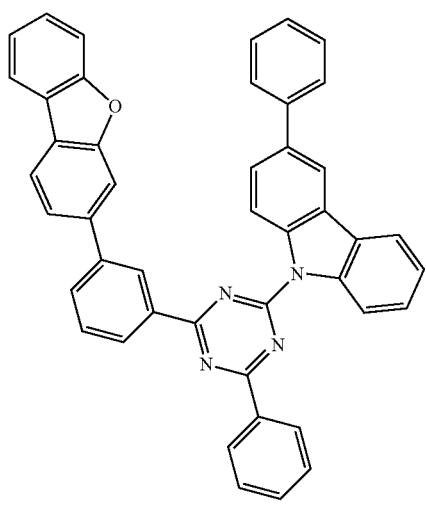
[B-22]
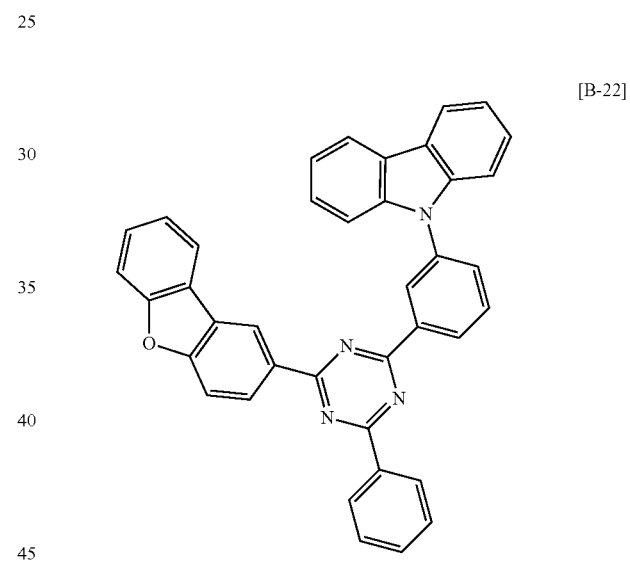
[B-20]
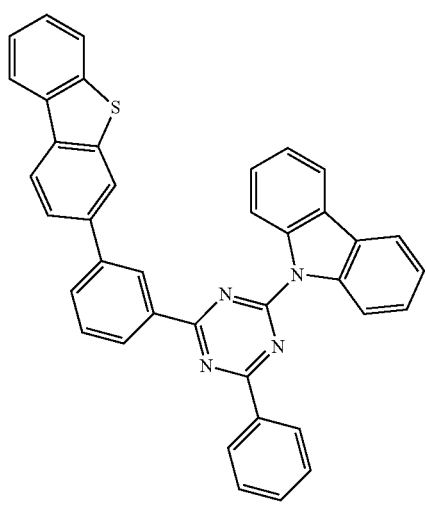
[B-23]
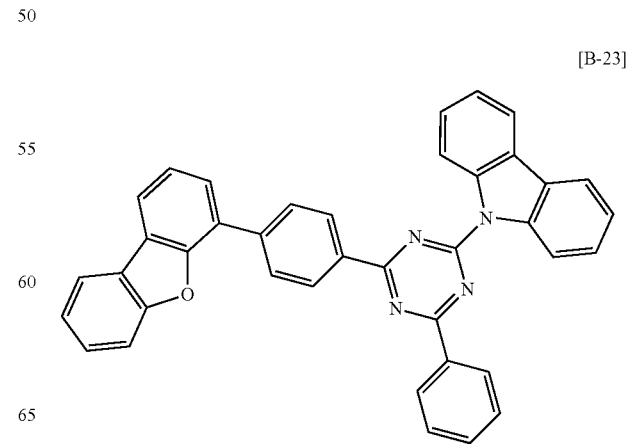

[B-24]
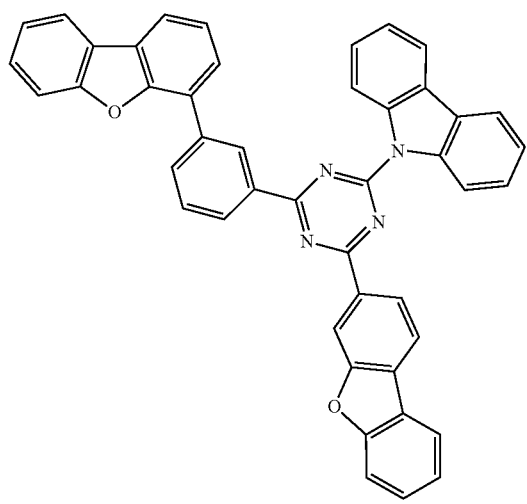
[B-25]
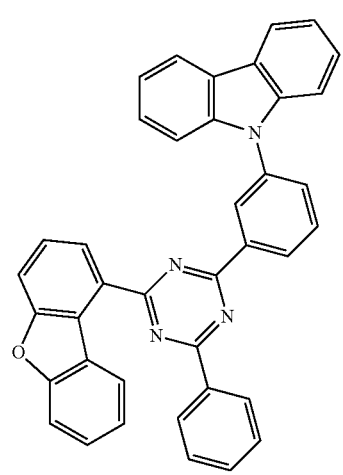
[C-1]
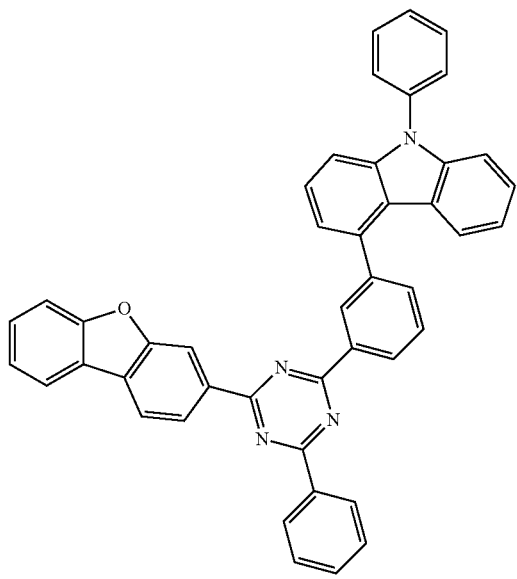
[C-2]
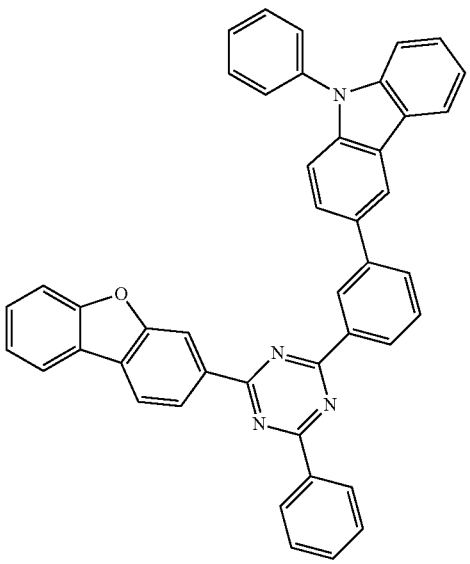
[C-3]
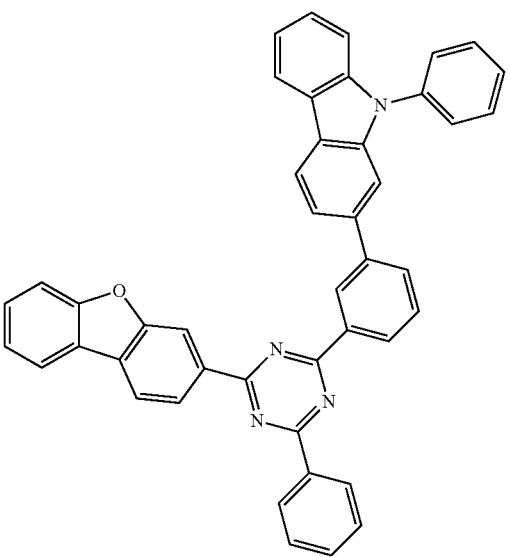

[C-4]
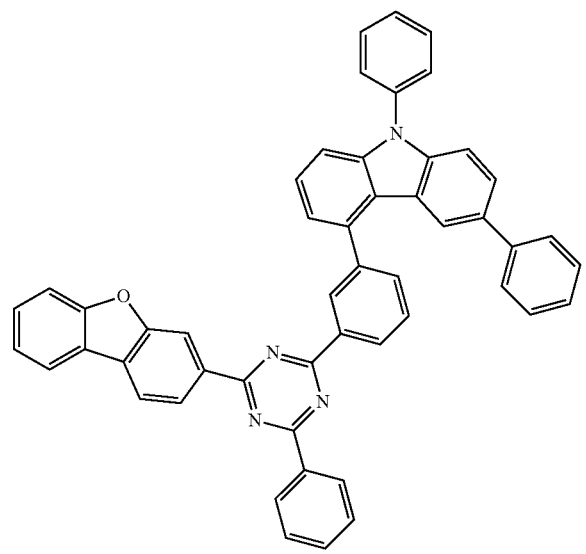
[C-5]
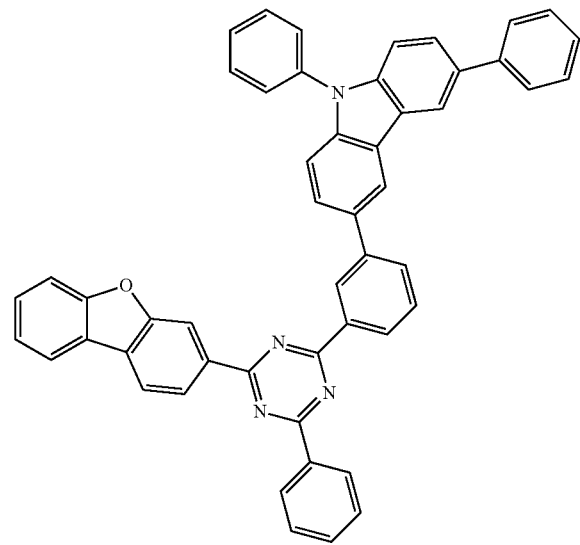
[C-6]
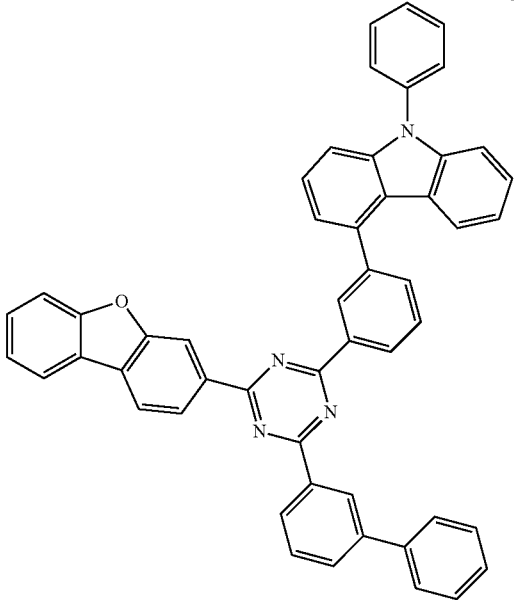
[C-7]
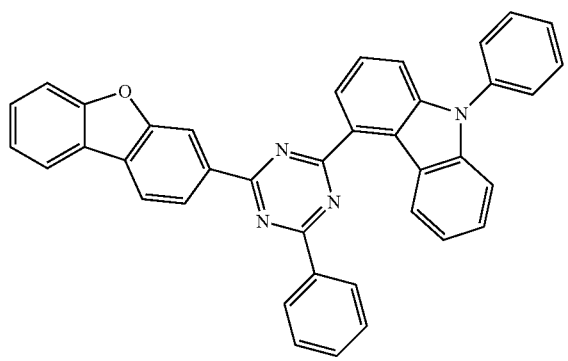
[C-8]

[C-9]
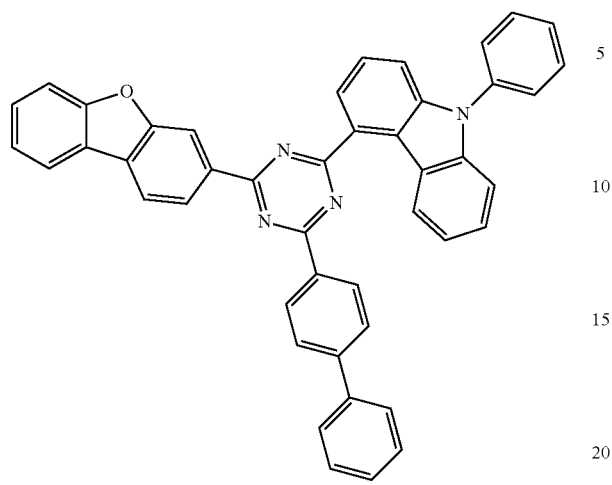
[C-12]
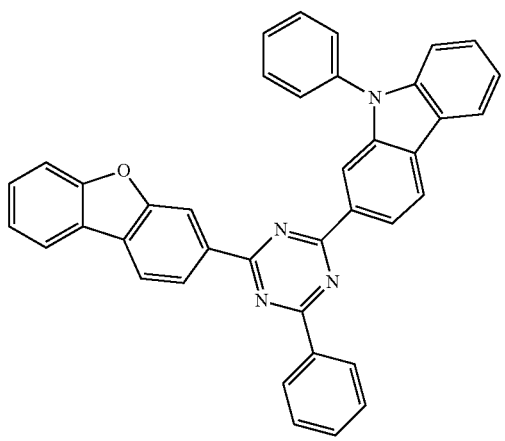
[C-10]
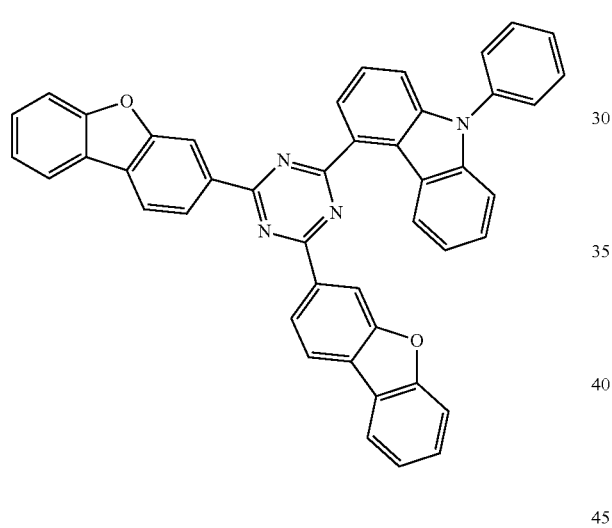
[C-13]
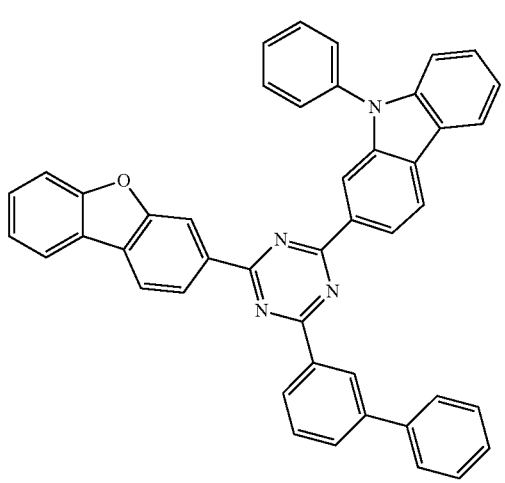
[C-11]
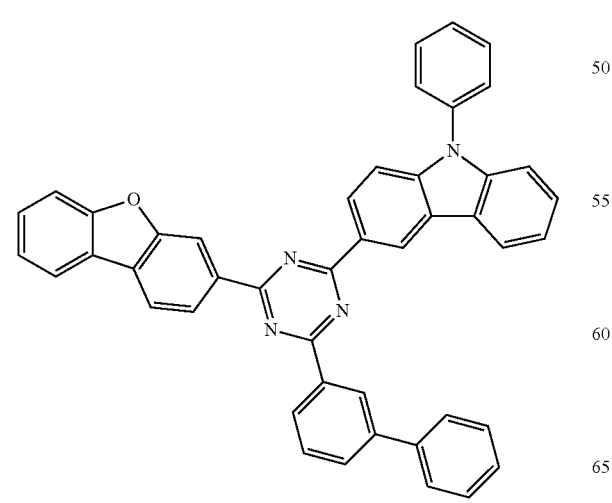
[C-14]
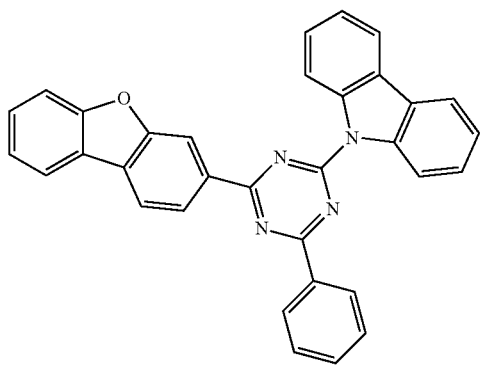

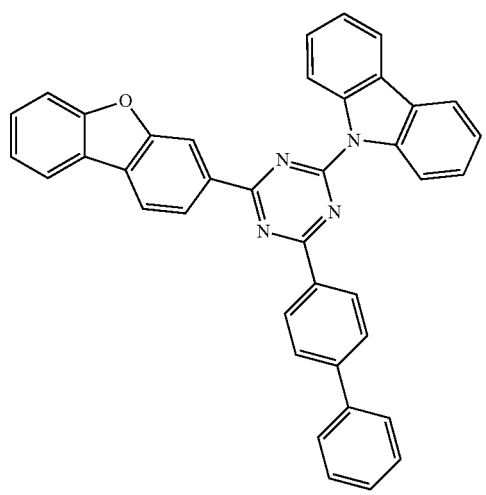
[C-15]
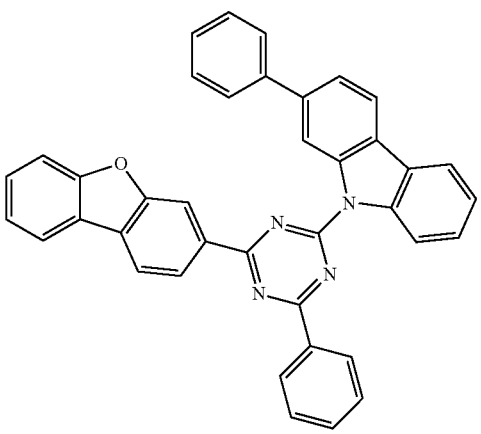
[C-18]
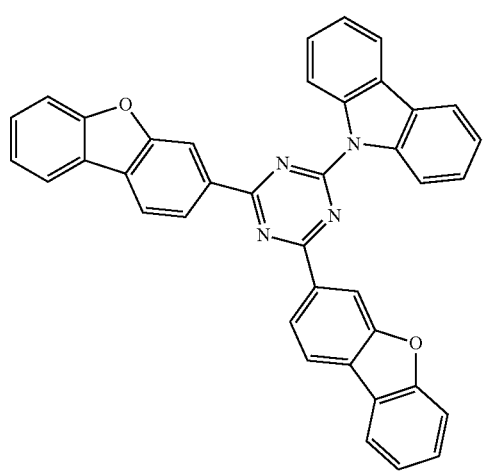
[C-16]
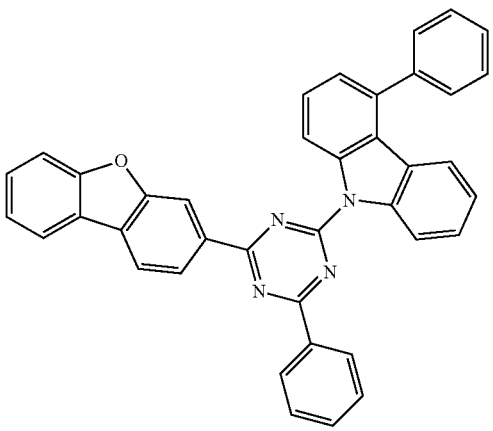
[C-19]
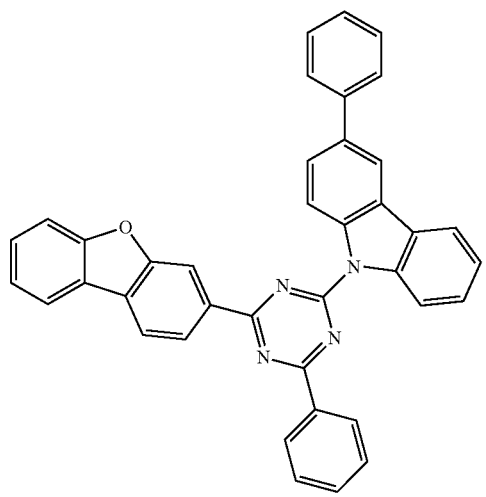
[C-17]
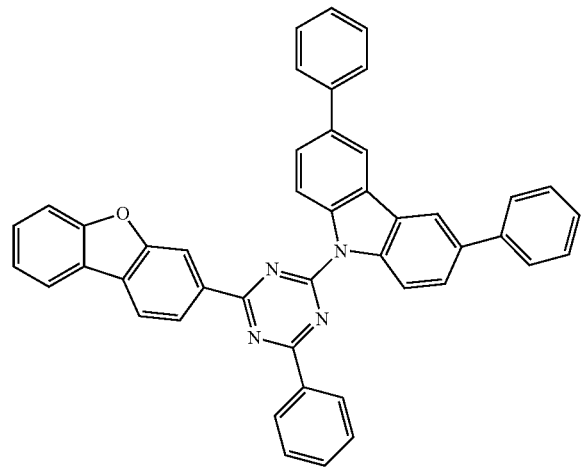
[C-20]

[C-21]
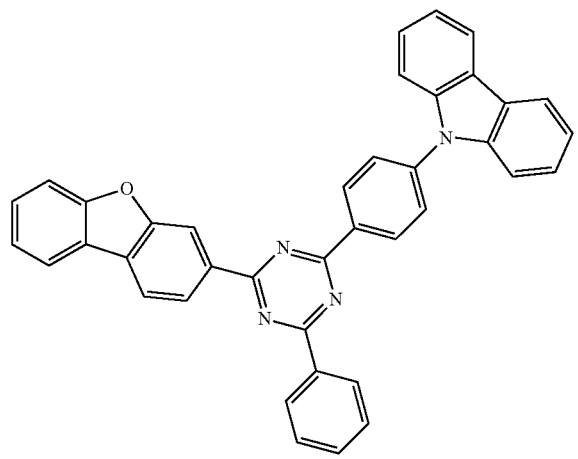
[C-22]
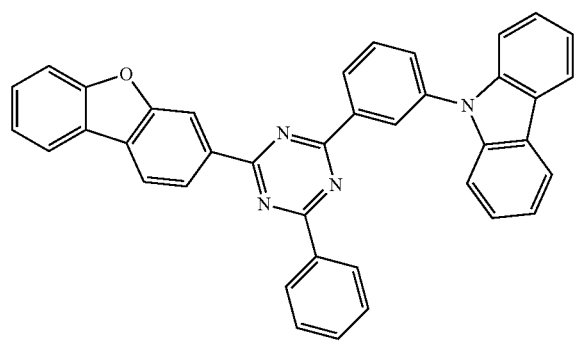
[C-23]
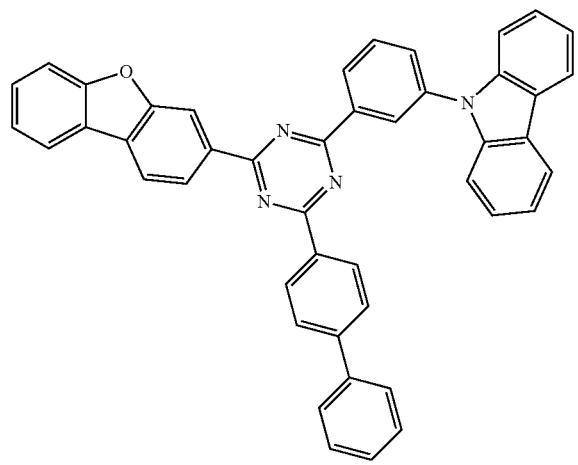
[C-24]
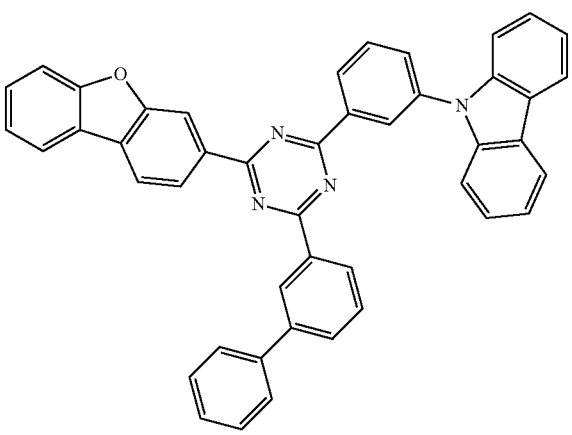
[C-25]
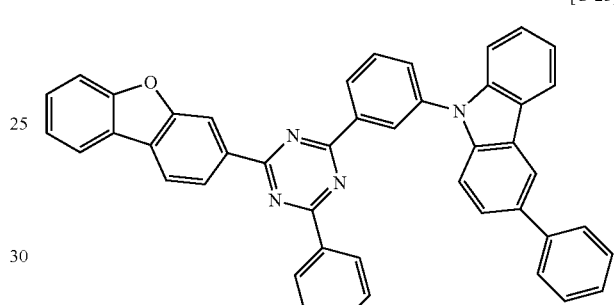
[C-26]
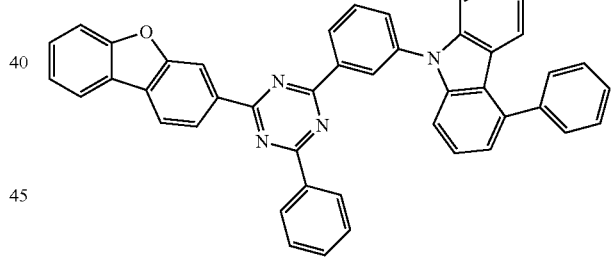
[C-27]
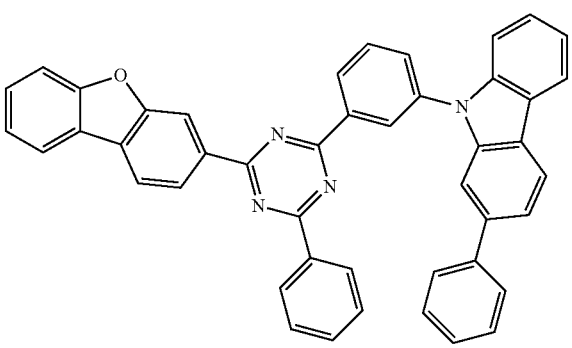

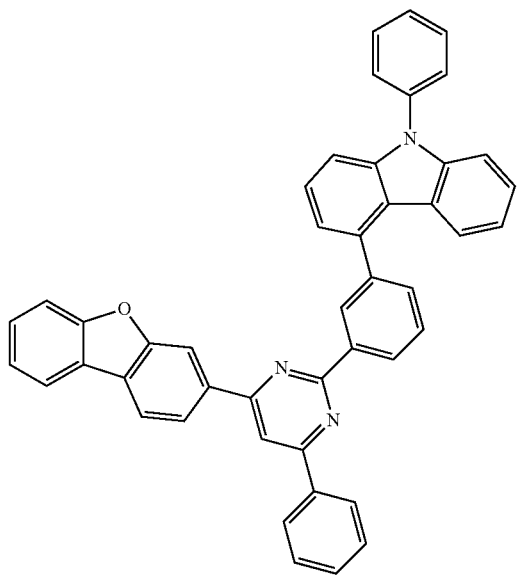
[C-28]
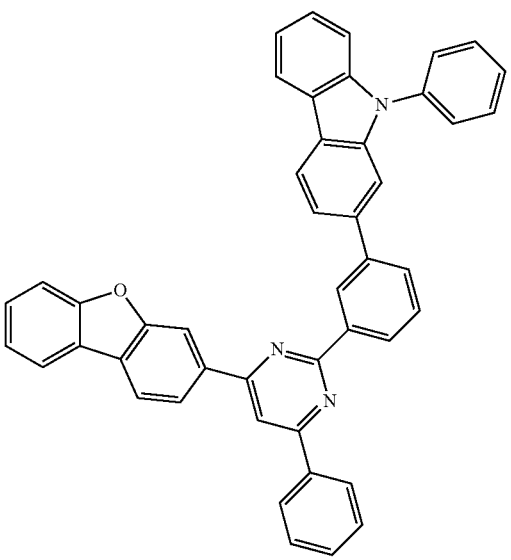
[C-30]
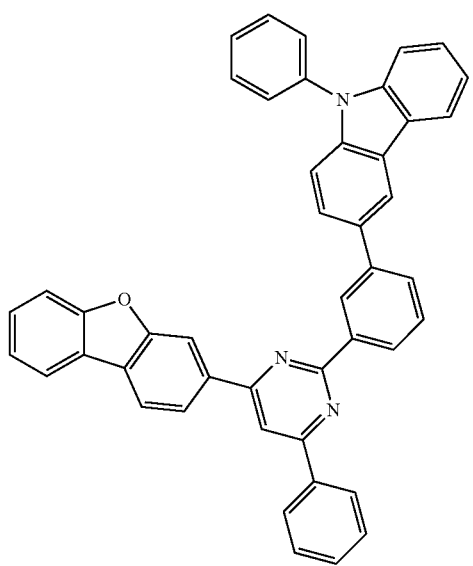
[C-29]
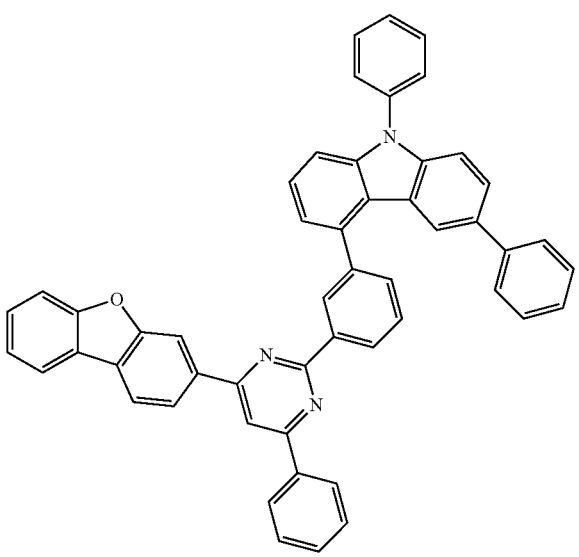
[C-31]

[C-32]
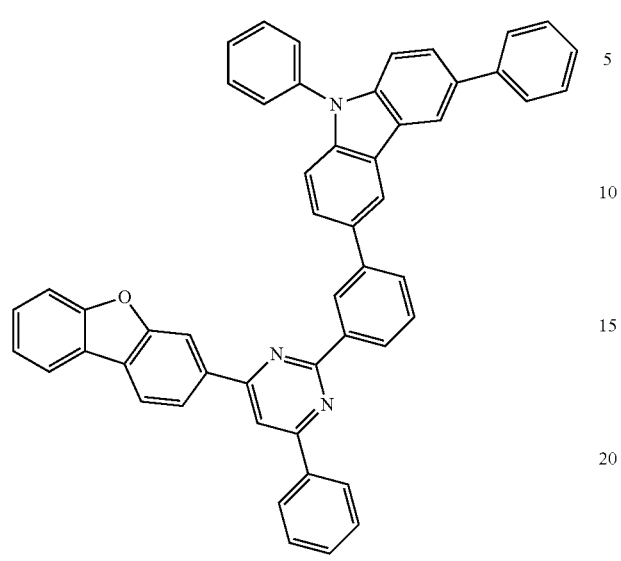
[C-33]
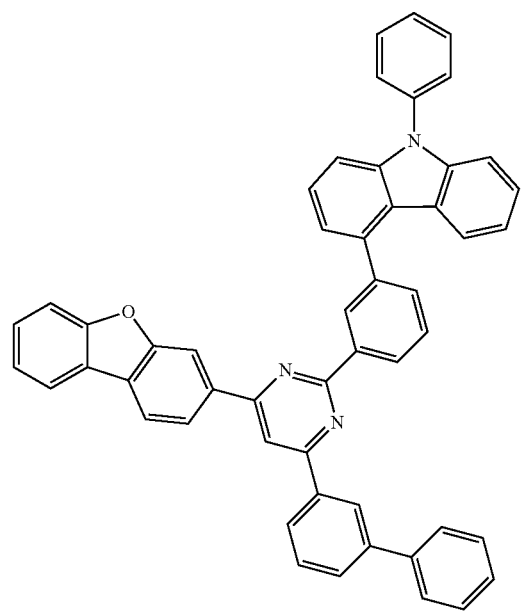
[C-34]
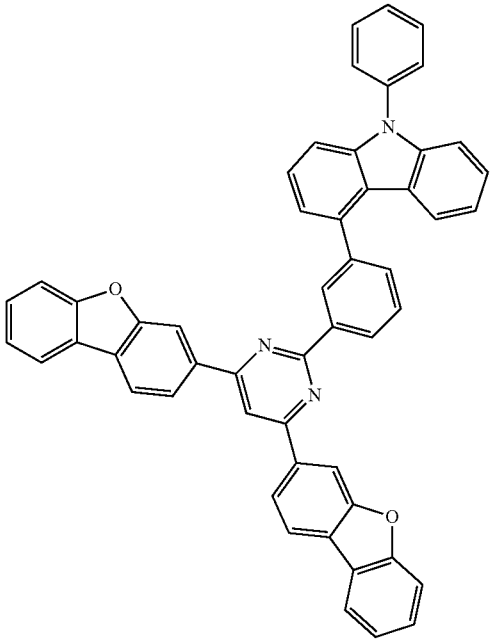
[C-35]
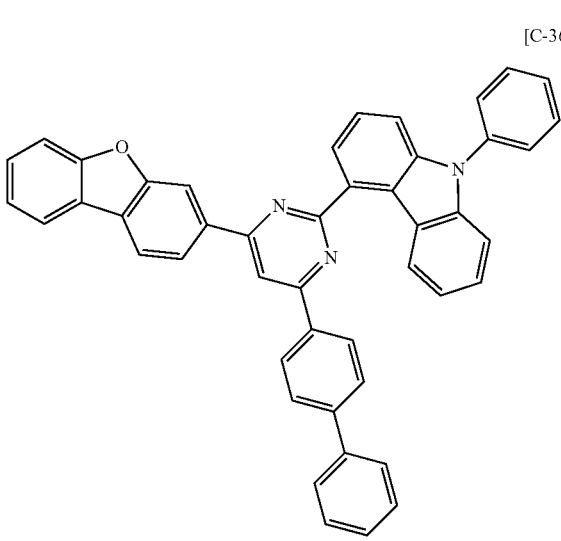
[C-36]

[C-37]
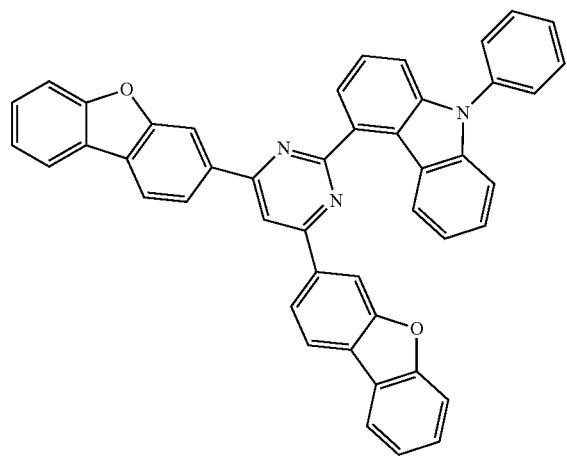
[C-38]
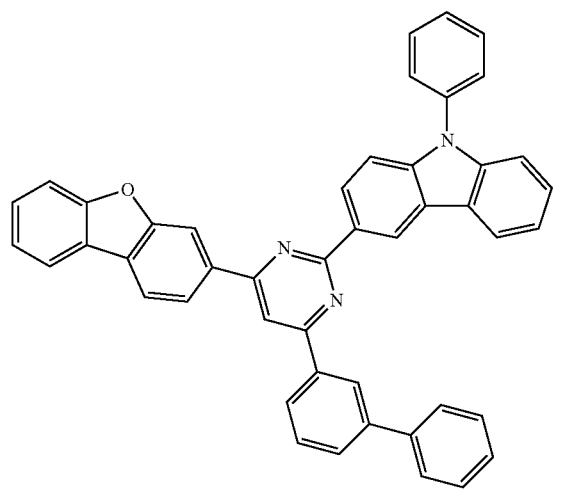
[C-39]
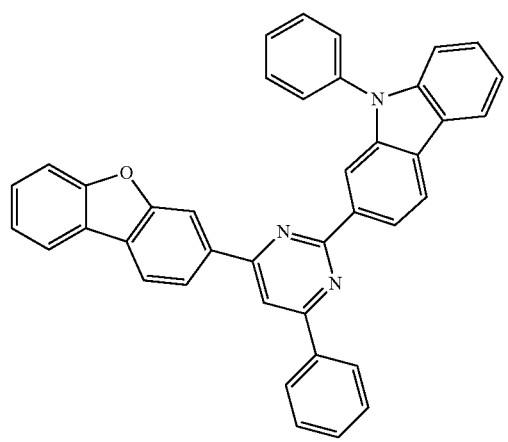
[C-40]
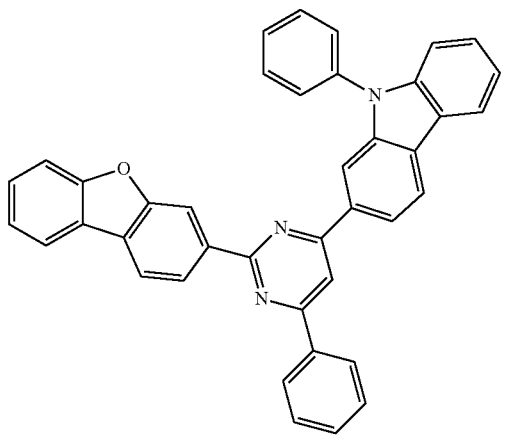
[C-41]
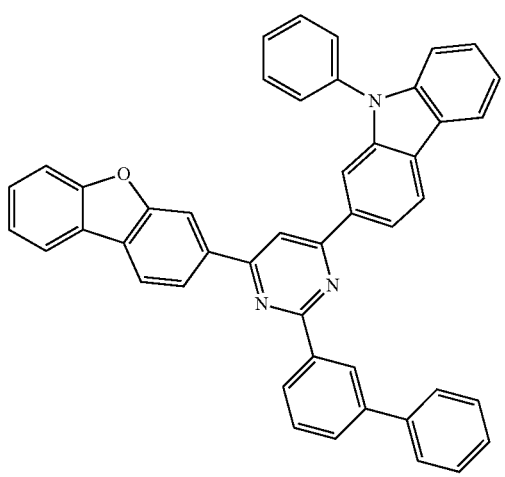
[C-42]
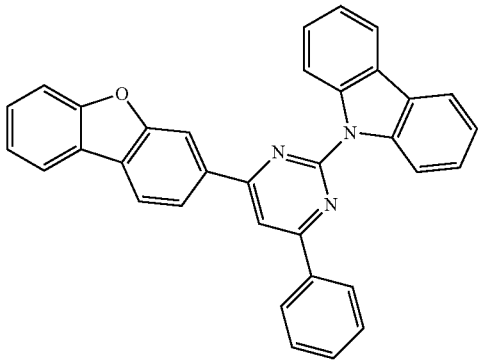

[C-43]
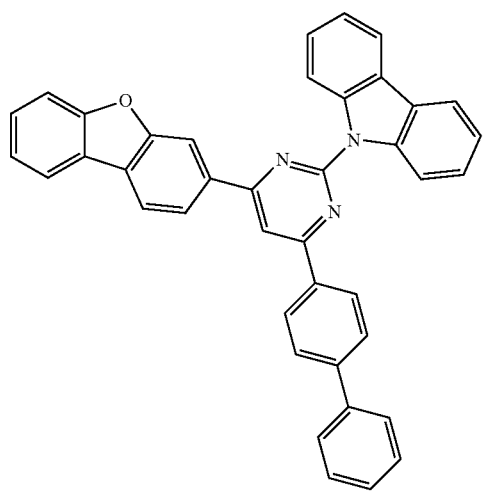
[C-46]
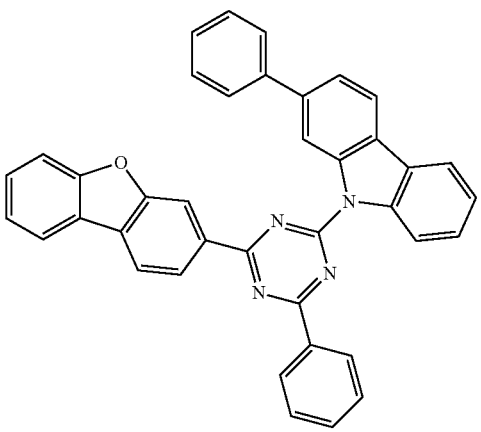
[C-44]
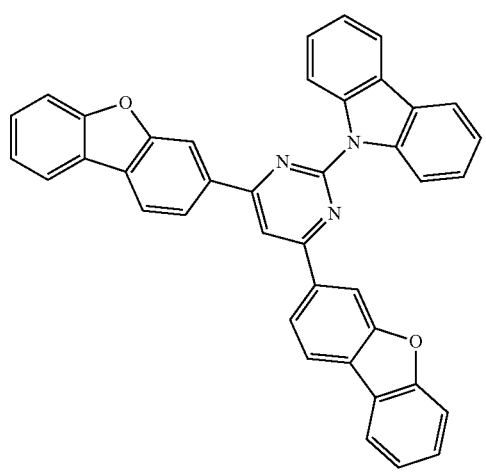
[C-47]
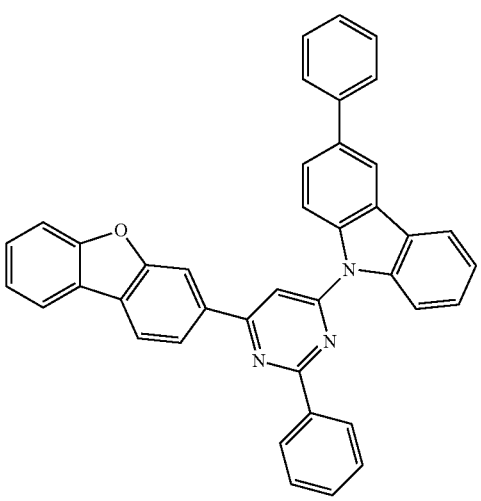
[C-45]
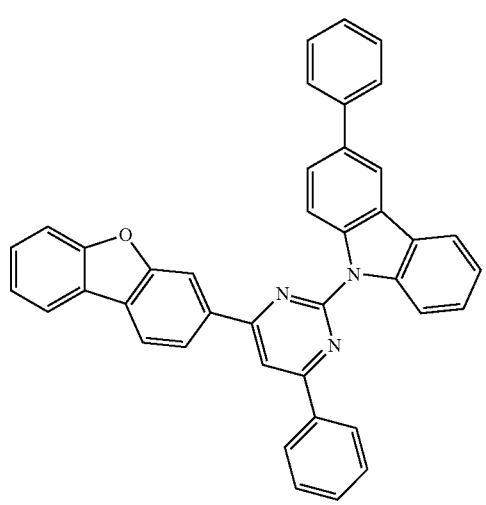
[C-48]
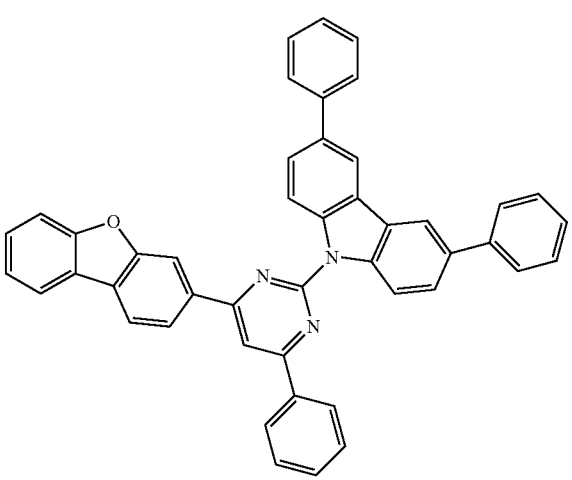

[C-49]
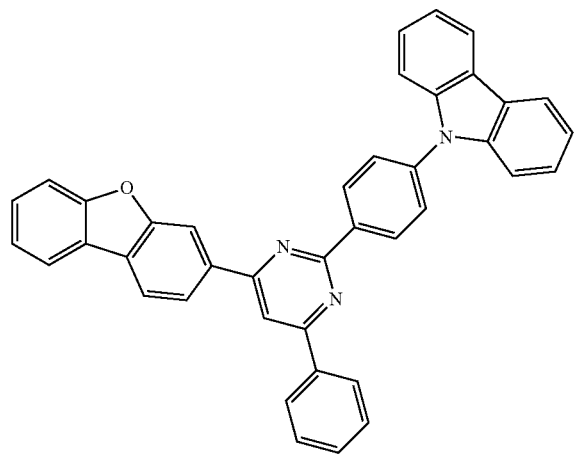
[C-50]
[C-51]
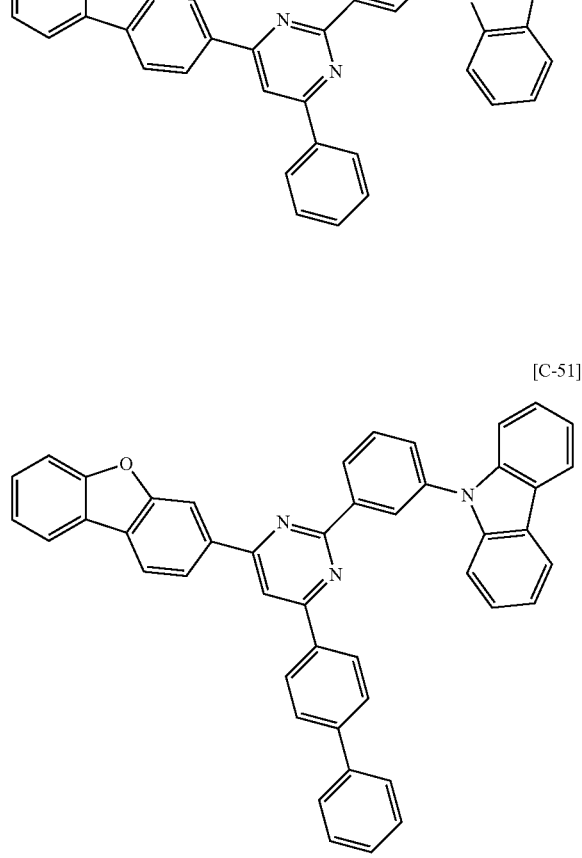
[C-52]
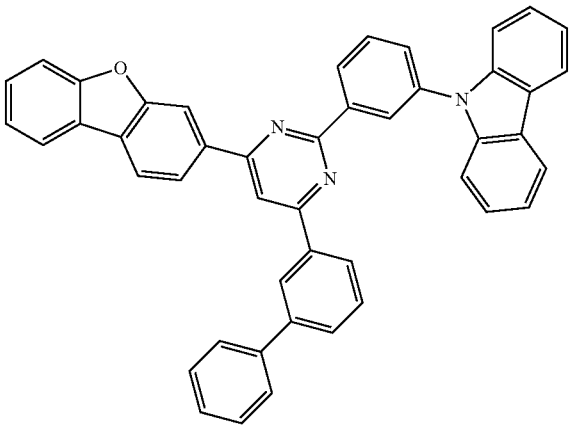
[C-53]
[C-54]
[C-55]
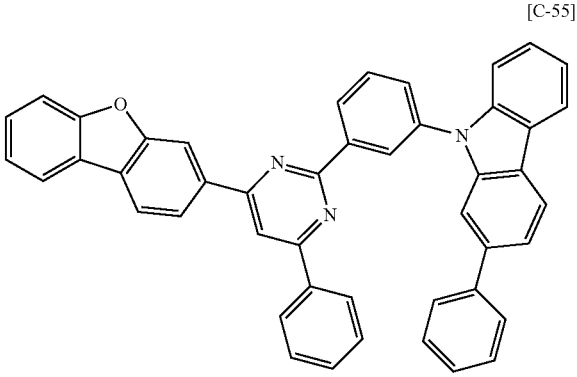

[C-56]
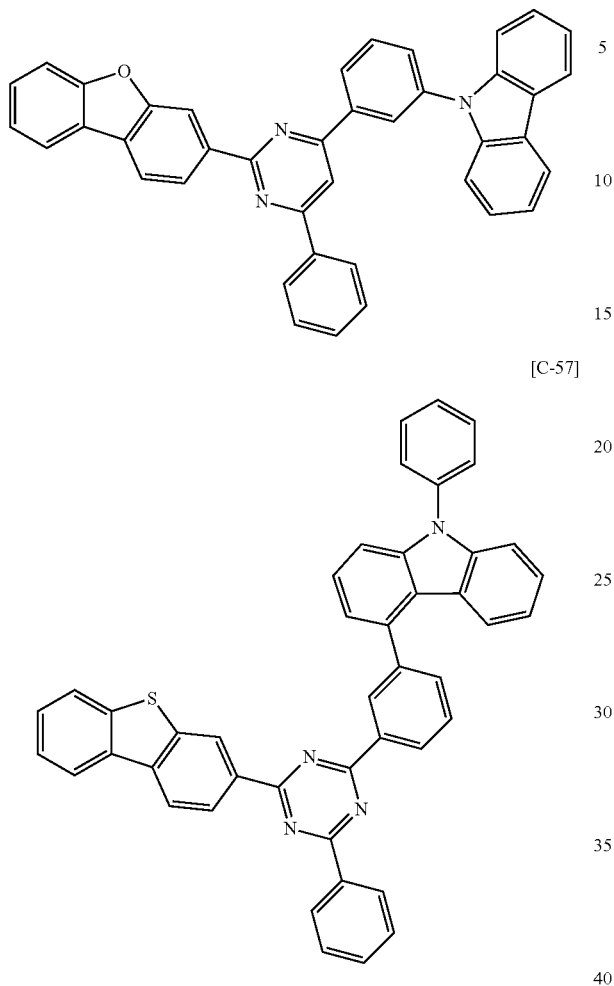
[C-57]
[C-58]
[C-59]
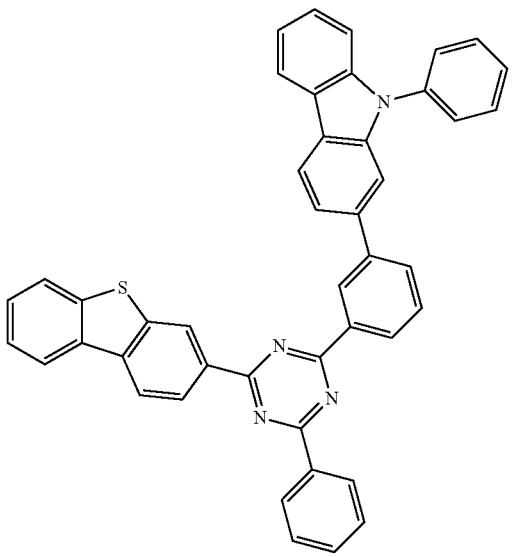
[C-60]
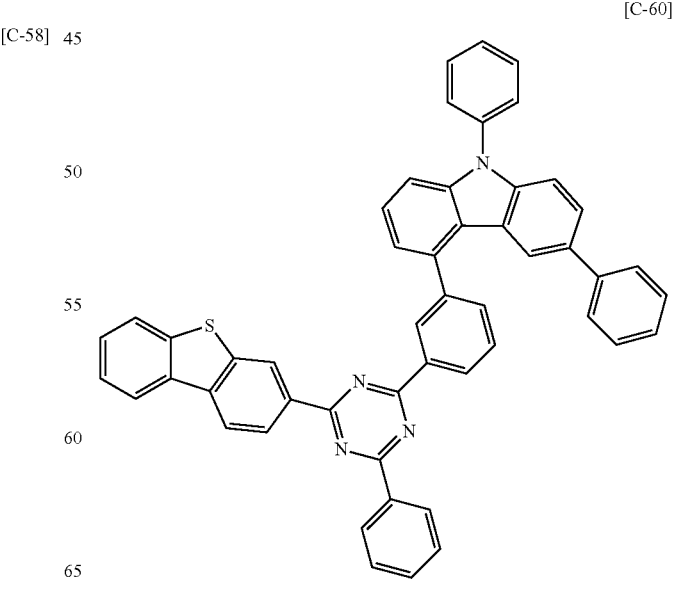

[C-61]
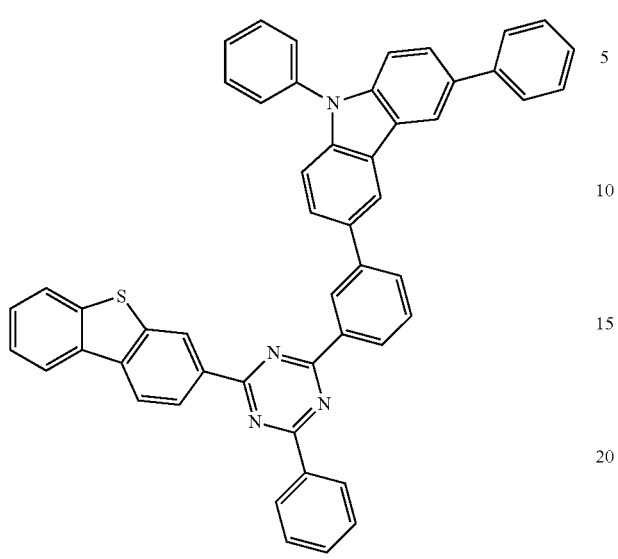
[C-62]
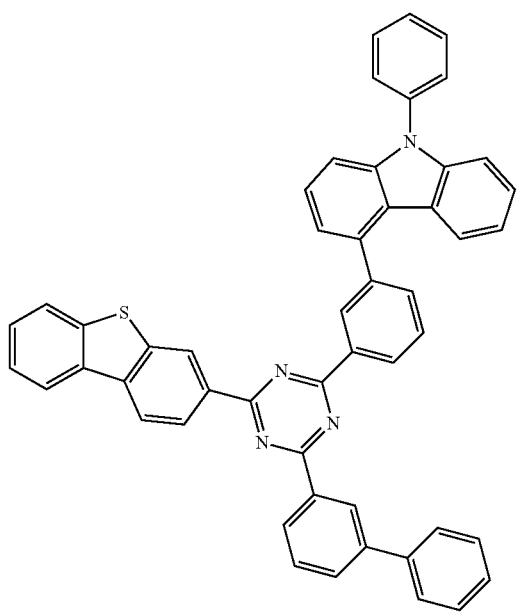
[C-63]
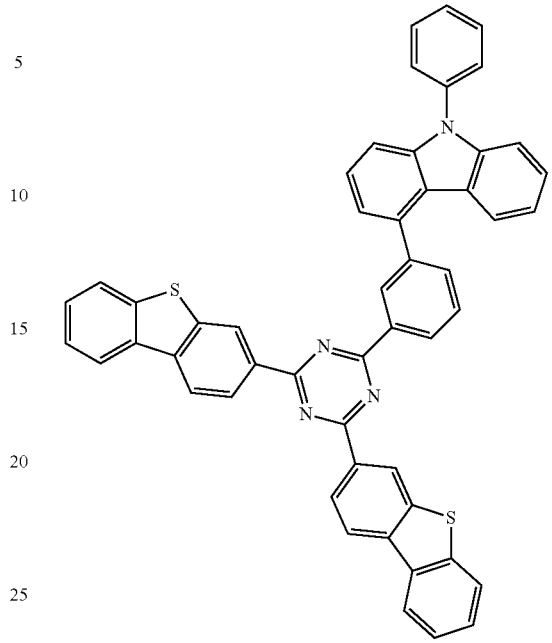
[C-64]
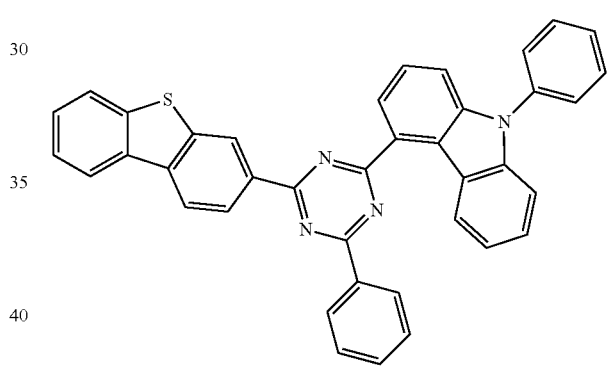
[C-65]
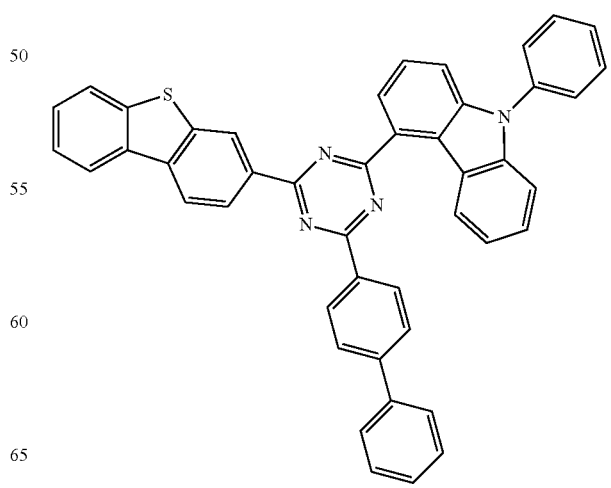

-continued
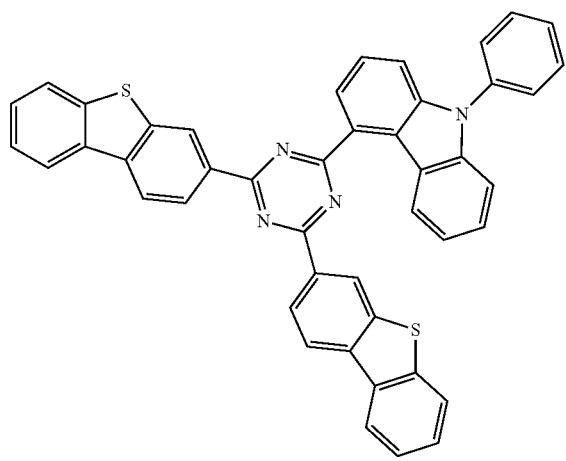
[C-66]
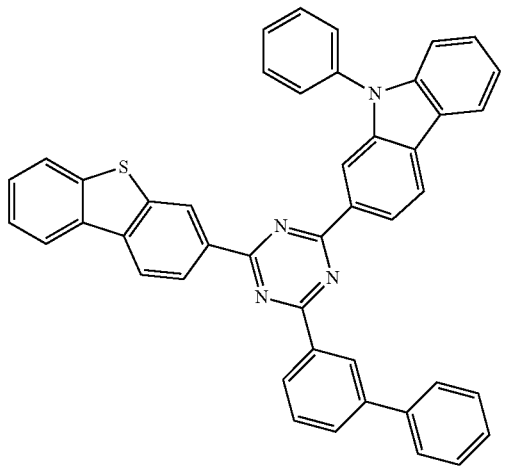
[C-68]
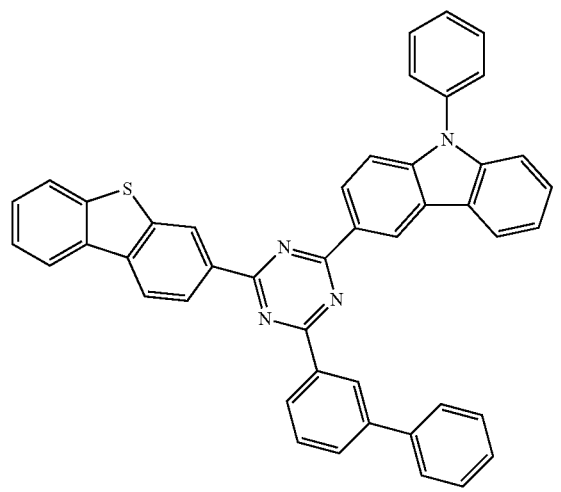
[C-66]
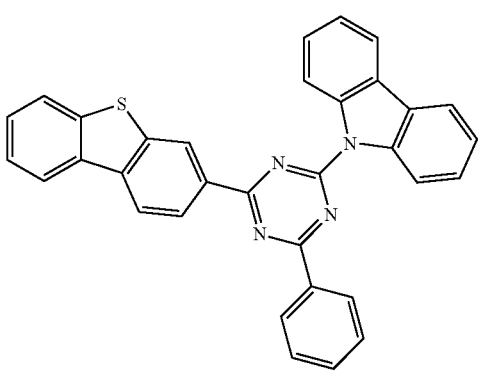
[C-69]
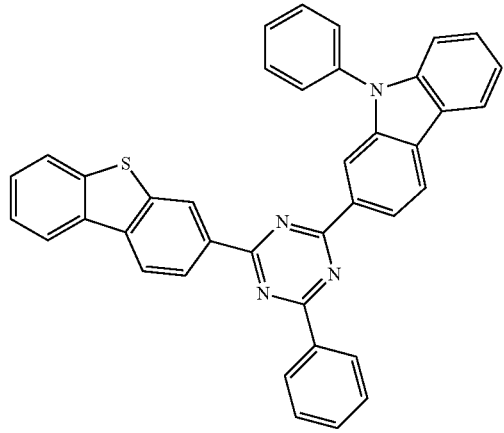
[C-67]
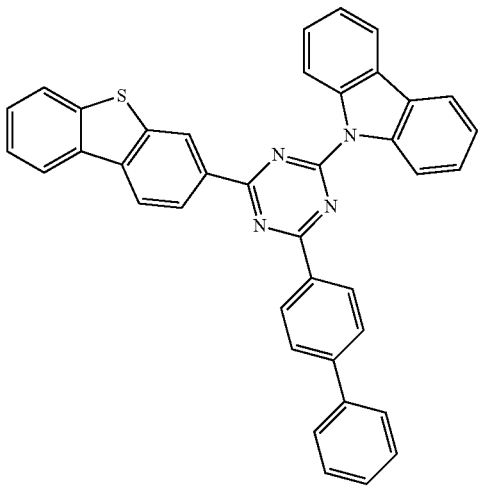
[C-70]

[C-71]
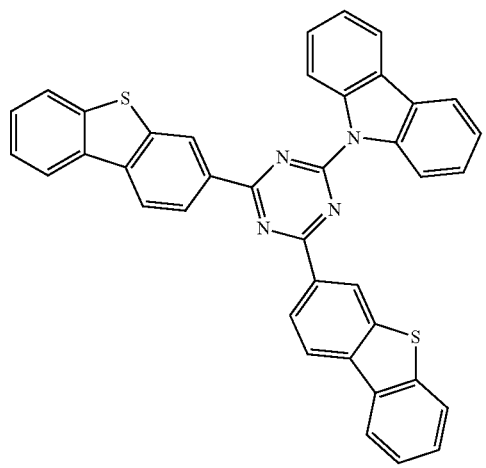
[C-72]
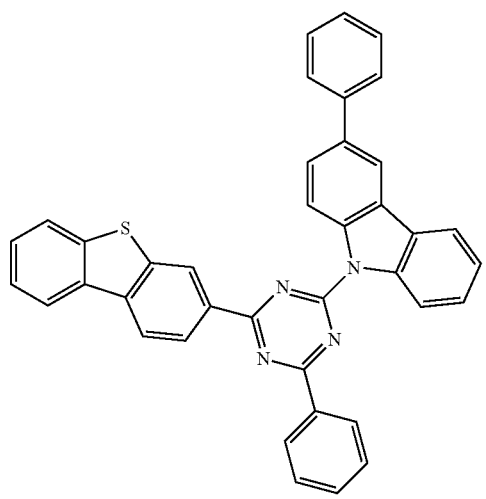
[C-73]
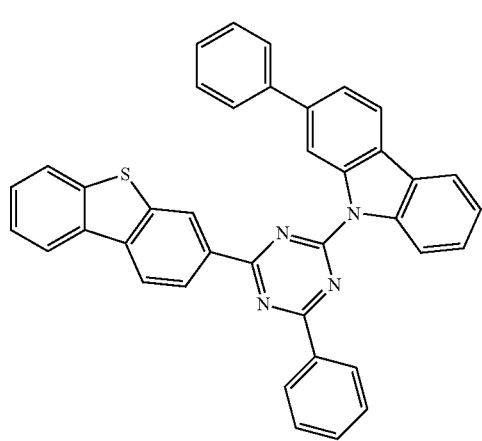
[C-74]
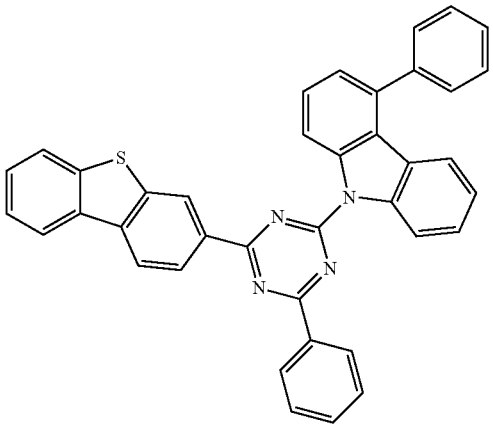
[C-75]
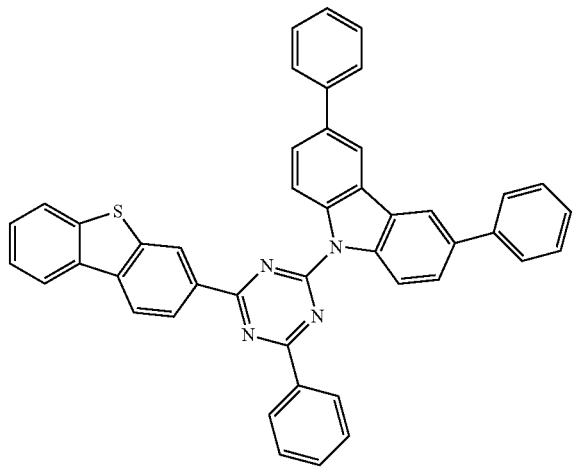
[C-76]
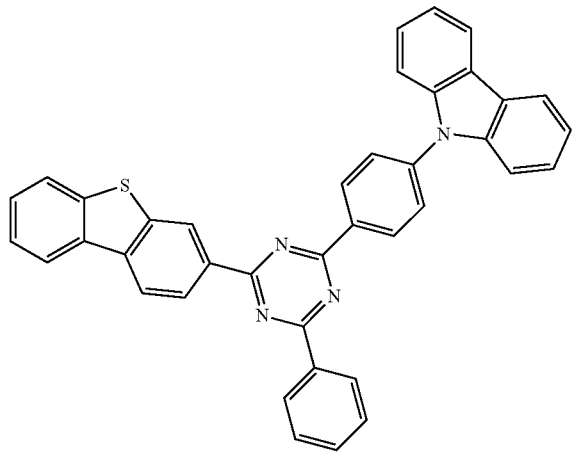

[C-77]
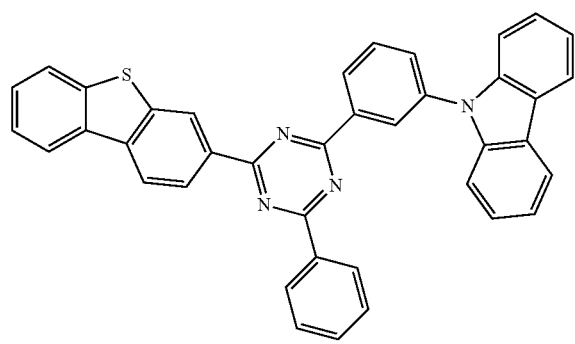
[C-78]
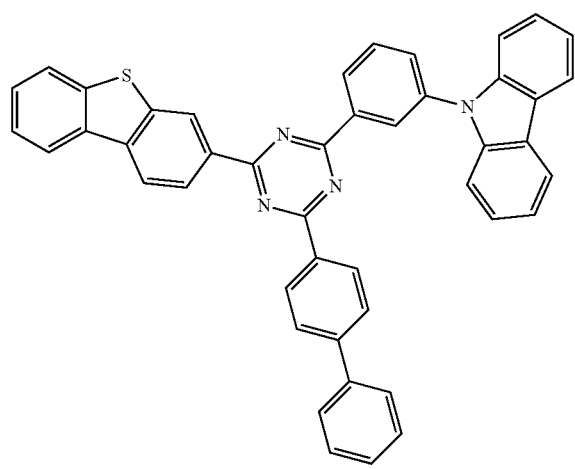
[C-79]
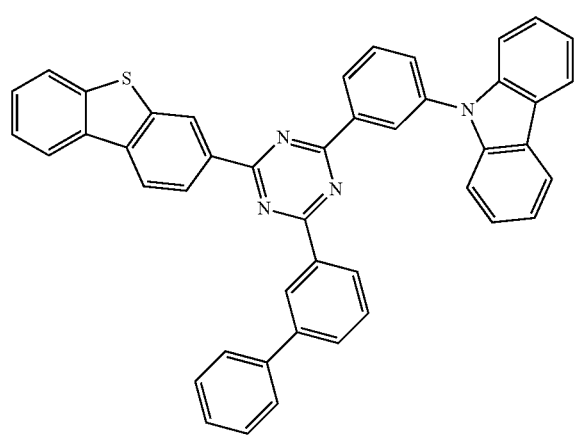
[C-80]
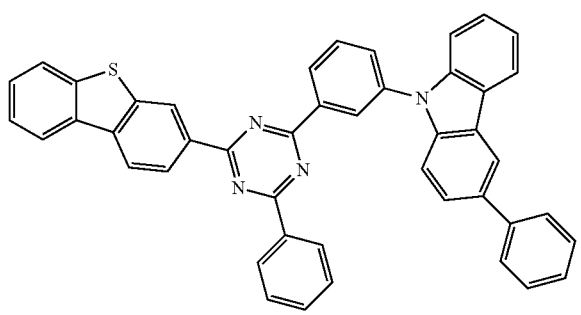
[C-81]
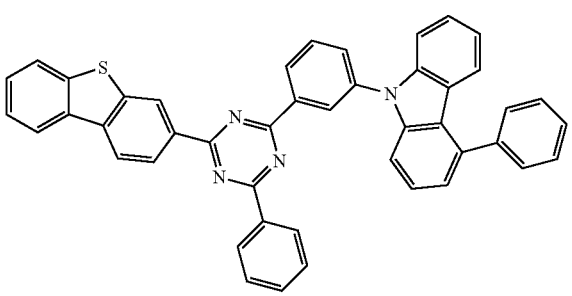
[C-82]
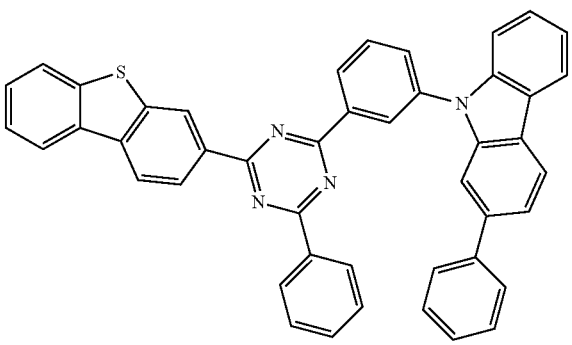
[C-83]
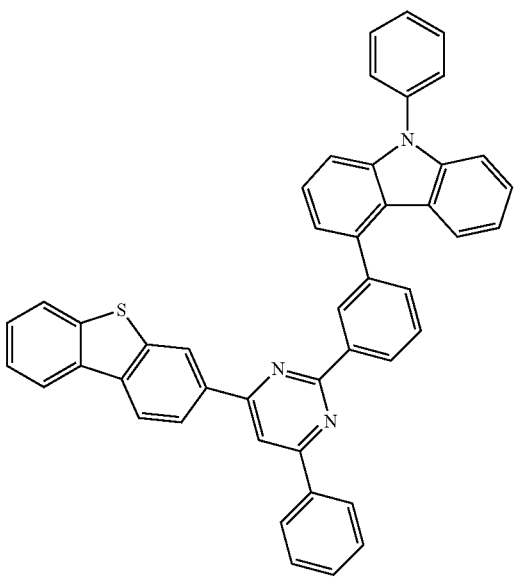

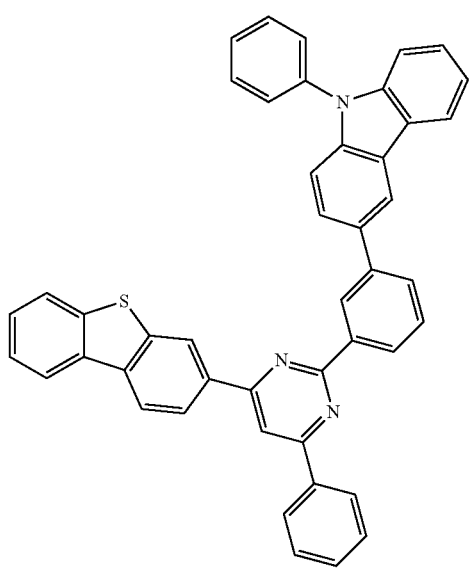
[C-84]
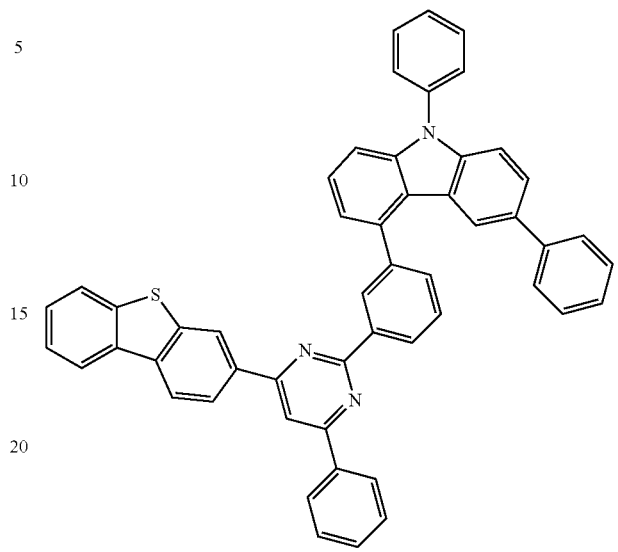
[C-86]
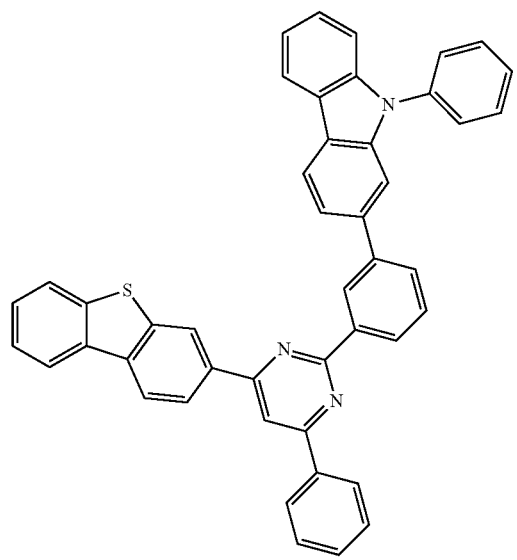
[C-85]

-continued
[C-88]
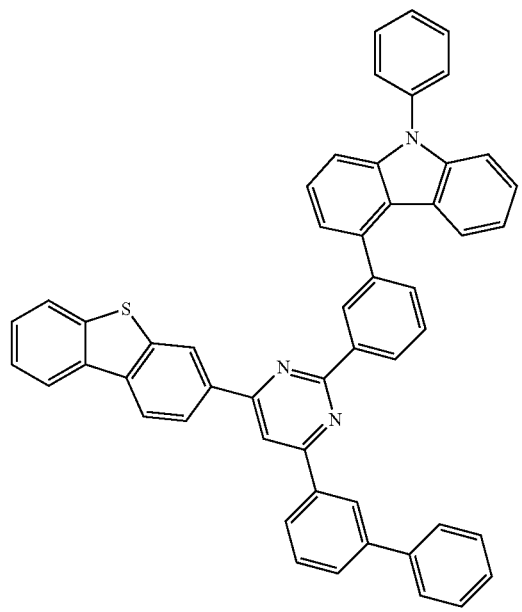
[C-89]
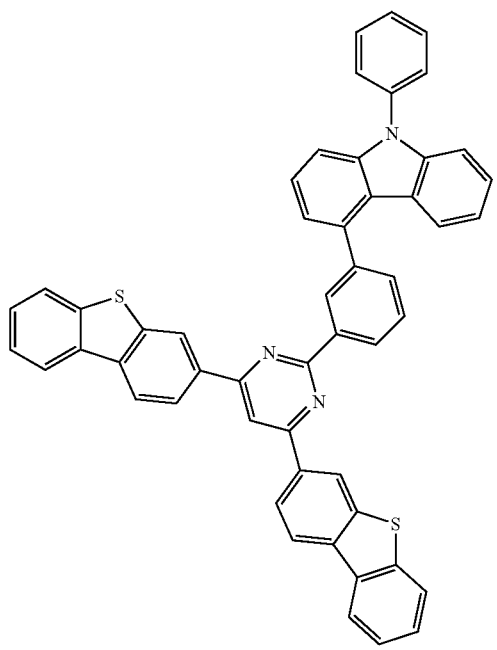
[C-90]
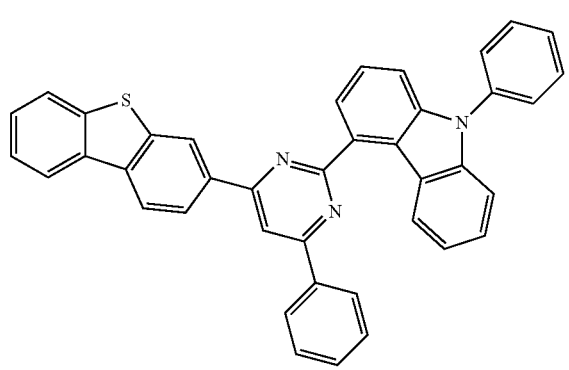
[C-91]
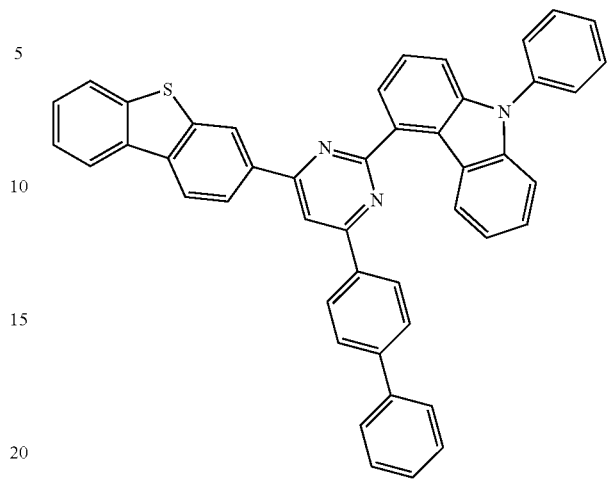
[C-92]
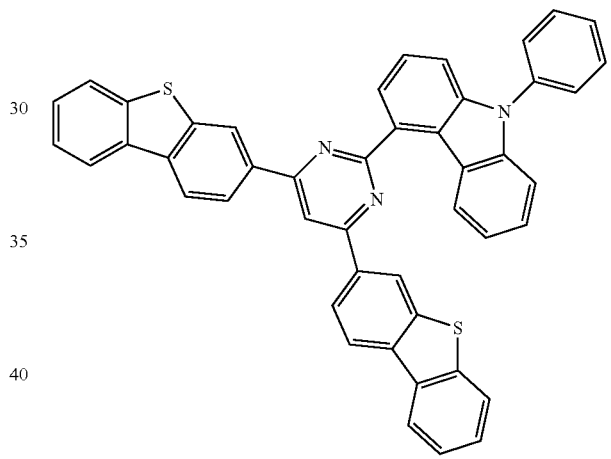
[C-93]
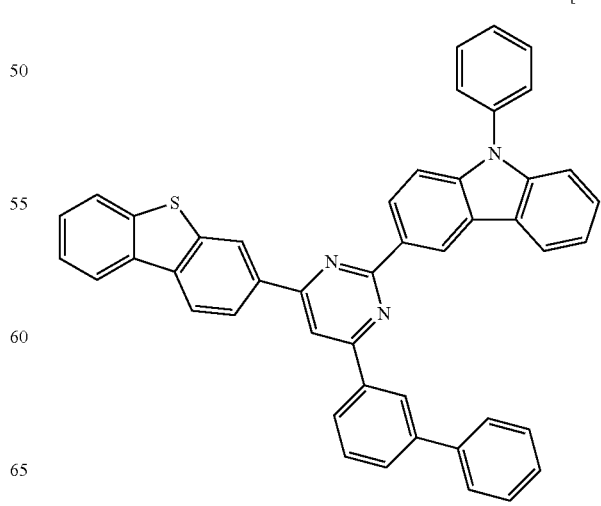

[C-94]
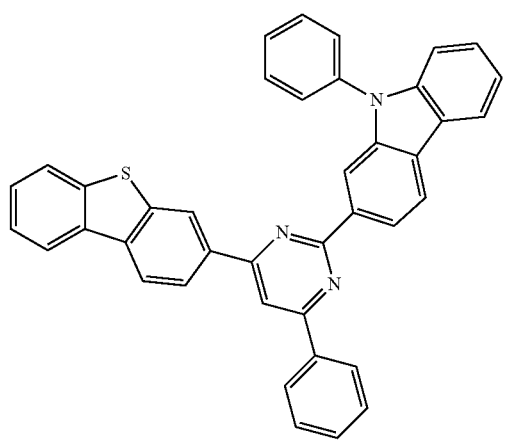
[C-95]
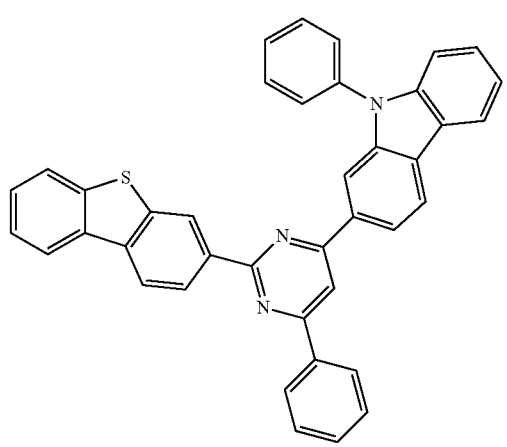
[C-96]
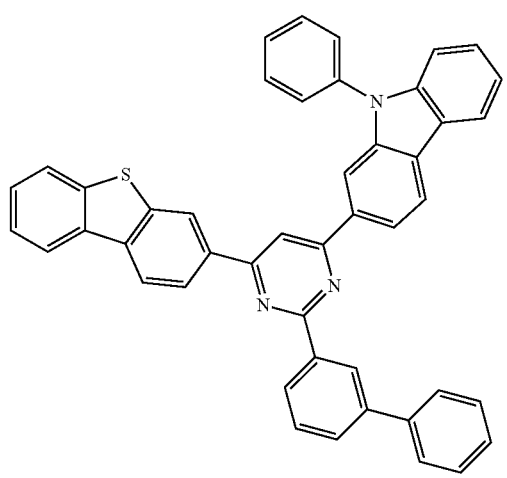
[C-97]
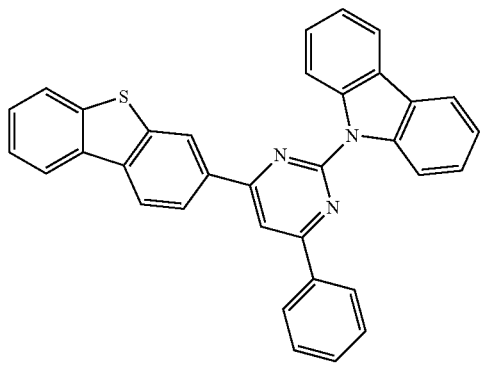
[C-98]
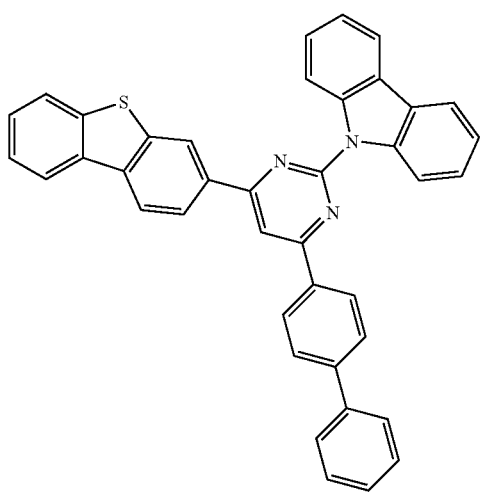
[C-99]
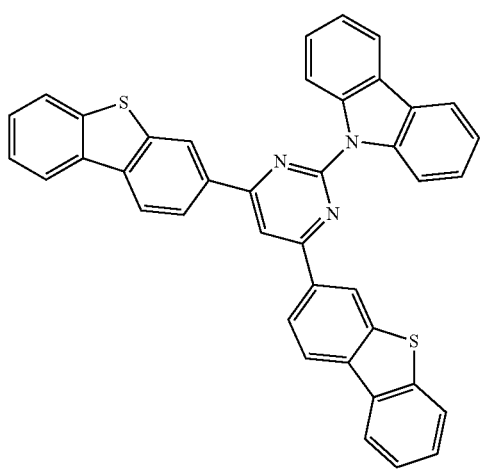

[C-100]
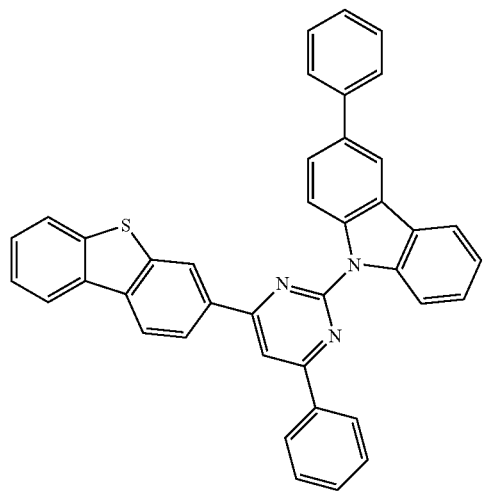
[C-101]
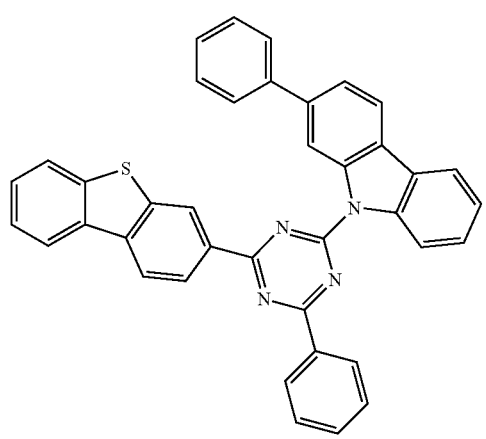
[C-102]
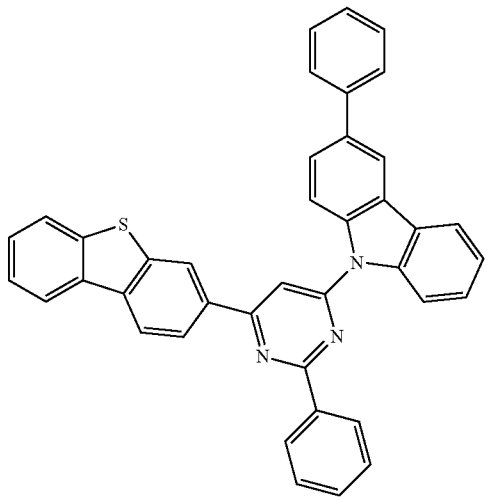
[C-103]
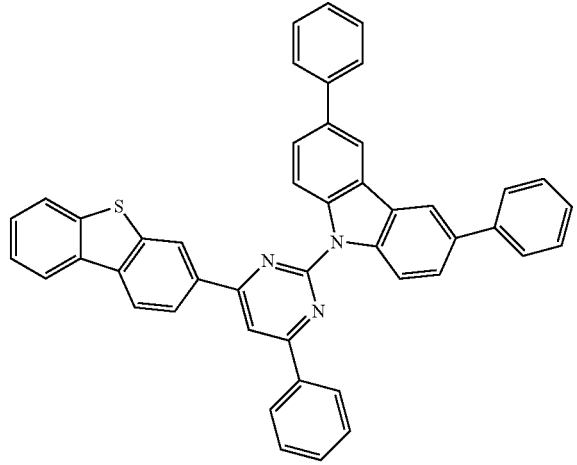
[C-104]
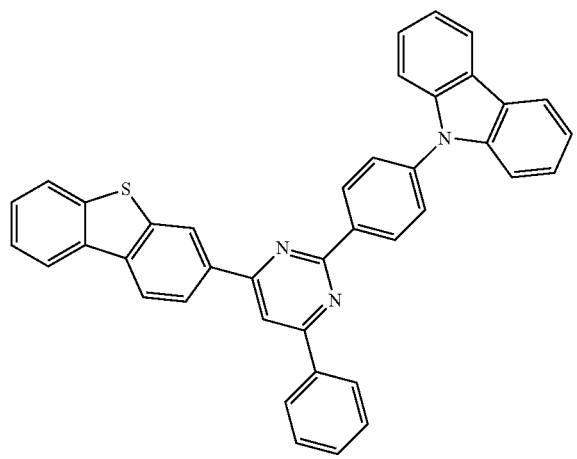
[C-105]
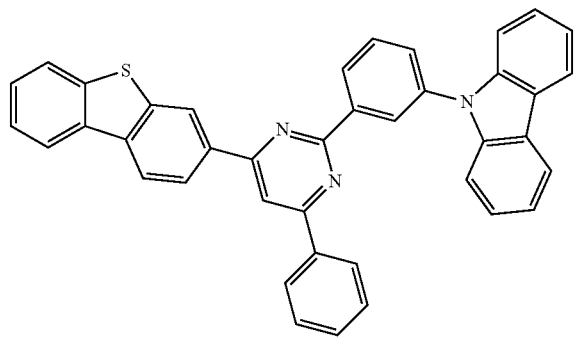

[C-106]
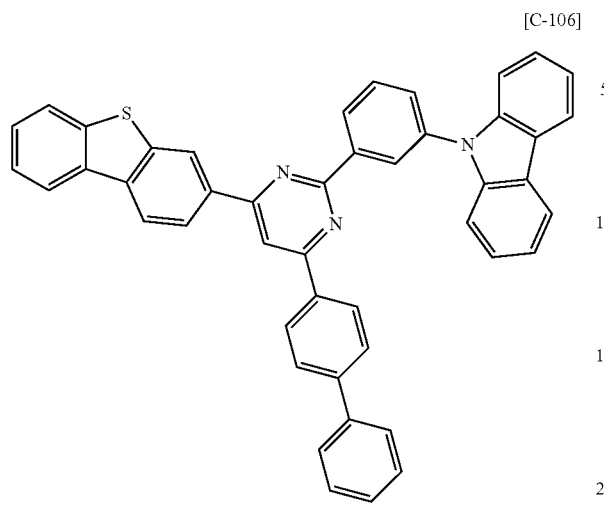

[C-107]
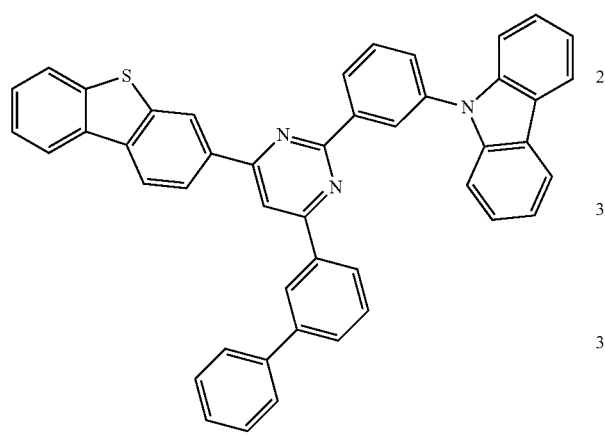

[C-108]
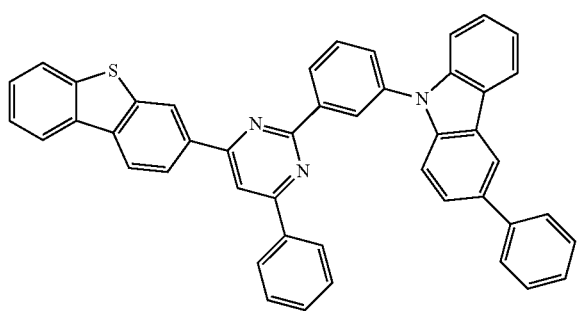

[C-109]
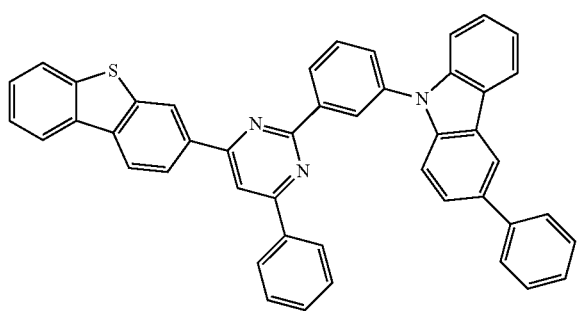

[C-110]
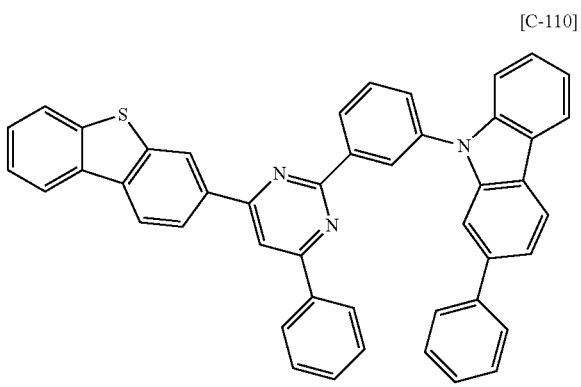

[C-111]
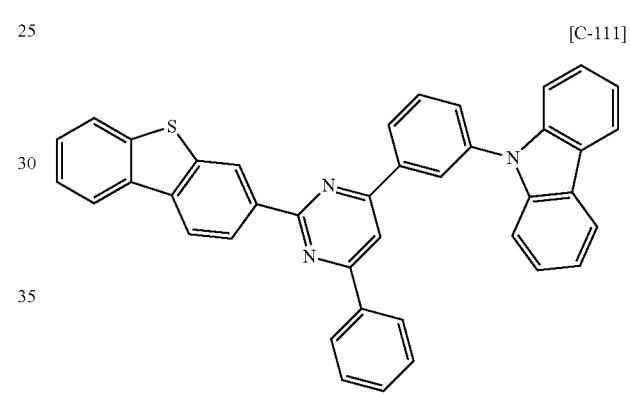

In an example embodiment of the present invention, the second host may be for example represented by one of Chemical Formula 2A, Chemical Formula 2B, Chemical Formula 2C, Chemical Formula 2D, and Chemical Formula 2E, and in a specific example embodiment, the second host may be for example represented by one of Chemical Formula 2A, Chemical Formula 2B, Chemical Formula 2C, and Chemical Formula 2D, and preferably Chemical Formula 2B according to a fusion position of Chemical Formula 2 and Chemical Formula 3.

[Chemical Formula 2A]
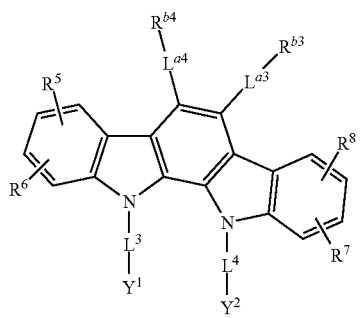

[Chemical Formula 2B]

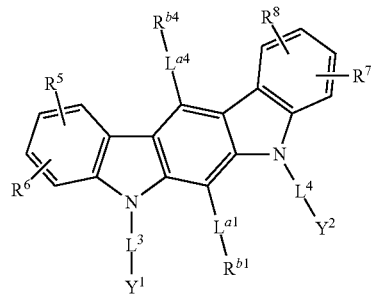

[Chemical Formula 2C]

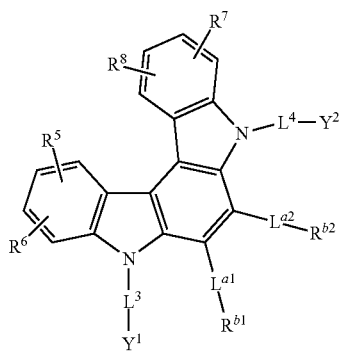

[Chemical Formula 2D]

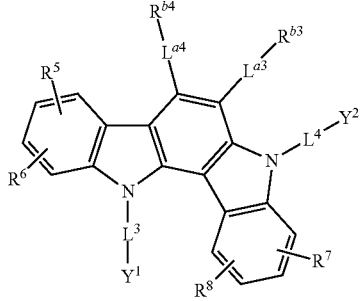

[Chemical Formula 2E]

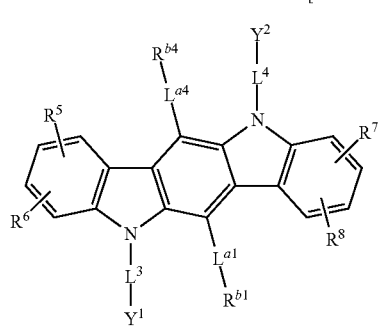

In Chemical Formula 2A to Chemical Formula 2E, $Y^1$ and $Y^2$, $L^3$ and $L^4$ and $R^5$ to $R^8$ are the same as described above, $L^{a1}$ to $L^{a4}$ are the same as $L^a$, and $R^{b1}$ to $R^{b4}$ are the same as $R^b$.

On the other hand, in an example embodiment of the present invention, the $Y^1$ and $Y^2$ may independently be a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, and in a specific example embodiment, $Y^1$ and $Y^2$ may independently be a substituted or unsubstituted phenyl group, or a substituted or unsubstituted biphenyl group, and preferably $Y^1$ and $Y^2$ may independently be a phenyl group or a para-biphenyl group.

In addition, in an example embodiment of the present invention, $R^{b1}$ to $R^{b4}$ and $R^5$ to $R^8$ may independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group, in a specific example embodiment, $R^{b1}$ to $R^{b4}$ may independently be hydrogen, deuterium, a cyano group, a substituted or unsubstituted phenyl group, a substituted or unsubstituted biphenyl group, a substituted or unsubstituted pyridinyl group, a substituted or unsubstituted carbazolyl group, a substituted or unsubstituted dibenzofuranyl group, or a substituted or unsubstituted dibenzothiophenyl group and $R^5$ to $R^8$ may independently be hydrogen, deuterium, a cyano group, a substituted or unsubstituted phenyl group, or a substituted or unsubstituted biphenyl group, and in more specific example embodiment, $R^{b1}$ to $R^{b4}$ and $R^5$ to $R^8$ may be all hydrogen.

$Y^1$, $Y^2$, $R^{b1}$ to $R^{b4}$, and $R^5$ to $R^8$ may be for example selected from substituents of Group II.

[Group II]

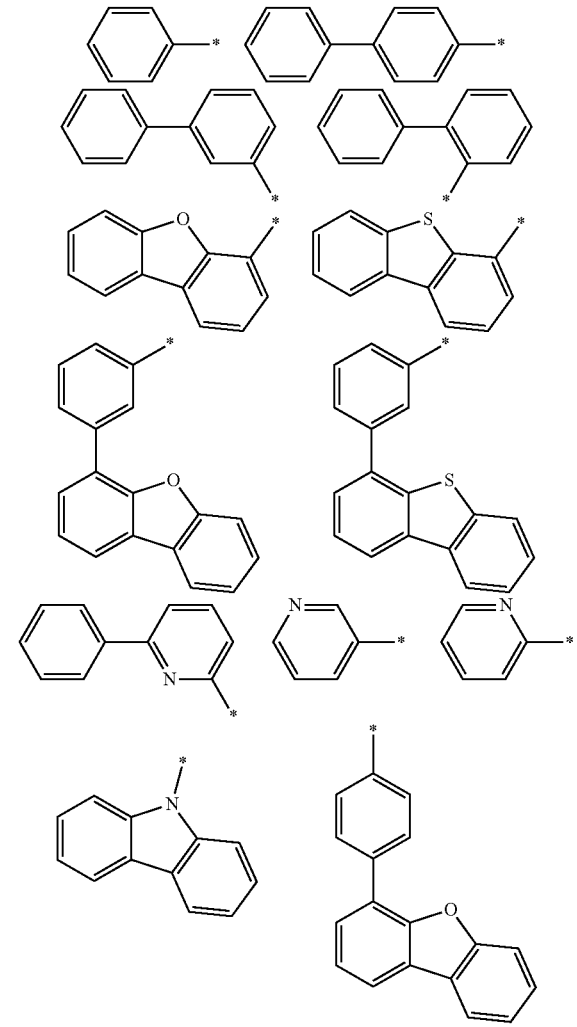

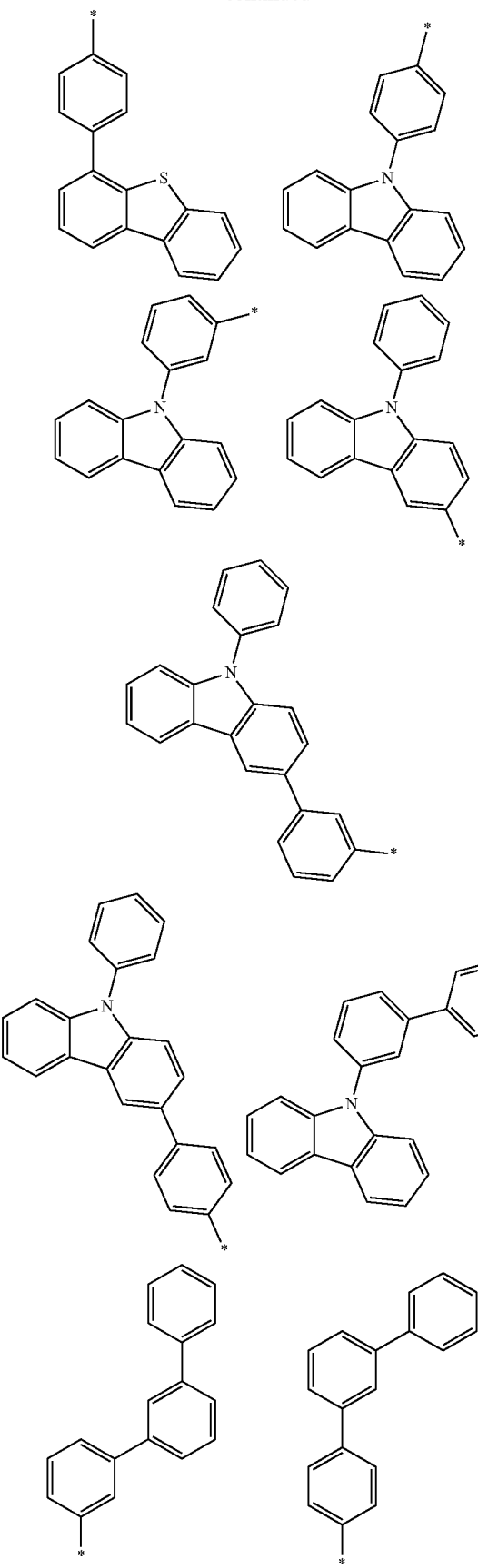
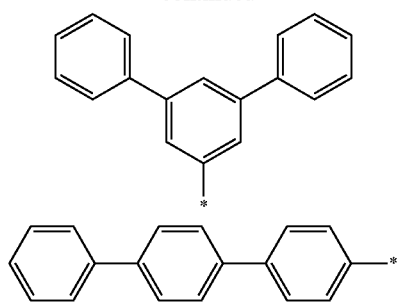

In Group II, * is a linking point.

In addition, in an example embodiment of the present invention, $L^{a1}$ to $L^{a4}$ and $L^3$ and $L^4$ may independently be a single bond, a substituted or unsubstituted para-phenylene group, a substituted or unsubstituted meta-phenylene group, or a substituted or unsubstituted biphenylene group, and in a specific example embodiment, $L^{a1}$ to $L^{a4}$ and $L^3$ and $L^4$ may independently be a single bond, a substituted or unsubstituted para-phenylene group, or a substituted or unsubstituted meta-phenylene group, and preferably $L^{a1}$ to $L^4$ and $L^3$ and $L^4$ may independently be a single bond or a para-phenylene group.

The second host may be for example selected from compounds of Group 2, but is not limited thereto.

[Group 2]

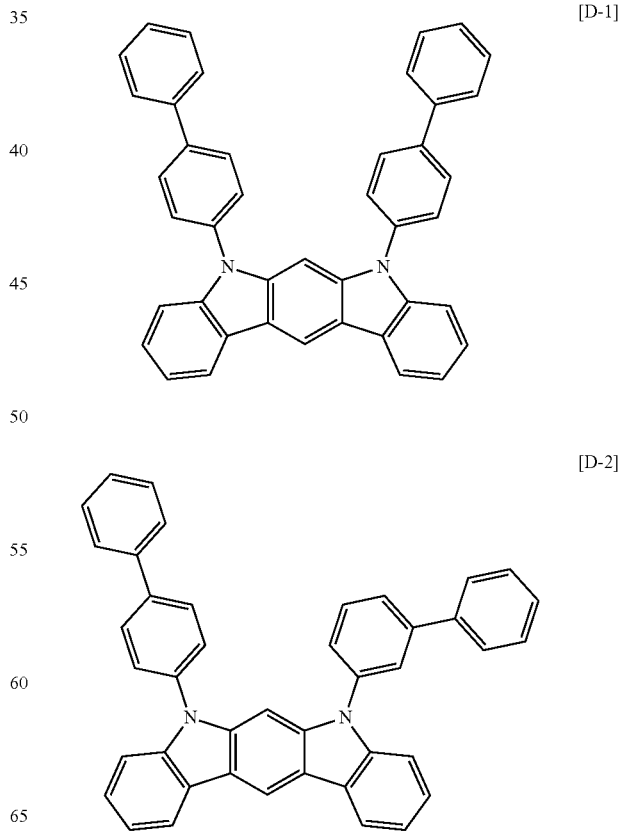

[D-3]
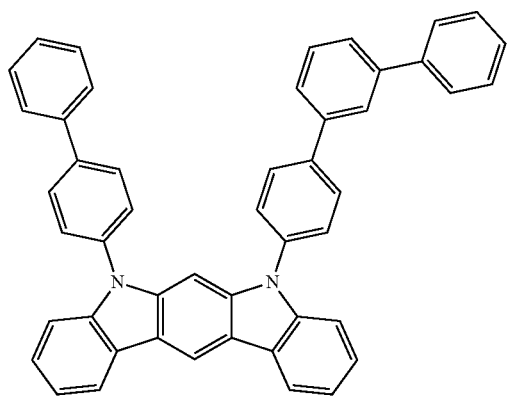
[D-4]
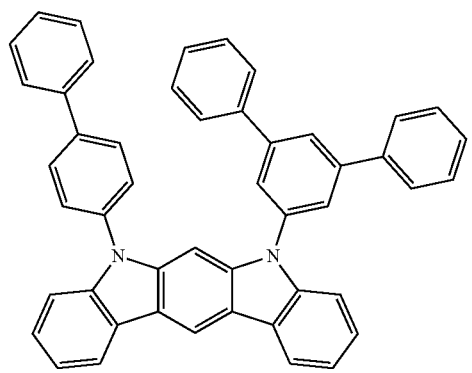
[D-5]
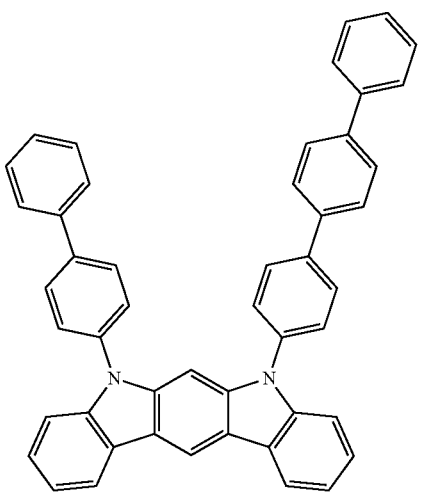
[D-6]
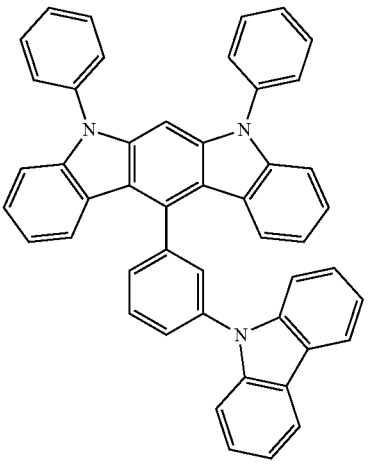
[D-7]
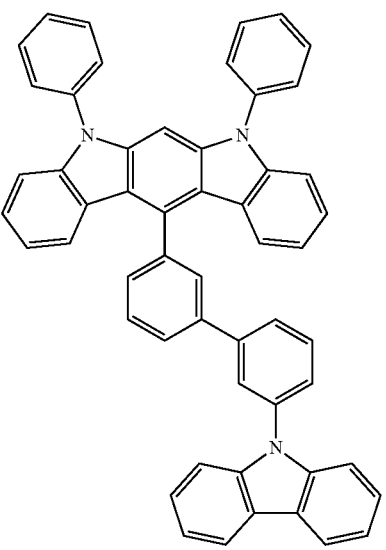
[D-8]
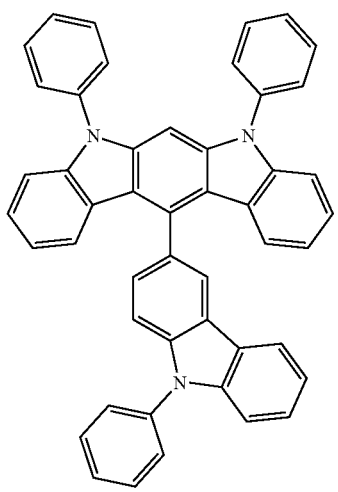

[D-9]
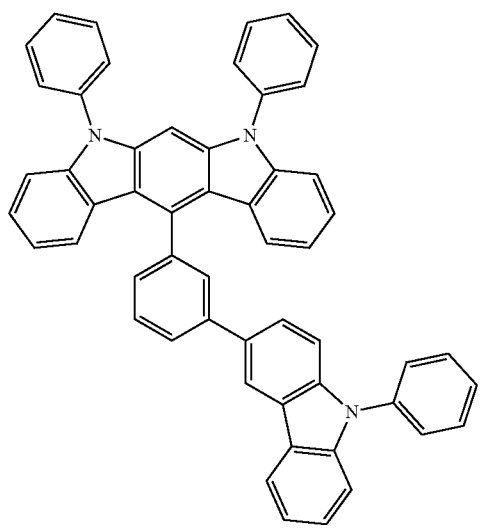
[D-10]
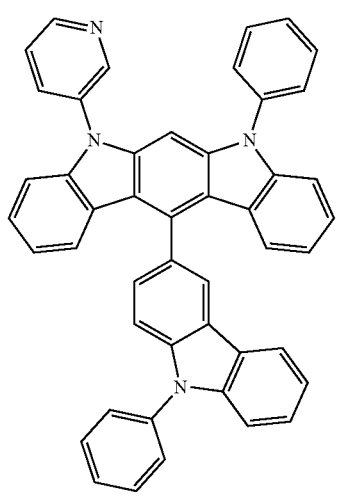
[D-11]
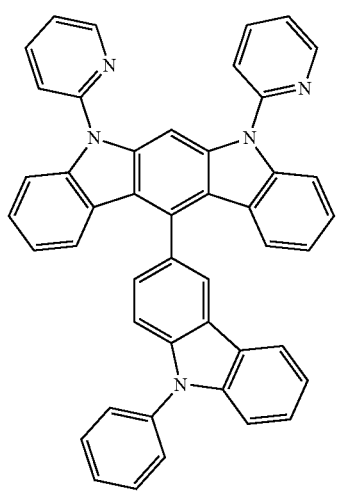
[D-12]
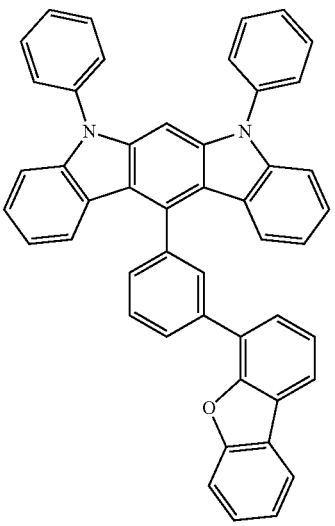
[D-13]
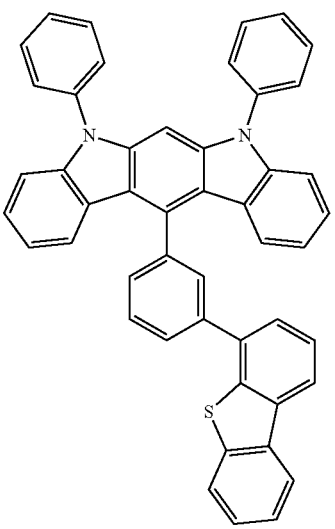
[D-14]
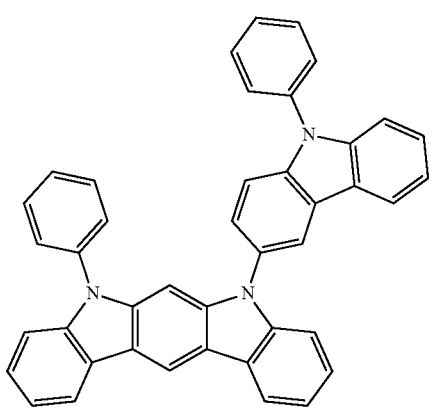

-continued
[D-15]
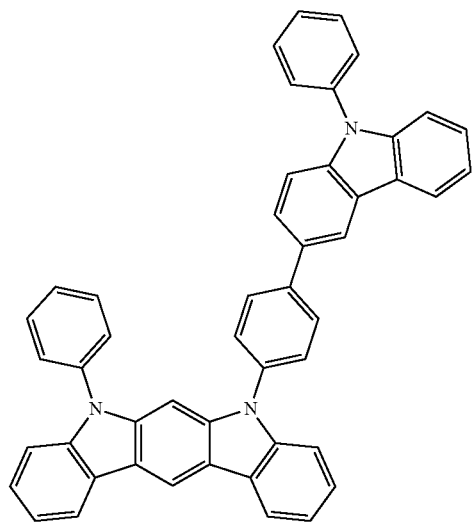
[D-16]
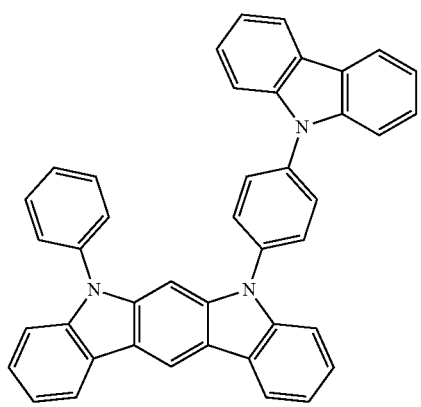
[D-17]
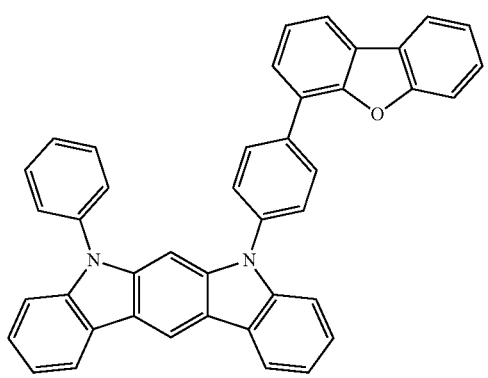
-continued
[D-18]
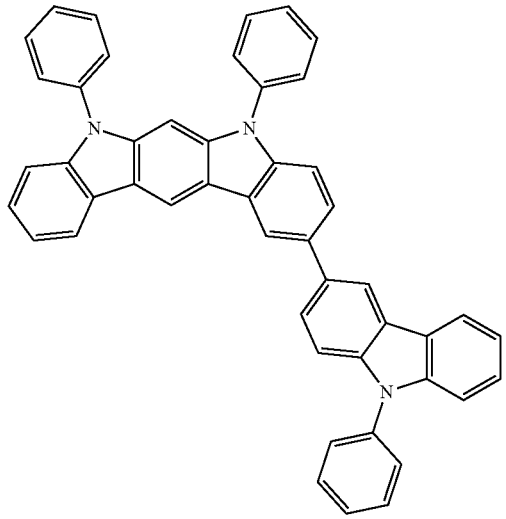
[D-19]
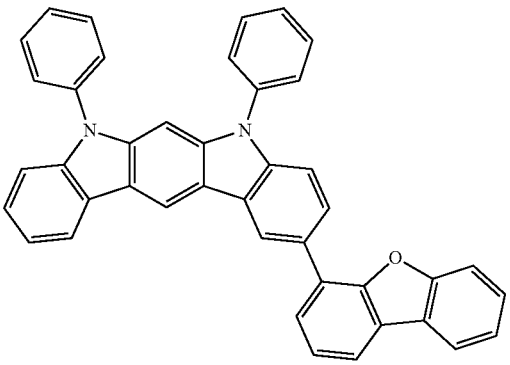
[D-20]
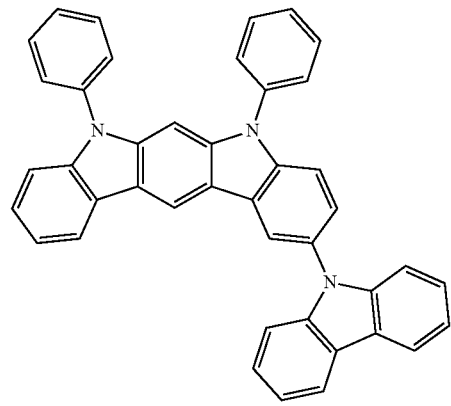

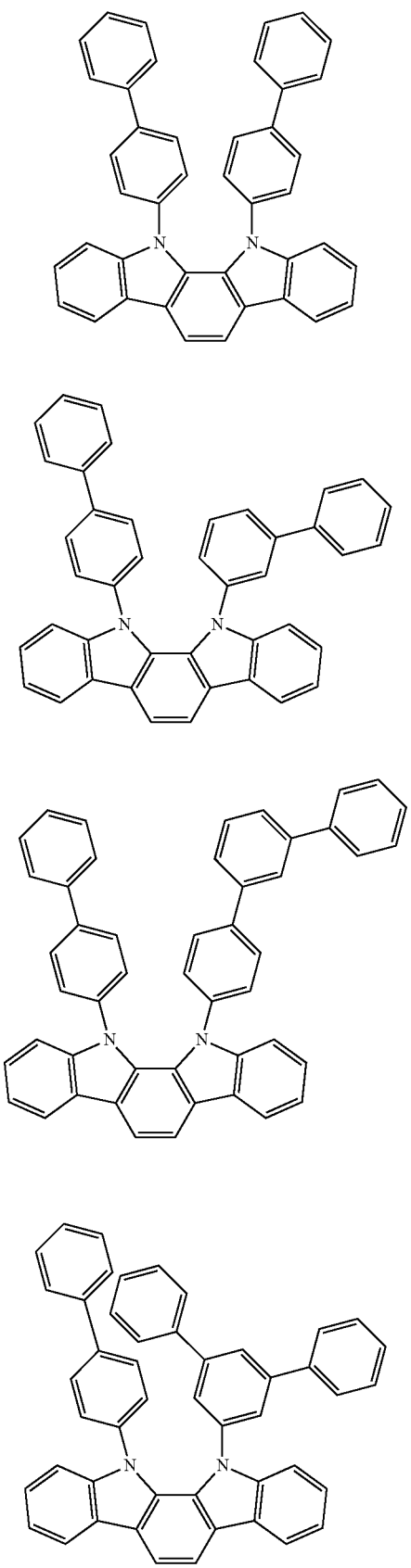
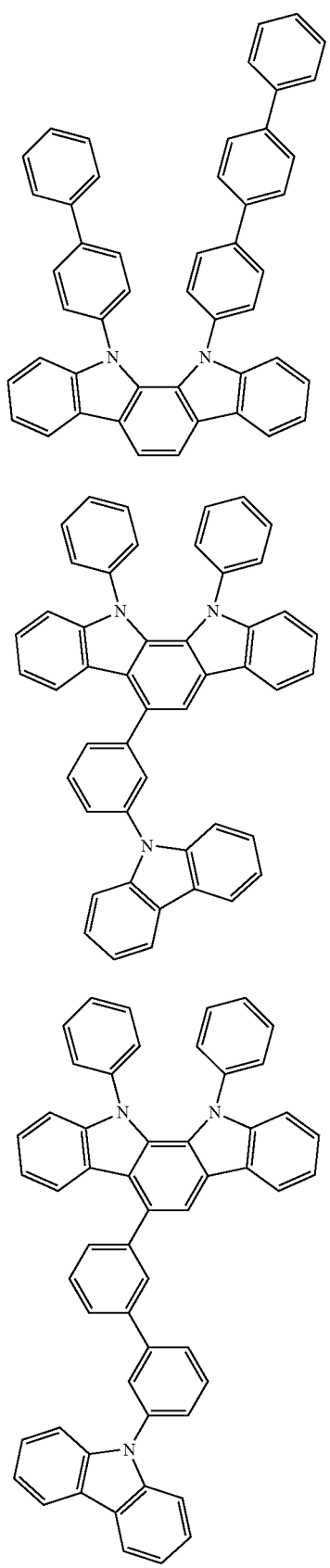

[D-28]
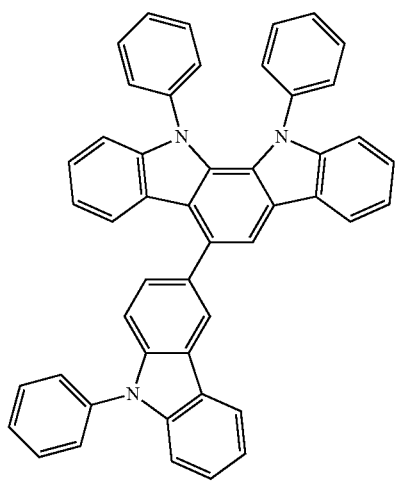
[D-29]
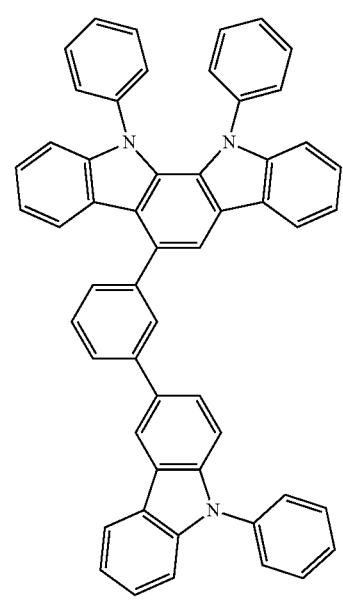
[D-30]
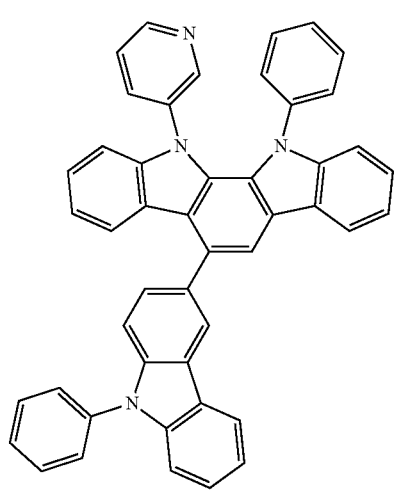
[D-31]
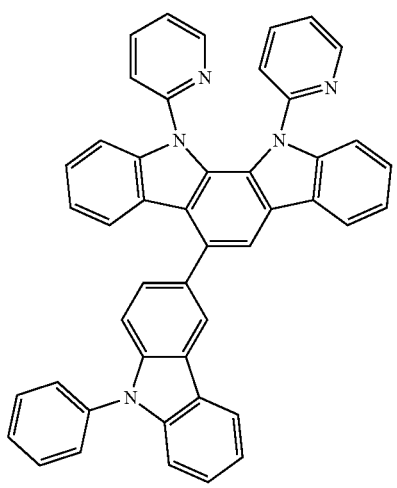
[D-32]
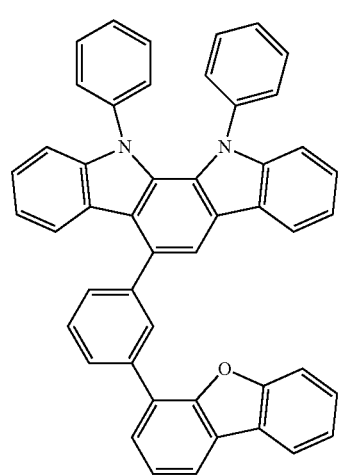
[D-33]
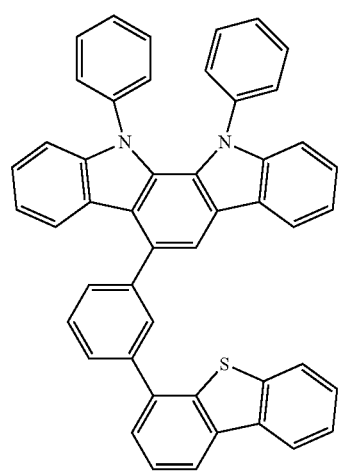

[D-34]
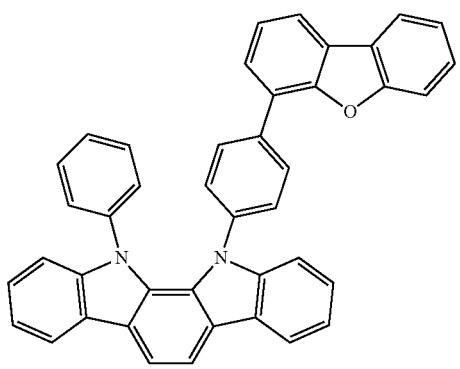
[D-35]
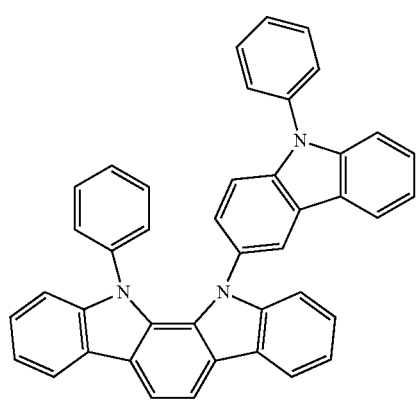
[D-36]
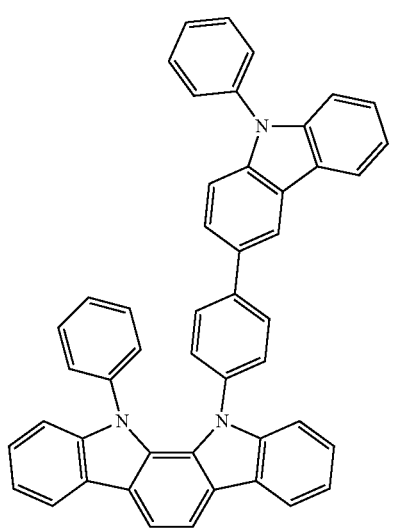
[D-37]
[D-38]
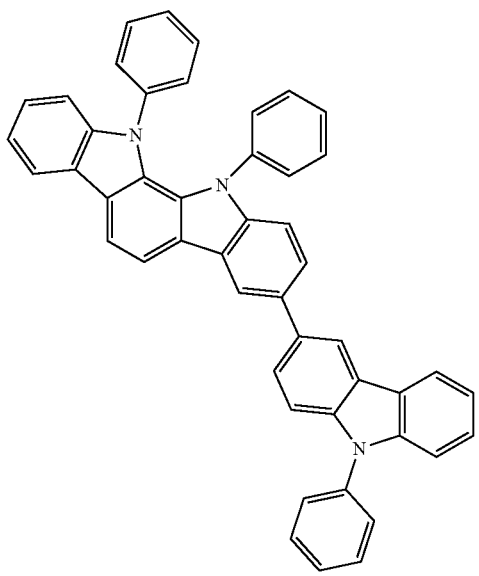
[D-39]
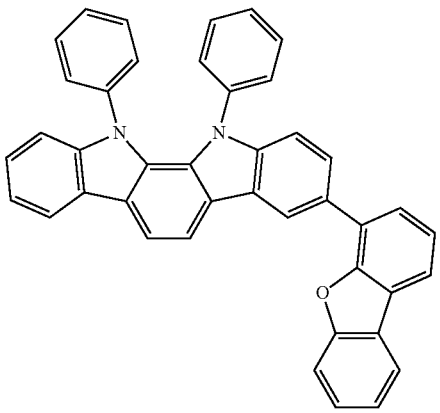

[D-40]
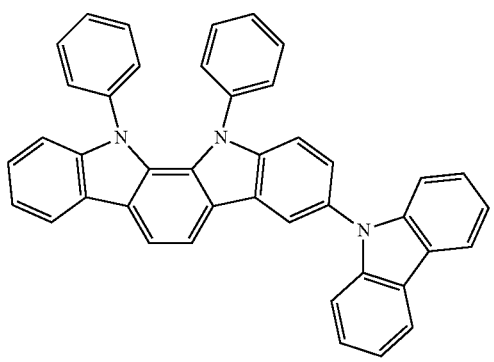
[D-43]
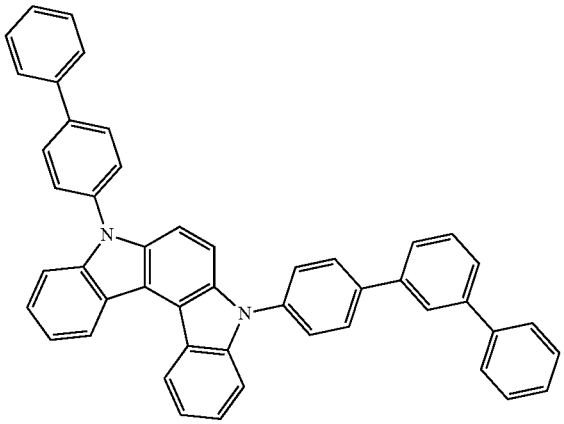
[D-41]
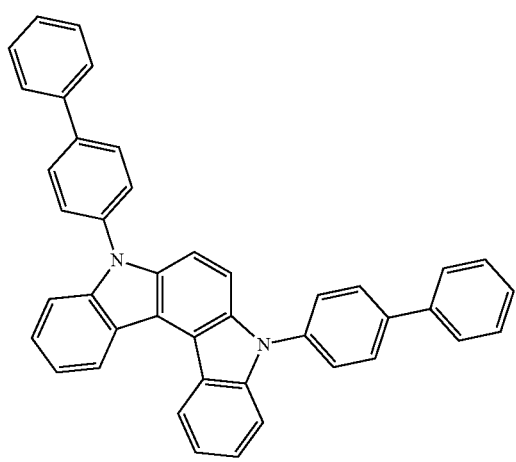
[D-44]
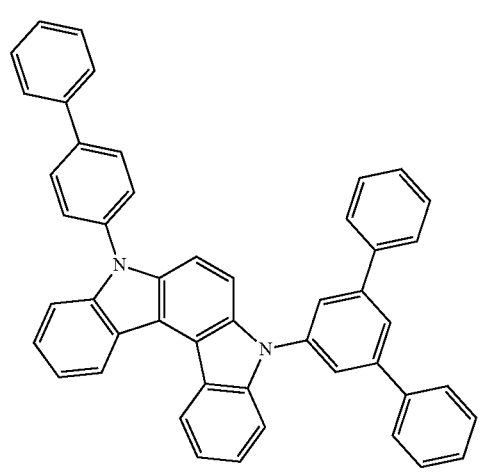
[D-42]
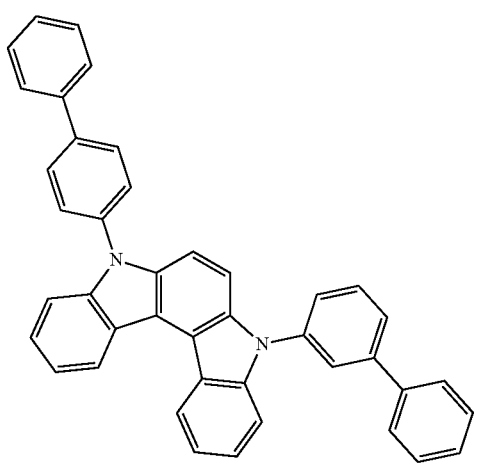
[D-45]
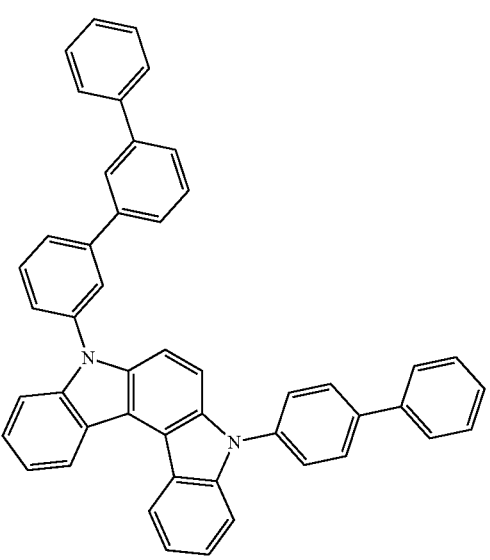

[D-46]
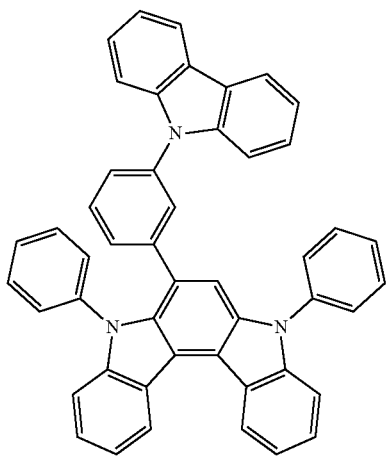
[D-47]
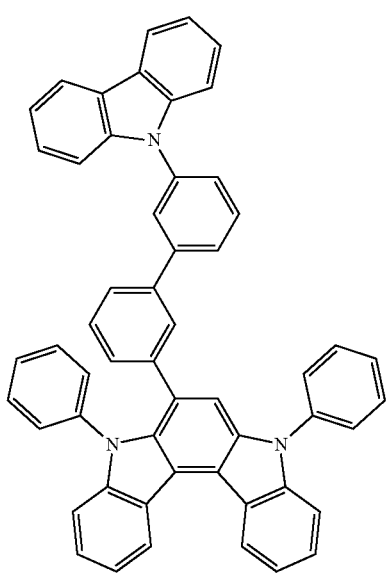
[D-48]
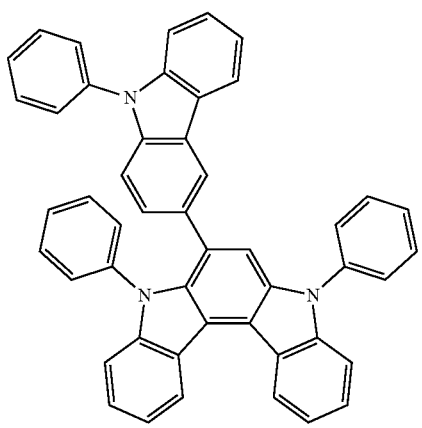
[D-49]
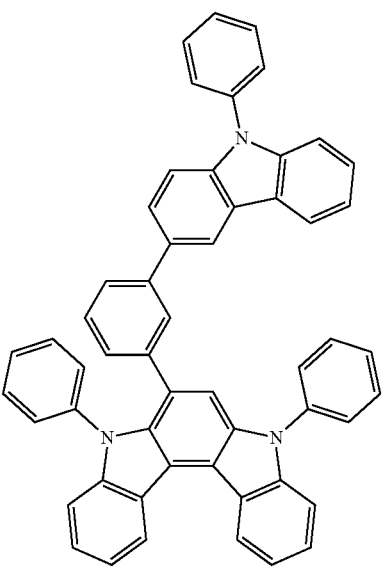
[D-50]
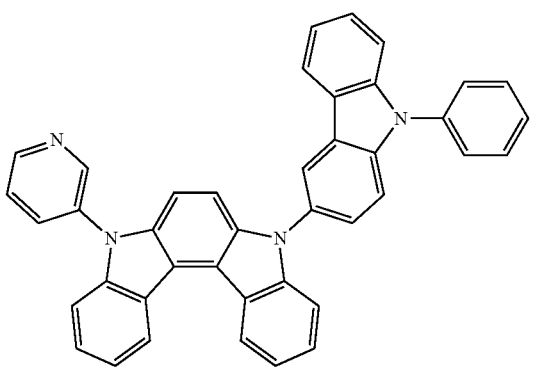
[D-51]
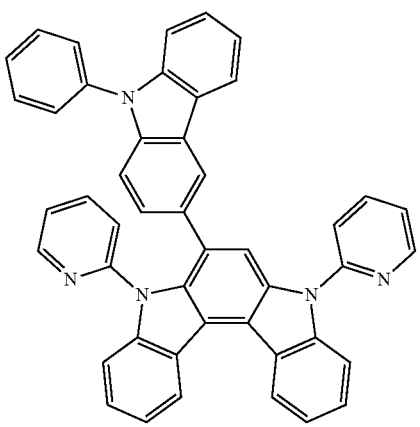

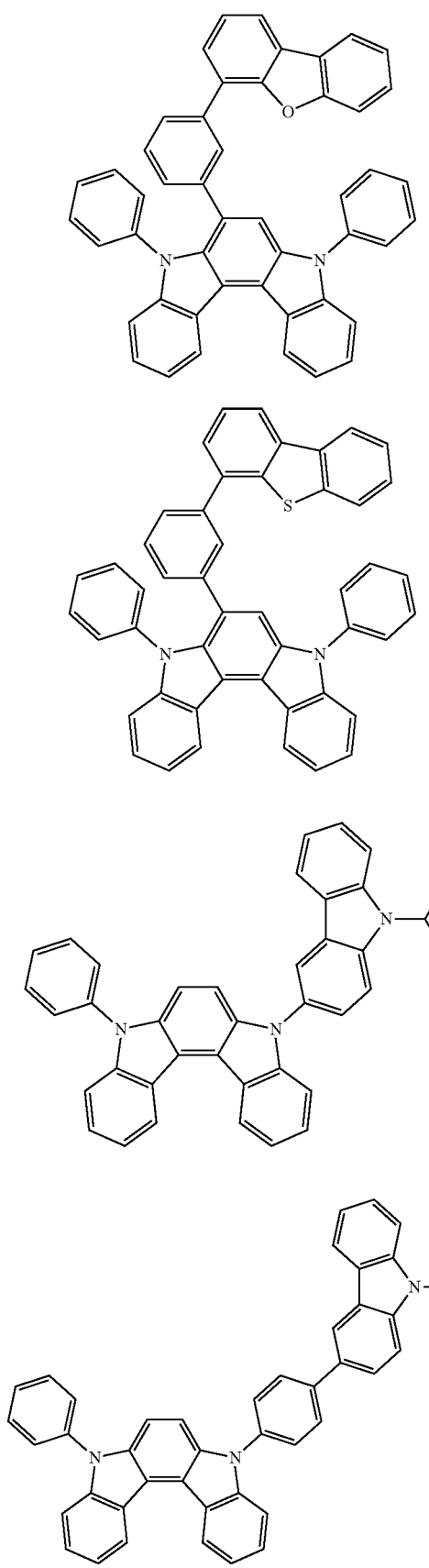

[D-59]
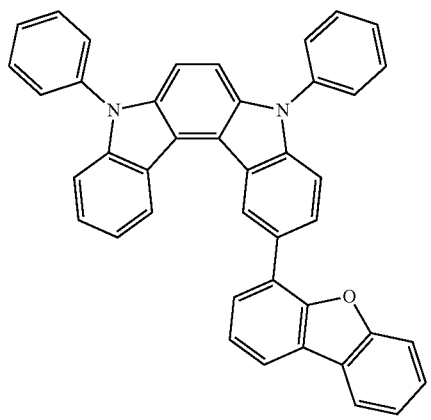
[D-62]
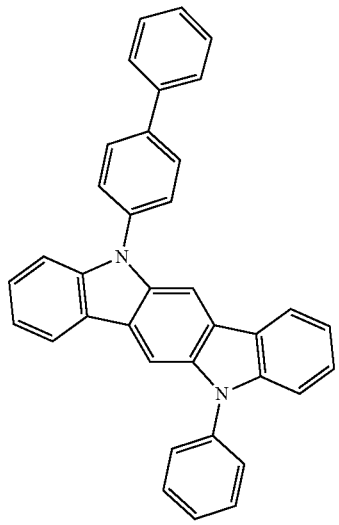
[D-60]
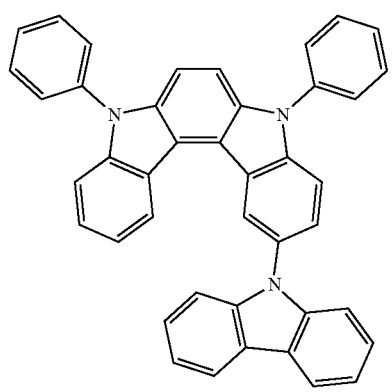
[D-63]
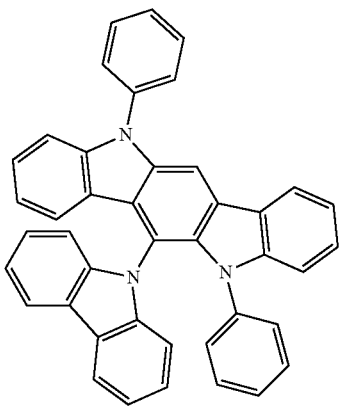
[D-61]
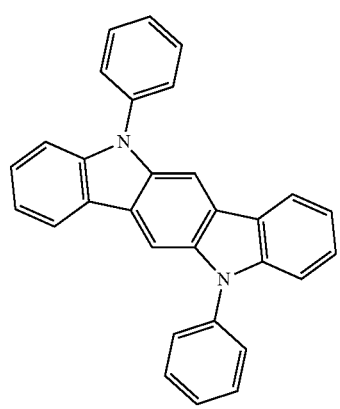
[D-64]
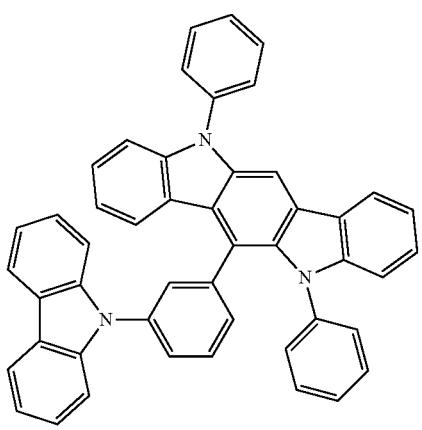

-continued
[D-65]
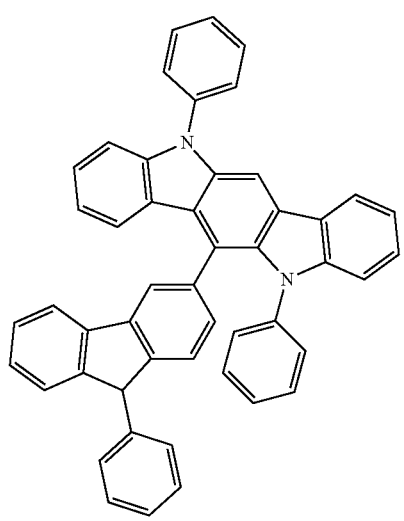
[D-66]
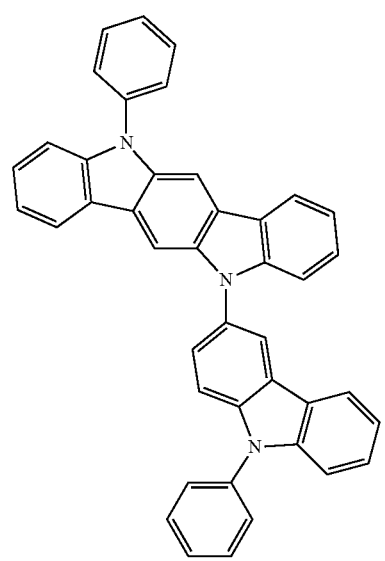
[D-67]
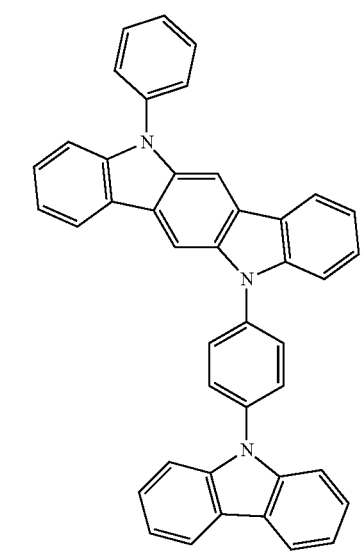
[D-68]
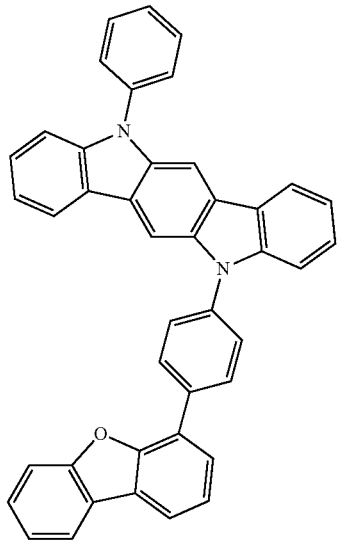
[D-69]
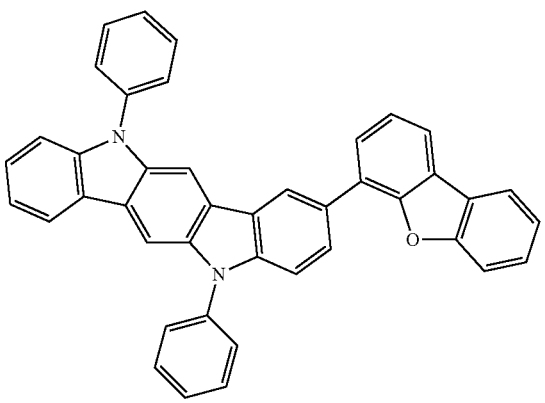
[D-70]
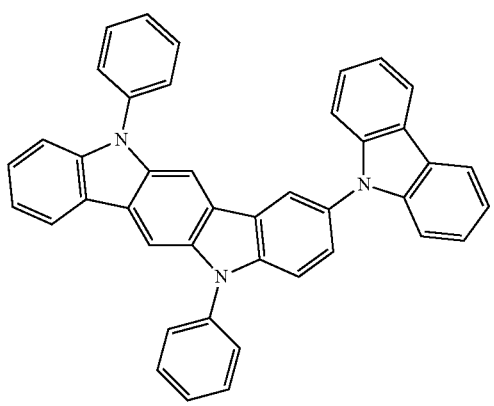

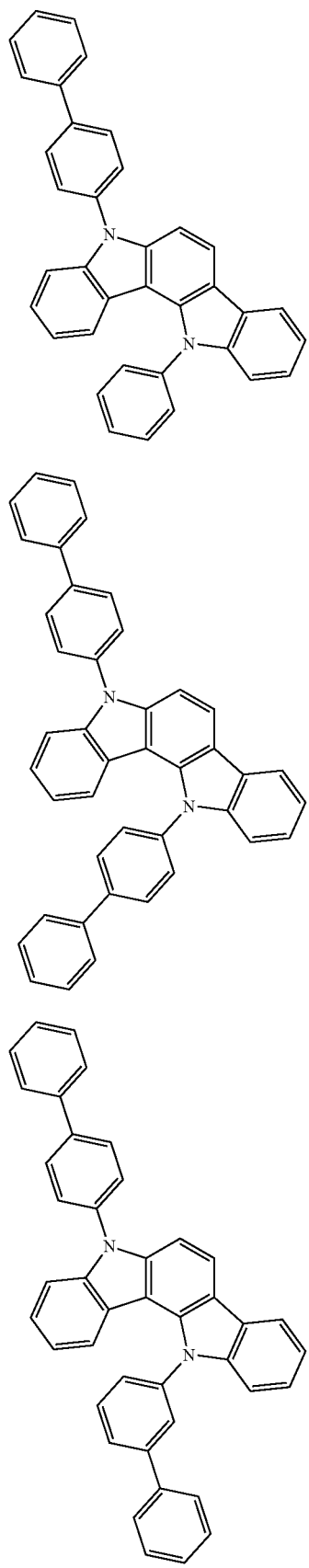
[D-71]
[D-72]
[D-73]
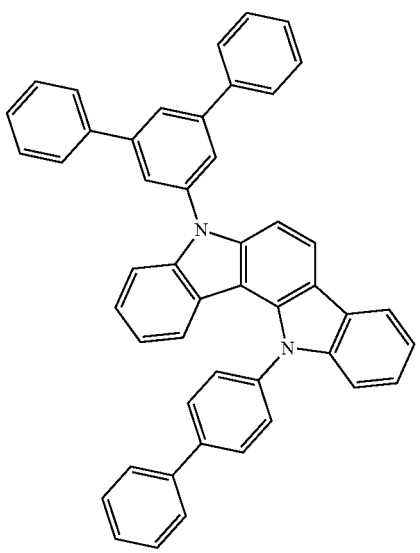
[D-74]
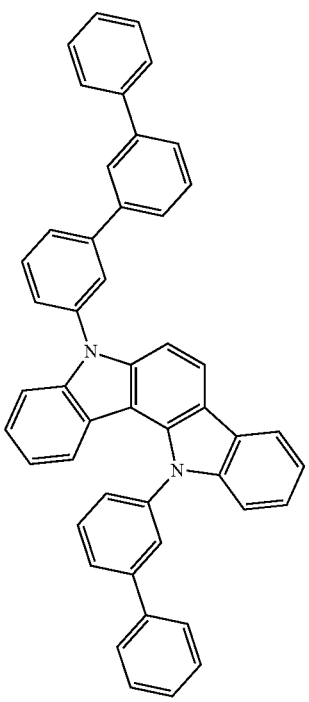
[D-75]

-continued
[D-76]
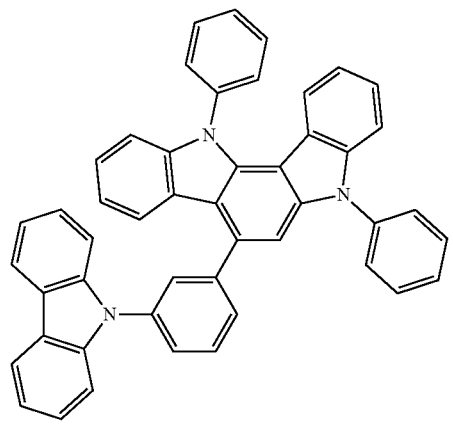
[D-77]
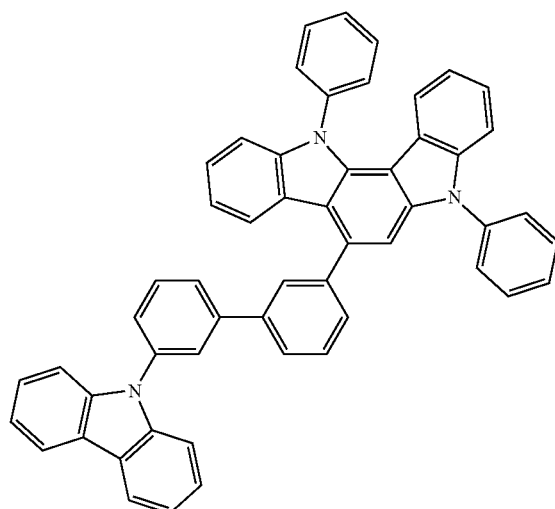
[D-78]
[D-79]
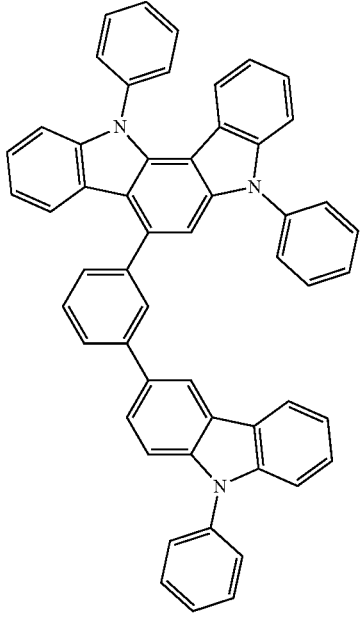
[D-80]
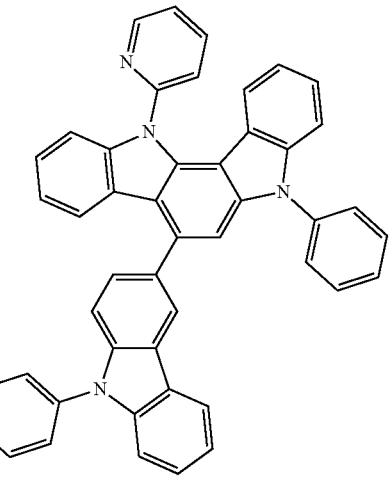
[D-81]
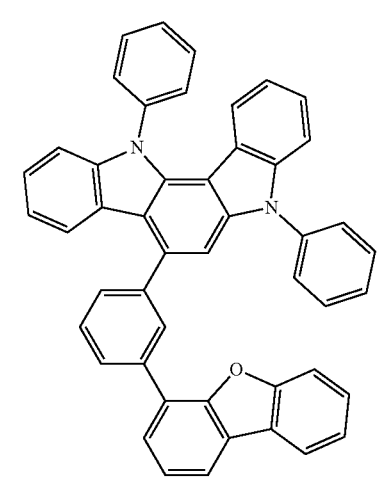

[D-82]
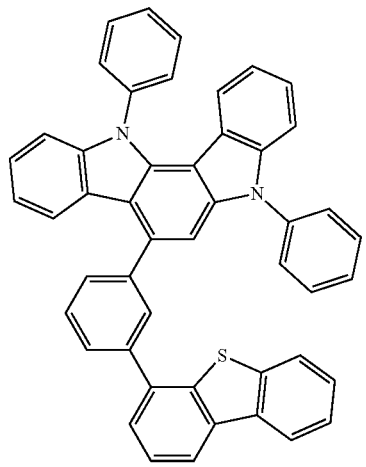
[D-85]
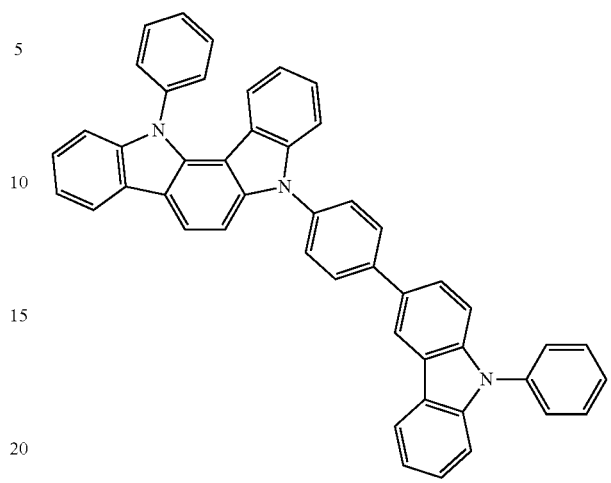
[D-83]
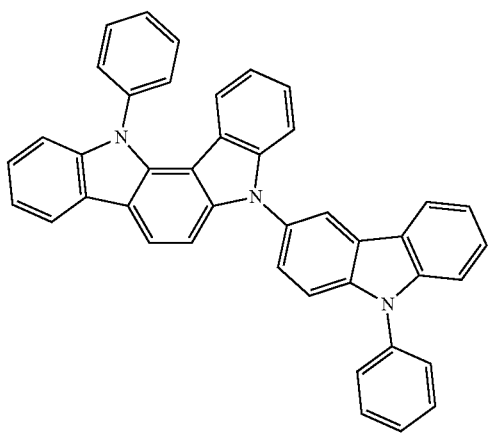
[D-86]
[D-84]
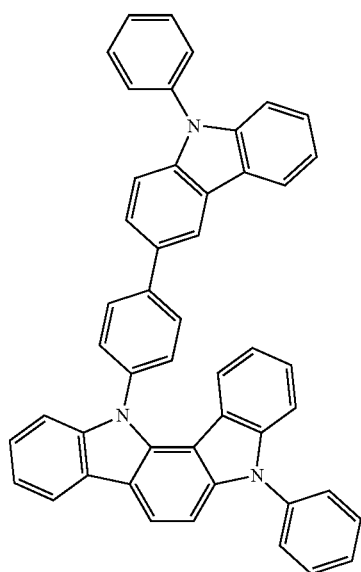
[D-87]

[D-88]
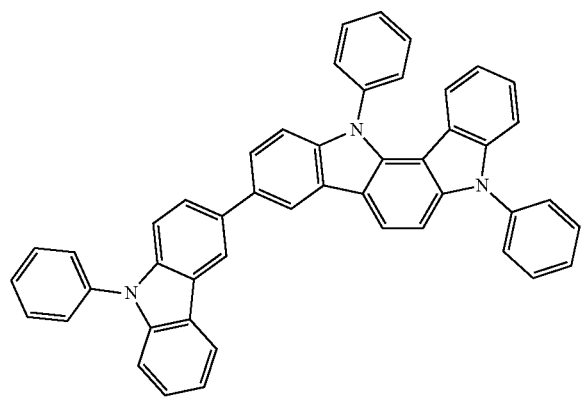
[D-91]
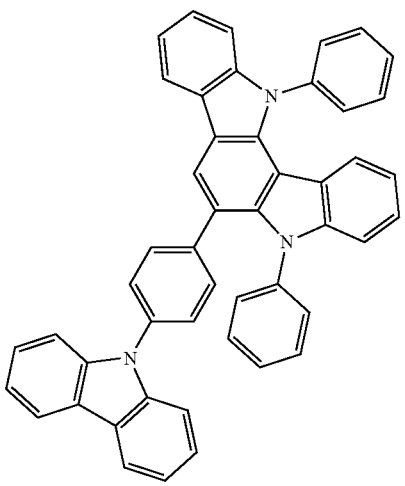
[D-89]
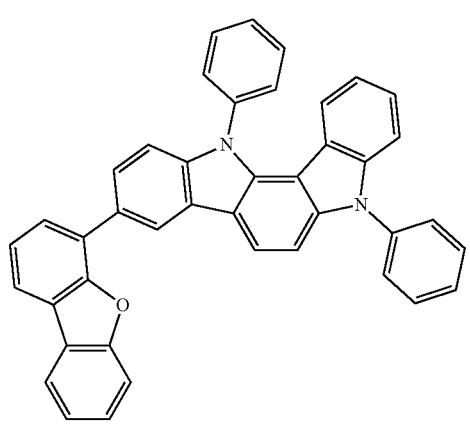
[D-92]
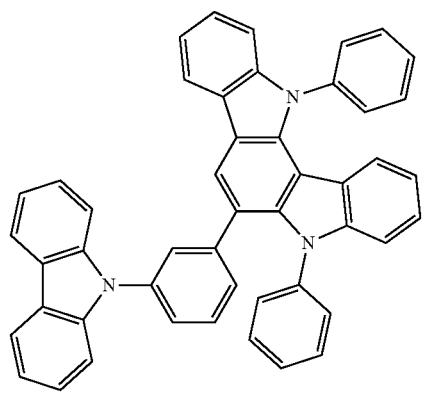
[D-90]
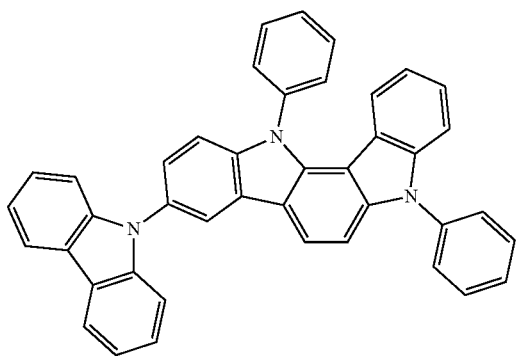
[D-93]
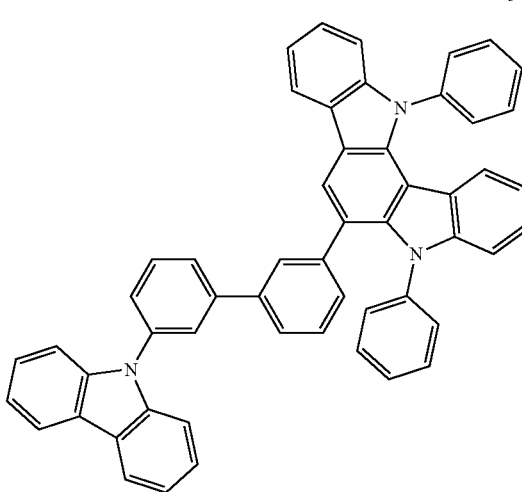

[D-94]

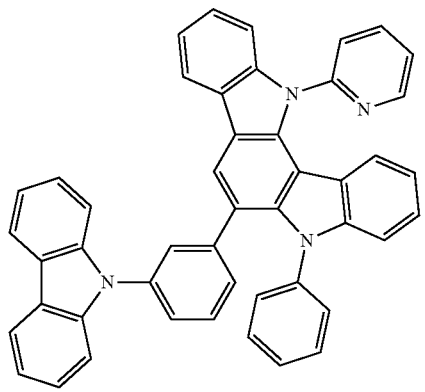

[D-95]

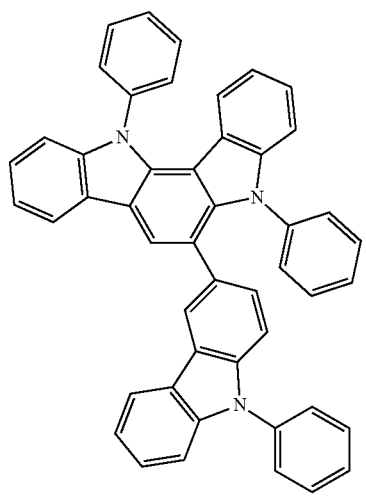

[D-96]

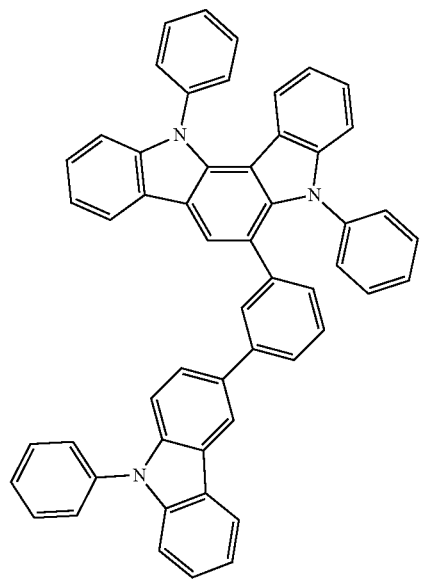

[D-97]

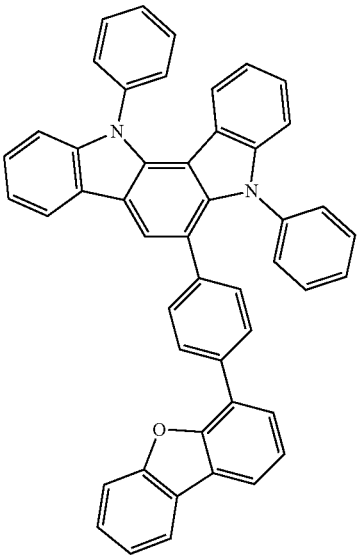

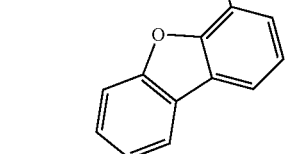

[D-98]

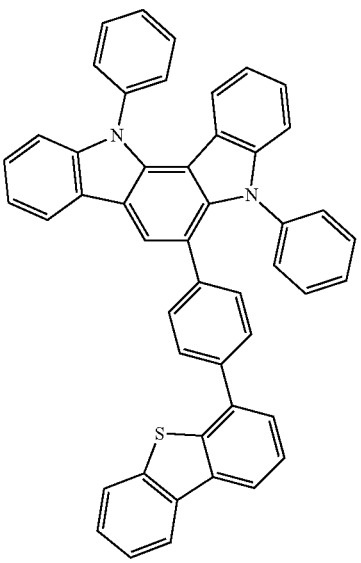

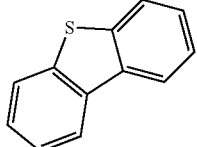

The first host and the second host may be applied as a form of a composition.

In an example embodiment of the present invention, the first host applied to the composition may be represented by Chemical Formula 1-3a and the second host may be represented by Chemical Formula 2B.

$Z^1$ to $Z^3$ of Chemical Formula 1-3a may be all N, $R^1$ is a substituted or unsubstituted C6 to C20 aryl group, a substituted or unsubstituted dibenzofuranyl group, or a substituted or unsubstituted dibenzothiophenyl group, and $L^1$ may be a single bond or a meta-phenylene group, and $Y^1$ and $Y^2$ of Chemical Formula 2B may independently be a substituted or unsubstituted C6 to C20 aryl group, and $L^3$ and $L^4$ may independently be a substituted or unsubstituted C6 to C20 arylene group.

The first host and the second host in the present invention may be a known phosphorescent dopant that is an organometal compound including one of Ir, Pt, Os, Ti, Zr, Hf, Eu, Tb, Tm, Fe, Co, Ni, Ru, Rh, Pd, or a combination thereof or may be mixed with an organometal compound represented by Chemical Formula 401. However, these are exemplified, and a dopant that exhibit excellent effect by combining the composition of the first host and the second host according to the present invention is a phosphorescent dopant represented by Chemical Formula 4.

<Chemical Formula 401>

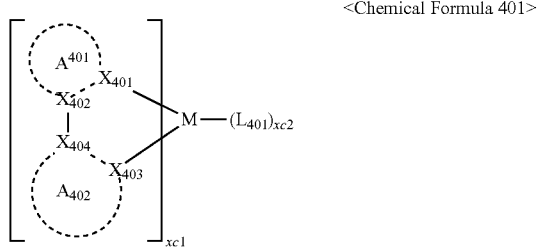

In Chemical Formula 401, M is selected from Ir, Pt, Os, Ti, Zr, Hf, Eu, Tb, and Tm; $X_{401}$ to $X_{404}$ are independently nitrogen or carbon; $A_{401}$ and $A_{402}$ rings are independently selected from a substituted or unsubstituted benzene, a substituted or unsubstituted naphthalene, a substituted or unsubstituted fluorene, a substituted or unsubstituted spirofluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; wherein "substituted" refers to replacement of at least one hydrogen of a substituent or a compound by deuterium, a halogen, a hydroxyl group, a cyano group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heterocyclic group, a C1 to C20 alkoxy group, a C1 to C10 trifluoroalkyl group, or a combination thereof; $L_{401}$ is an organic ligand; xc1 is 1, 2, or 3; and xc2 is 0, 1, 2, or 3.

$L_{401}$ may be any monovalent, divalent, or trivalent organic ligand. For example, $L_{401}$ may be selected from a halogen ligand (for example, Cl, F), diketone ligand (for example, acetylacetonate, 1,3-diphenyl-1,3-propanedionate, 2,2,6,6-tetramethyl-3,5-heptanedionate, or hexafluoroacetonate), carboxylic acid ligand (for example, picolinate, dimethyl-3-pyrazolecarboxylate, benzoate), a carbon monoxide ligand, an isonitrile ligand, a cyano ligand, and a phosphorus ligand (for example, phosphine, phosphite), but is not limited thereto.

$Q_{401}$ to $Q_{407}$, $Q_{411}$ to $Q_{417}$, and $Q_{421}$ to $Q_{427}$ may independently be selected from hydrogen, a C1 to C60 alkyl group, a C2 to C60 alkenyl group, a C6 to C60 aryl group, and a C2 to C60 heteroaryl group.

When $A_{401}$ of Chemical Formula 401 has two or more substituents, they may be combined with two or more substituents of $A_{401}$ to form a saturated or unsaturated ring.

When $A_{402}$ of Chemical Formula 401 has two or more substituents, they may be combined with two or more substituents of $A_{402}$ to form a saturated or unsaturated ring.

When xc1 of Chemical Formula 401 is two or more, a plurality of ligands

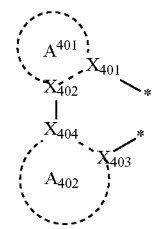

of Chemical Formula 401 may be the same or different. When xc1 of Chemical Formula 401 is two or more, $A_{401}$ and $A_{402}$ may be independently linked with $A_{401}$ and $A_{402}$ of adjacent other ligand directly or by a linking group (for example, C1 to C5 alkylene group, —N(R')— (wherein, R' is a C1 to C10 alkyl group or a C6 to C20 aryl group), or —C(=O)—).

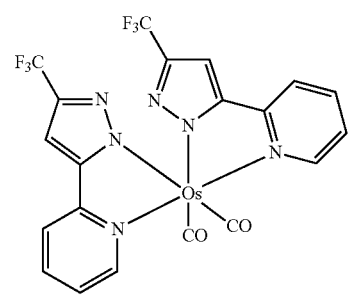

PD70

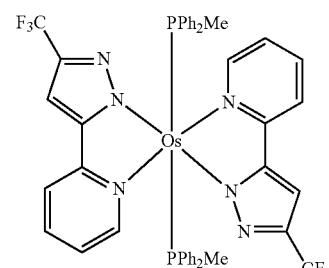

PD71

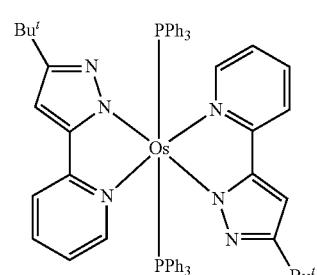

PD72

-continued

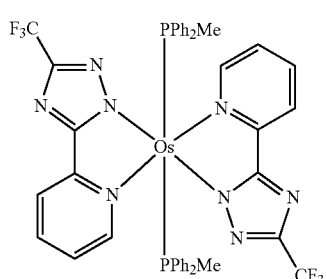
PD73

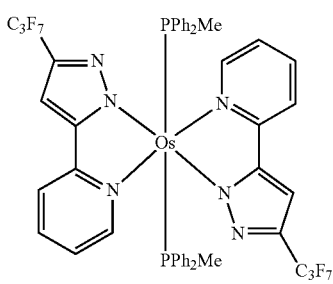
PD74

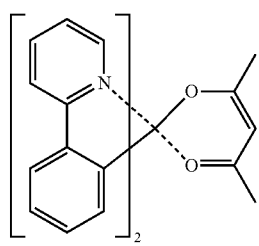
PD75

That is, in an example embodiment of the present invention, an organometal compound represented by Chemical Formula 4 is used.

[Chemical Formula 4]

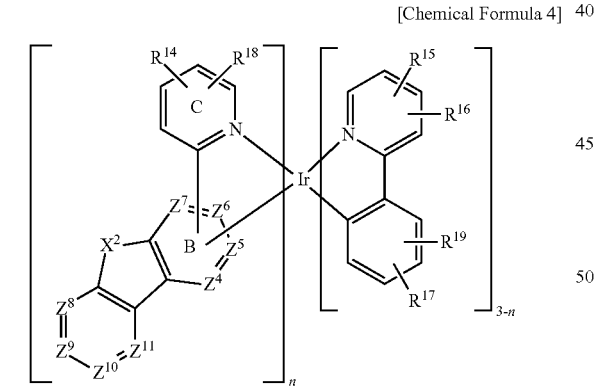

In Chemical Formula 4, $Z^4$ to $Z^{11}$ are independently N, C or $CR^c$, the ring C is bound to the ring B through a C—C bond, iridium is bound to the ring B through a Ir—C bond, $X^2$ is O or S, $R^c$ and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is an integer ranging from 1 to 3.

The composition including the first and second hosts may be combined with the phosphorescent dopant including a dibenzofuranyl group, a dibenzothiophenyl group, or derivative groups thereof including at least one N to secure a combination/matching advantage of packing of host and dopant materials, an energy transport, and the like and thus obtain characteristics of a low driving, a long life-span, and high efficiency.

In an example embodiment of the present invention, in Chemical Formula 4, one of $Z^4$ to $Z^{11}$ may be preferably N, and two, three, or four may be N.

The phosphorescent dopant may be for example represented by one of Chemical Formula 4-1 to Chemical Formula 4-6.

[Chemical Formula 4-1]

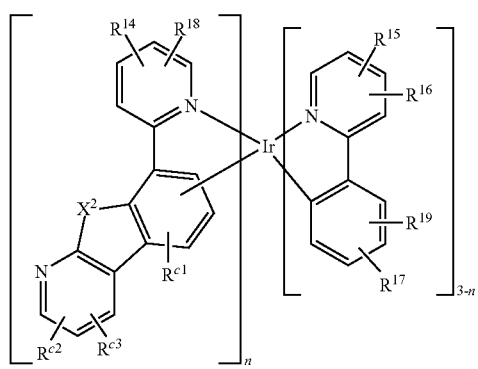

[Chemical Formula 4-2]

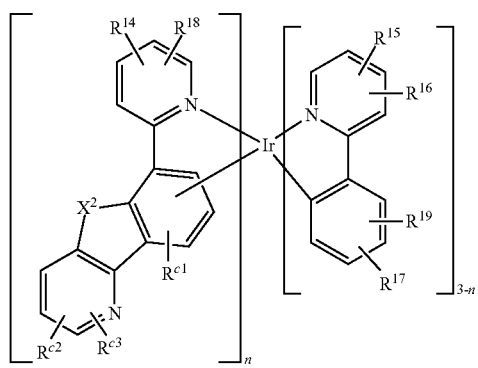

[Chemical Formula 4-3]

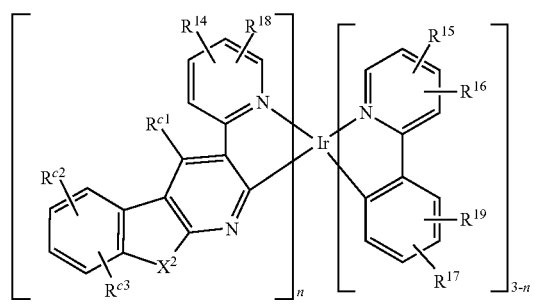

[Chemical Formula 4-4]

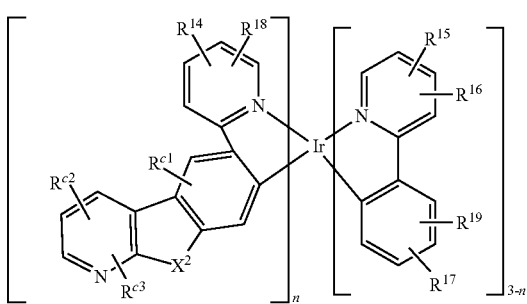

[Chemical Formula 4-5]

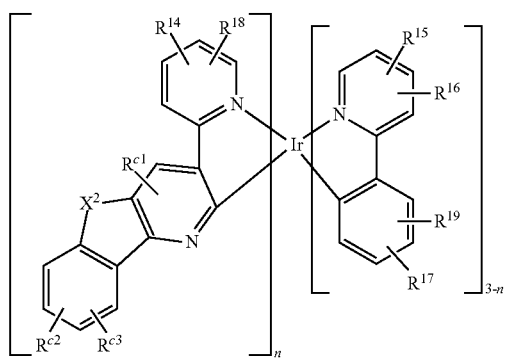

[Chemical Formula 4-6]

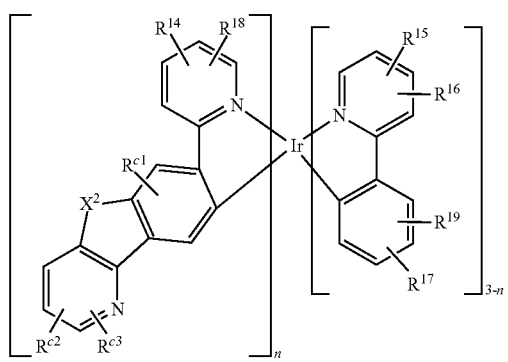

In Chemical Formula 4-1 to Chemical Formula 4-6, $X^2$, $R^{14}$ to $R^{19}$ and n are the same as described above, and $R^{c1}$, $R^{c2}$, and $R^{c3}$ are the same as.

In a specific example embodiment of the present invention, $R^c$, $R^{c1}$, $R^{c2}$, $R^{c3}$, and $R^{14}$ to $R^{19}$ may independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C20 aryl group, for example $R^c$, $R^{c1}$, $R^{c2}$, $R^{c3}$ and $R^{14}$ to $R^{19}$ may independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C12 aryl group, and preferably $R^c$, $R^{c1}$, $R^{c2}$, $R^{c3}$ and $R^{14}$ to $R^{19}$ may independently be hydrogen, deuterium, a halogen, a silyl group that is substituted or unsubstituted with deuterium or a halogen, a methyl group that is substituted or unsubstituted with deuterium or a halogen, an isopropyl group that is substituted or unsubstituted with deuterium or a halogen, a tert-butyl group that is substituted or unsubstituted with deuterium or a halogen, or a silyl group that is substituted or unsubstituted with a C1 to C4 alkyl group.

The phosphorescent dopant may be for example selected from compounds of Group 3, but is not limited thereto.

[Group 3]

[E-1]

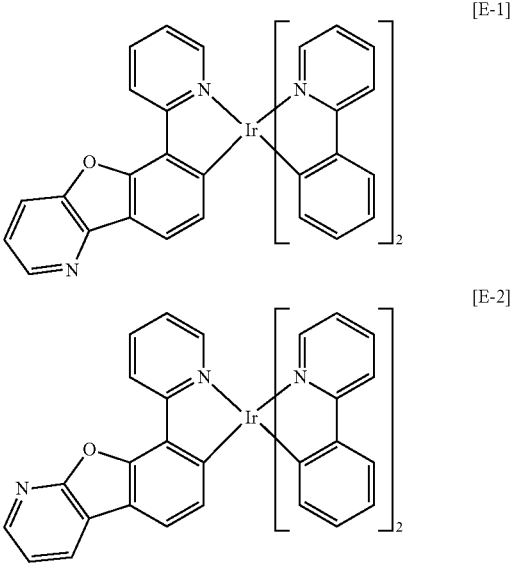

[E-2]

[E-3]

[E-4]

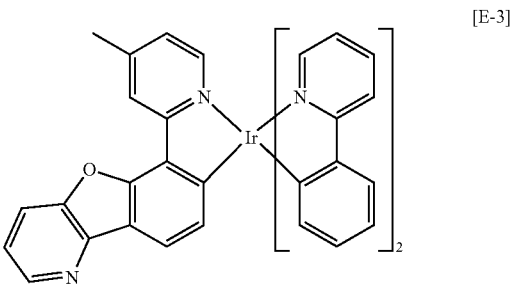

[E-5]

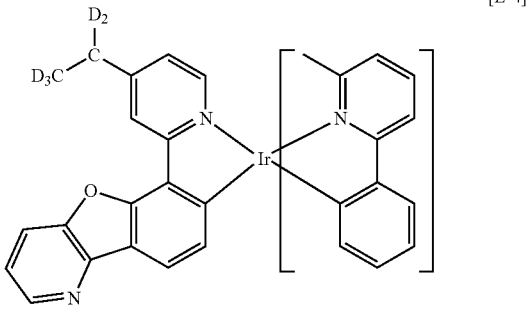

[E-6]
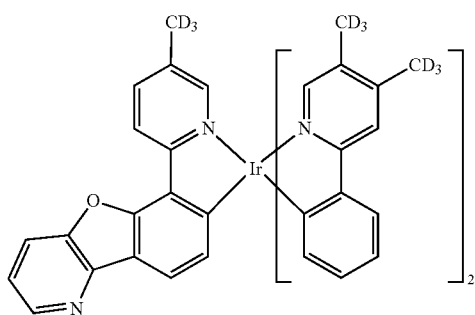
[E-7]
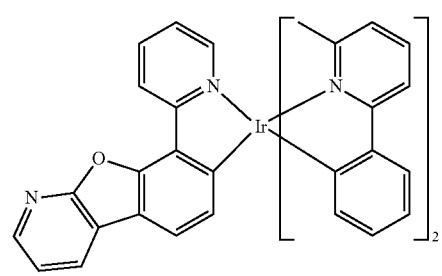
[E-8]
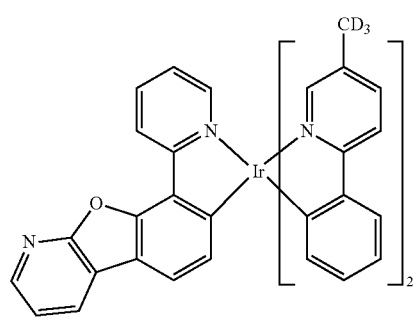
[E-9]
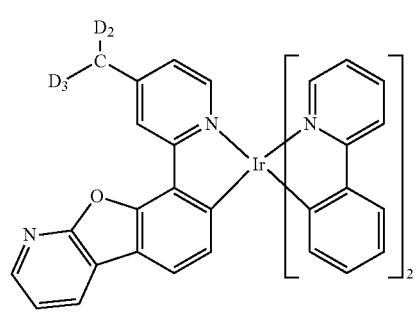
[E-10]
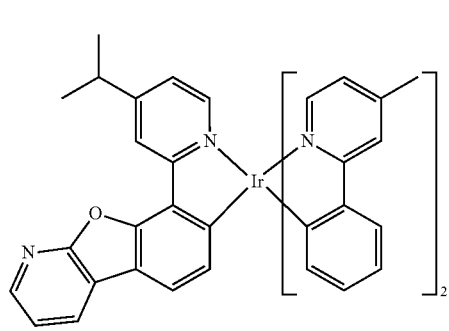
[E-11]
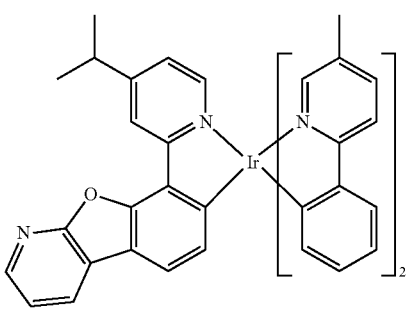
[E-12]
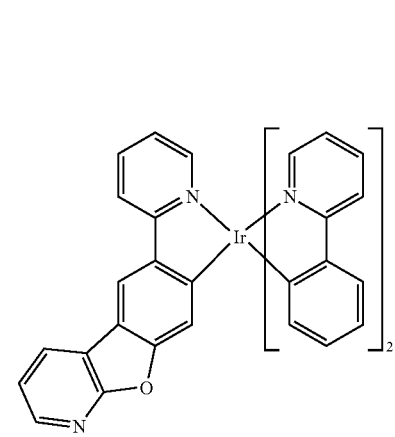
[E-13]
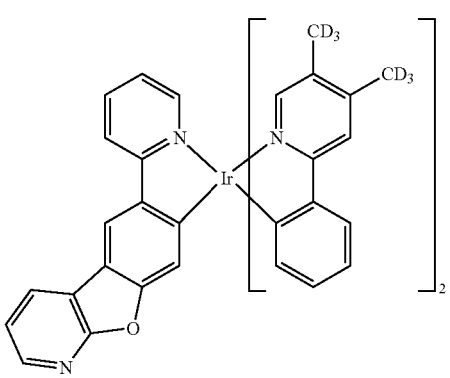
[E-14]
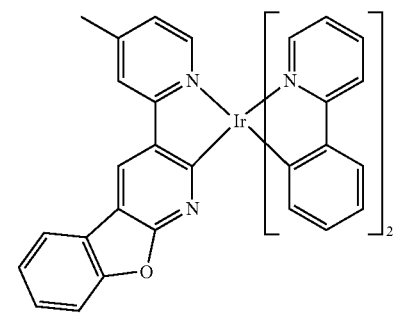

[E-15]
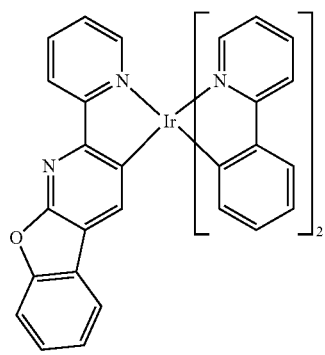
[E-16]
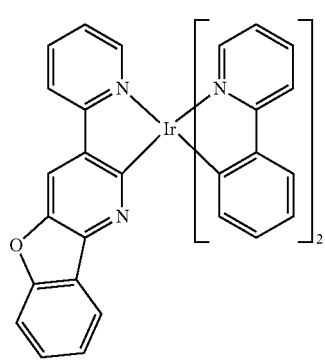
[E-17]
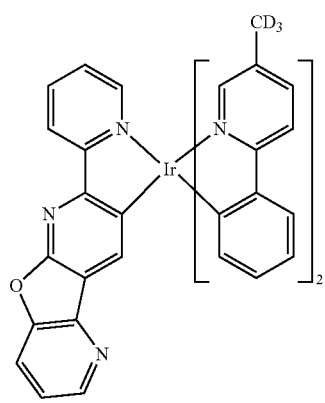
[E-18]
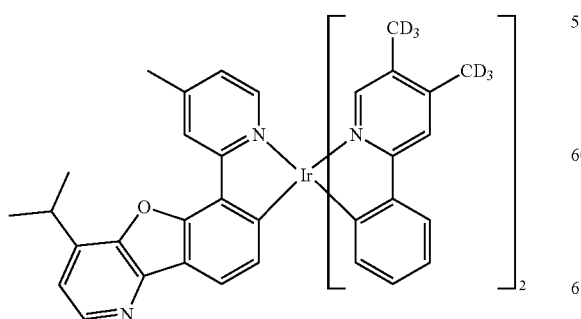
[E-19]
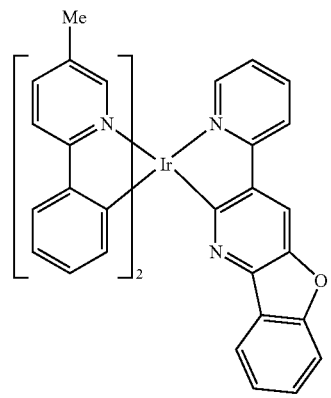
[E-20]
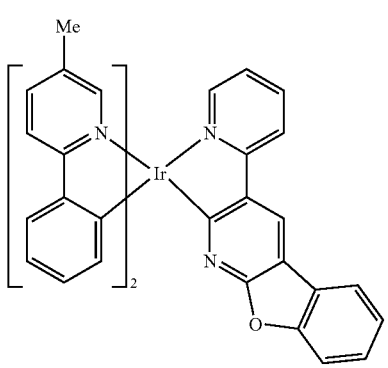
[E-21]
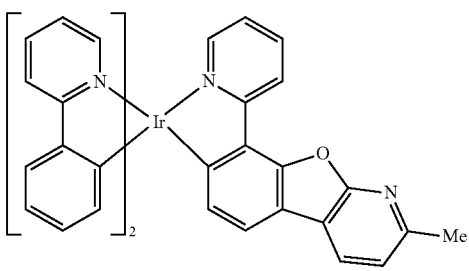
[E-22]
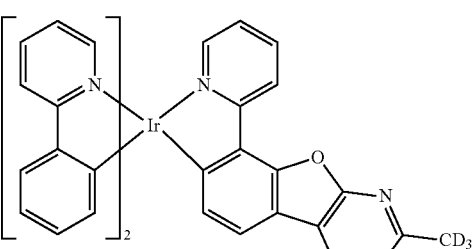
[E-23]
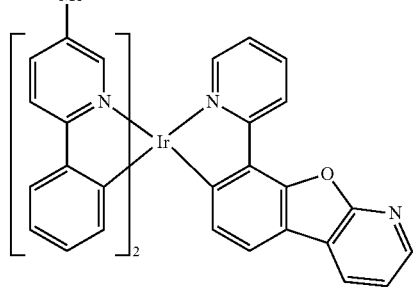

[E-24]
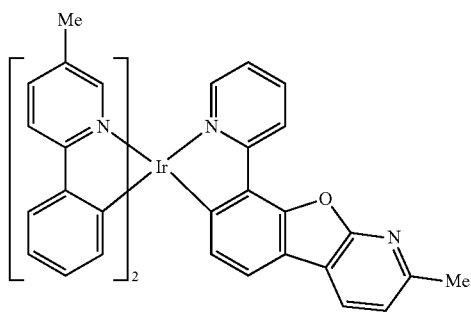
[E-25]
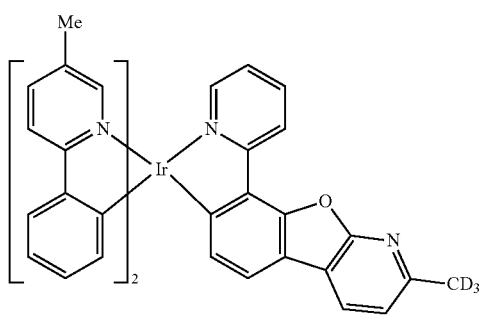
[E-26]
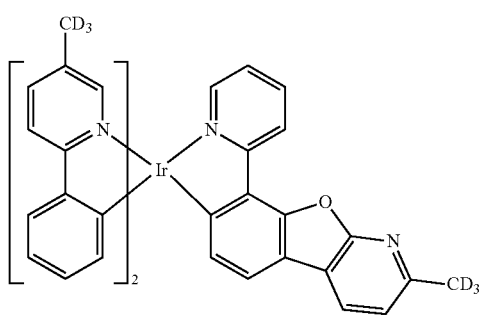
[E-27]
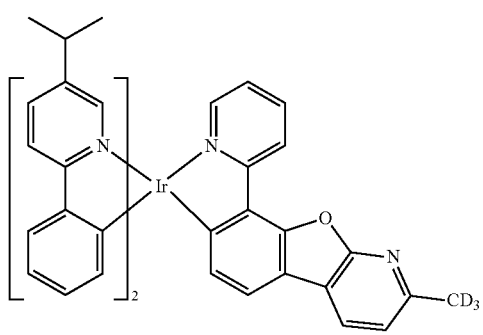
[E-28]
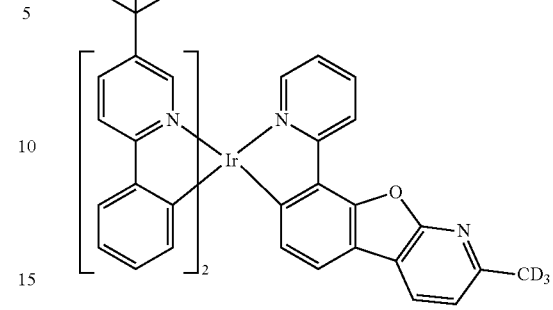
[E-29]
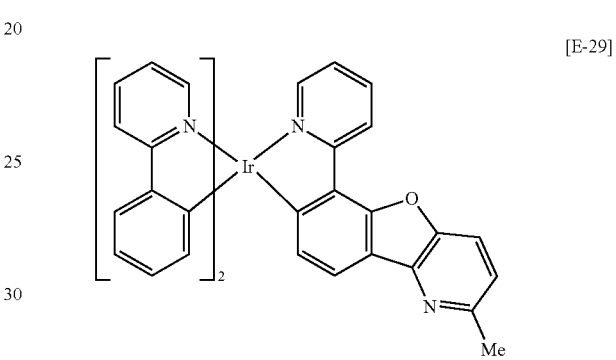
[E-30]
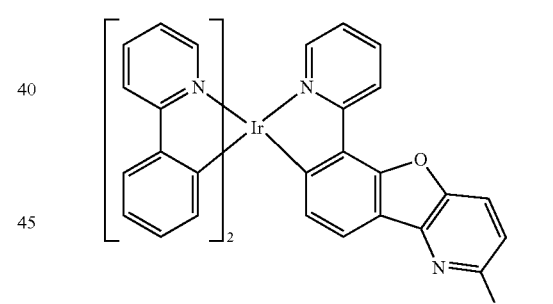
[E-31]
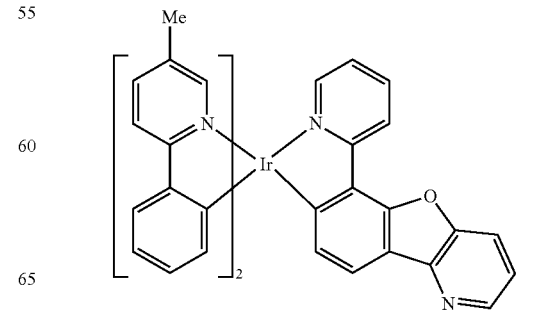

[E-32]
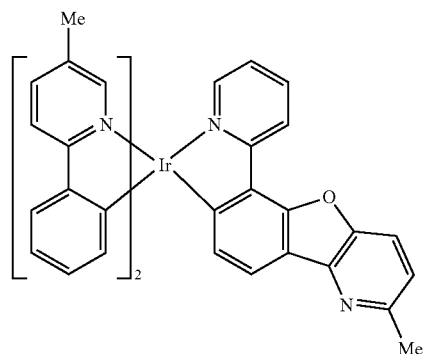
[E-36]
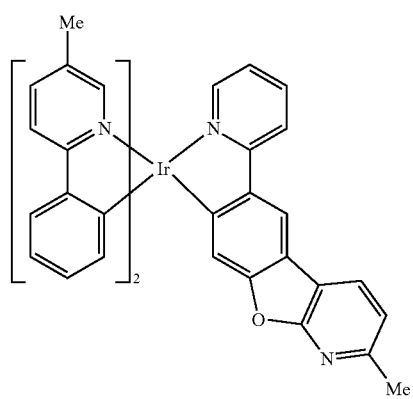
[E-33]
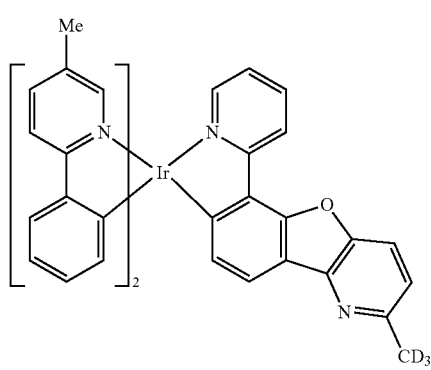
[E-37]
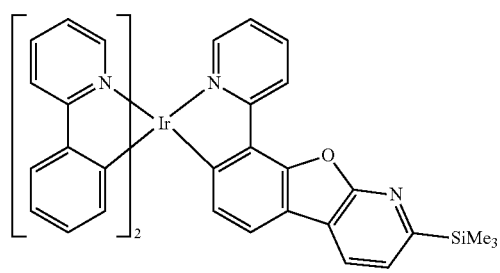
[E-34]
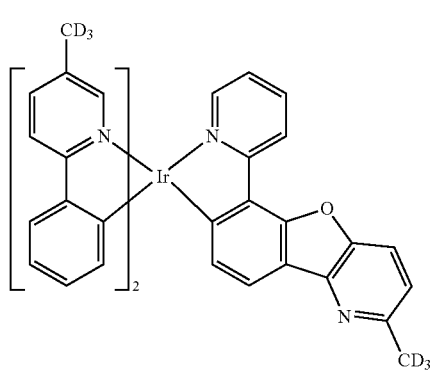
[E-38]
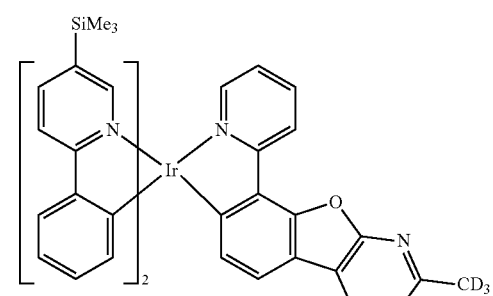
[E-35]
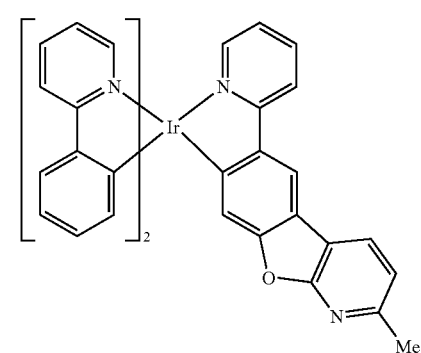
[E-39]
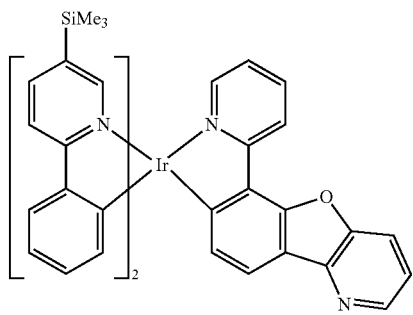

[E-40]

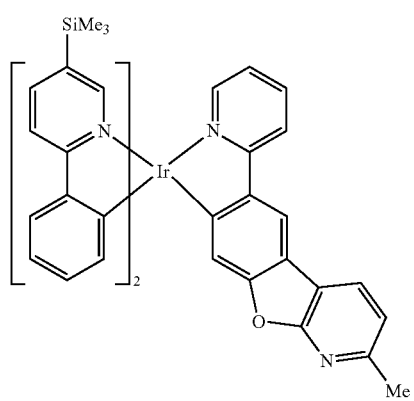

In a more preferably example embodiment of the present invention, a composition including a first host represented by Chemical Formula 1-3a, a second host represented by Chemical Formula 2B, and a phosphorescent dopant represented by Chemical Formula 4-1 may be applied to the light emitting layer, and

- $Z^1$ to $Z^3$ of Chemical Formula 1-3a may be all N, $R^1$ may be a substituted or unsubstituted C6 to C20 aryl group, a substituted or unsubstituted dibenzofuranyl group, or a substituted or unsubstituted dibenzothiophenyl group, $L^1$ may be a single bond or a meta-phenylene group,
- $Y^1$ and $Y^2$ of Chemical Formula 2B may independently be a substituted or unsubstituted C6 to C20 aryl group and $L^3$ and $L^4$ may independently be a substituted or unsubstituted C6 to C20 arylene group, and
- $R^c$, $R^{c2}$, $R^{c3}$ and $R^{14}$ to $R^{19}$ of Chemical Formula 4-1 may independently be hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C12 aryl group.

More specifically, the first host and the second host may be included in a weight ratio of 1:9 to 6:4, 2:8 to 6:4, 3:7 to 6:4, more preferably, the first host and the second host may be included in a weight ratio of 1:9 to 5:5, 2:8 to 5:5, 3:7 to 5:5, and the most preferably the first host and the second host may be included in a weight ratio of 4:6 to 5:5.

The phosphorescent dopant may be included in an amount of about 0.1 wt % to 15 wt %, preferably 1 wt % to 15 wt %, and more preferably 5 wt % to 15 wt % based on 100 wt % of the composition of the first host and second host. For example, the first host and the second host may be included in a weight ratio of 3:7 and the phosphorescent dopant may be included in an amount of 5 wt % to 15 wt % based on 100 wt % of the composition of the first host and second host.

The organic light emitting diode may be applied to an organic light emitting diode (OLED) display.

Embodiments of the Invention

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.

The compound as one specific examples of the present invention was synthesized through the following steps.

Preparation of First Host

Synthesis Example 1: Synthesis of Compound B-1

[Reaction Scheme 1]

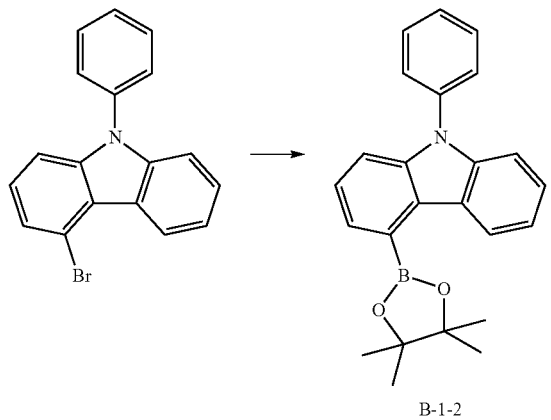

B-1-2

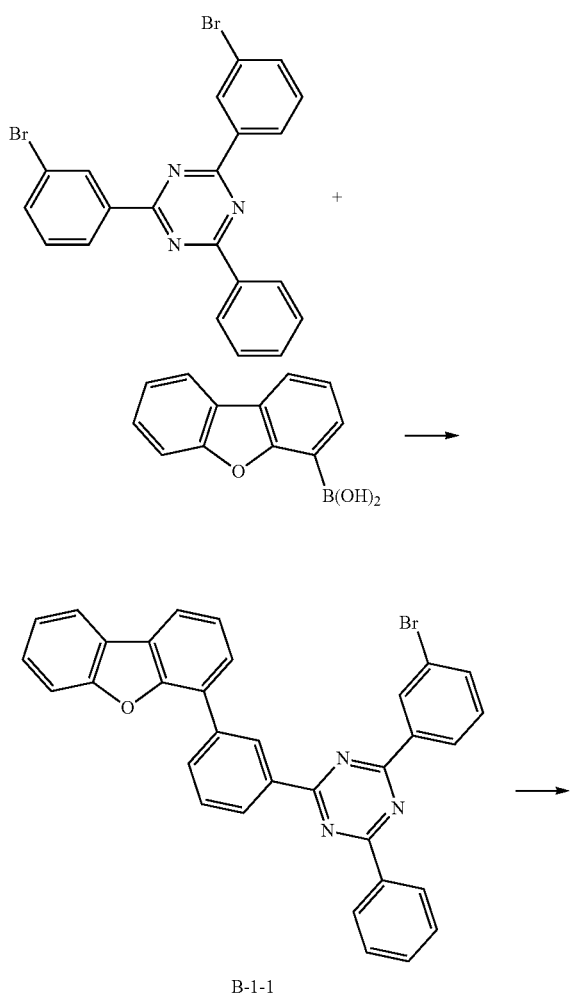

B-1-1

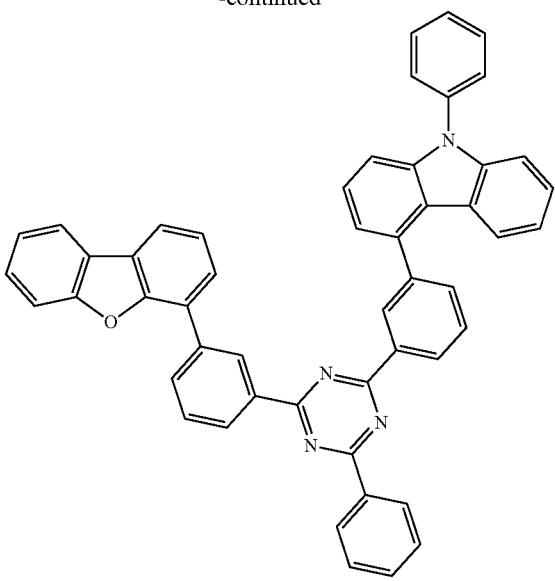

B-1 a) Synthesis of Intermediate B-1-1

30.0 g (64.2 mmol) of 2,4-bis(3-bromophenyl)-6-phenyl-1,3,5-triazine were added to 100 mL of tetrahydrofuran, 100 mL of toluene, and 100 mL of distilled water in a 500 mL round-bottomed flask, 1.0 equivalent of dibenzofuran-4-boronic acid, 0.03 equivalent of tetrakistriphenylphosphine palladium, and 2 equivalents of potassium carbonate were added thereto, and the mixture was heated and refluxed under a nitrogen atmosphere. After 6 hours, the reaction solution was cooled down, an aqueous layer was removed, and an organic layer was dried under a reduced pressure. The obtained solid was washed with water and hexane, the solid was recrystallized with 300 mL of toluene to obtain 21.4 g (60% yield) of Intermediate B-1-1.

b) Synthesis of Intermediate B-1-2

15 g (46.55 mmol) of 4-bromo-9-phenylcarbazole (cas: 1097884-37-1) was added to 200 mL of toluene in a 500 mL round-bottomed flask, 0.05 equivalent of dichlorodiphenylphosphinoferrocene palladium, 1.2 equivalent of bis(pinacolato) diboron, and 2 equivalents of potassium acetate were added thereto, and the mixture was heated and refluxed under a nitrogen atmosphere for 18 hours. The reaction solution was cooled down and added to 1 L of water in a dropwise fashion. A solid obtained therefrom was dissolved in boiling toluene to treat activated carbon and then, filtered with silica gel, and a filtrate therefrom was concentrated. The concentrated solid was stirred with a small amount of hexane and filtered to obtain Intermediate B-1-2 at a yield of 80%.

c) Synthesis of Compound B-1

20 g (36.1 mmol) of Intermediate B-1-1 was added to 100 mL of tetrahydrofuran and 50 mL of distilled water in a 500 mL round-bottomed flask, 1.1 equivalent of Intermediate B-1-2, 0.03 equivalent of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 24 g of Compound B-1.

LC/MS calculated for: C51H32N4O Exact Mass: 716.2576 found for: 717.26 [M+H]

Synthesis Example 2: Synthesis of Compound B-13

[Reaction Scheme 2]

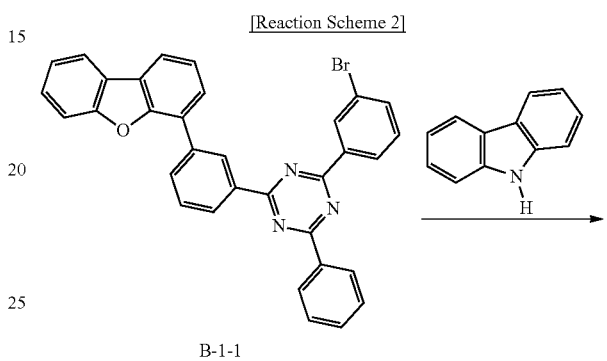

B-1-1

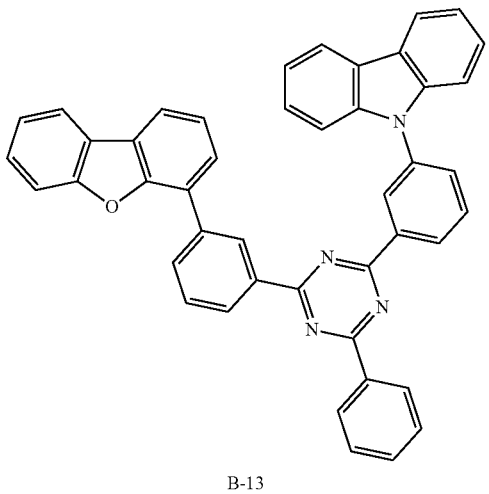

B-13

1 equivalent of Intermediate B-1-1, 1 equivalent of carbazole, 2 eq of sodium t-butoxide, and 0.05 eq of Pd$_2$(dba)$_3$ were suspended to be 0.2 M in xylene, 0.15 eq of tri-tertiarybutylphosphine was added thereto, and the mixture was refluxed and stirred for 18 hours. Methanol was added thereto in 1.5 times as much as the solvent, the mixture was stirred, and a solid obtained therefrom was filtered and washed with 300 mL of water. The solid was recrystallized by using monochlorobenzene to obtain Compound B-13 at a yield of 85%.

LC/MS calculated for: C45H28N4O Exact Mass: 640.2263 found for: 641.23 [M+H]

Synthesis Example 3: Synthesis of Compound B-17

[Reaction Scheme 3]

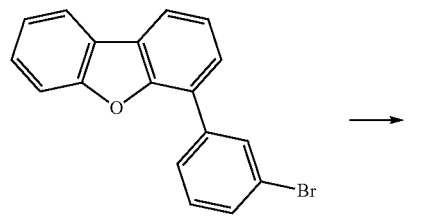

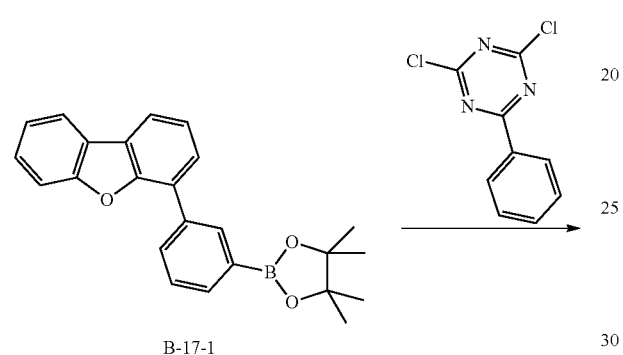

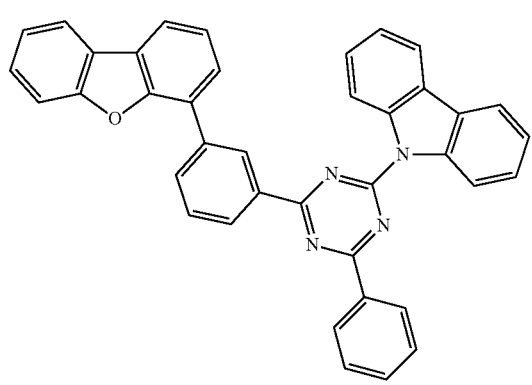

B-17 a) Synthesis of Intermediate B-17-1

15 g (46.4 mmol) of 4-(3-bromophenyl)-dibenzofuran (cas: 887944-90-3) was added to 200 mL of toluene in a 500 mL round-bottomed flask, 0.05 equivalent of dichlorodiphenylphosphinoferrocene palladium, 1.2 equivalent of bis(pinacolato) diboron, and 2 equivalents of potassium acetate were added thereto, and the mixture was heated and refluxed under an nitrogen atmosphere for 18 hours. The solution was washed with water through an extraction, an organic layer therefrom was treated with activated carbon and filtered in silica gel, and a filtrate was concentrated. The concentrated solid was stirred with an amount of hexane and filtered to obtain Intermediate B-17-1 at a yield of 85%.

b) Synthesis of Intermediate B-17-2

9.04 g (40 mmol) of 2,4-dichloro-6-phenyltriazine was added to 60 mL of tetrahydrofuran, 60 mL of toluene, and 60 mL of distilled water in a 500 mL round-bottomed flask, 0.9 equivalent of Intermediate B-17-1, 0.03 equivalent of tetrakistriphenylphosphine palladium, and 2 equivalents of potassium carbonate were added thereto, and the mixture was heated and refluxed under a nitrogen atmosphere. After 6 hours, the reaction solution was cooled down, and after removing an aqueous layer therefrom, an organic layer therein was dried under a reduced pressure. A solid therefrom was washed with water and hexane and then, recrystallized with 300 mL of toluene to obtain Intermediate B-17-2 at a yield of 40%.

c) Synthesis of Compound B-17

1 equivalent of Intermediate B-17-2, 1.1 equivalent of carbazole, 2 eq of sodium t-butoxide, and 0.05 eq of $Pd_2(dba)_3$ were suspended to be 0.2 M in xylene, 0.15 eq of tri-tertiarybutylphosphine was added thereto, and the mixture was refluxed and stirred for 18 hours. Methanol was added thereto 1.5 times as much as the solvent, and a solid therein was filtered and washed with 300 mL of water. The solid was recrystallized by using monochlorobenzene to obtain Compound B-17 at a yield of 80%.

LC/MS calculated for: C39H24N4O Exact Mass: 564.1950 found for: 565.21 [M+H]

Synthesis Example 4: Synthesis of Compound C-1

[Reaction Scheme 4]

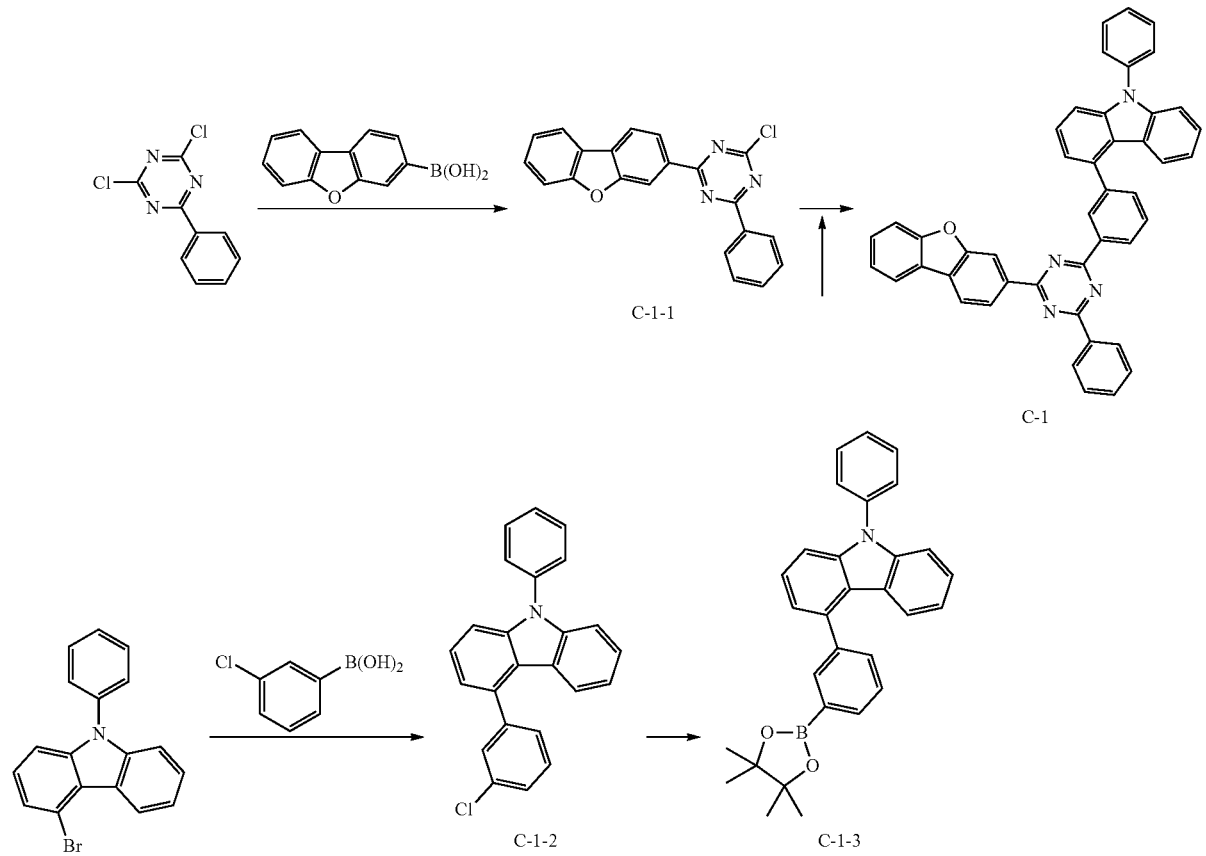

a) Synthesis of Intermediate C-1-1

22.6 g (100 mmol) of 2,4-dichloro-6-phenyltriazine was added to 100 mL of tetrahydrofuran, 100 mL of toluene, and 100 mL of distilled water in a 500 mL round-bottomed flask, 0.9 equivalent of dibenzofuran-3-boronic acid, 0.03 equivalent of tetrakistriphenylphosphine palladium, and 2 equivalents of potassium carbonate were added thereto, and the mixture was heated and refluxed under a nitrogen atmosphere. After 6 hours, the reaction solution was cooled down, and after removing an aqueous layer therefrom, an organic layer therein was dried under a reduced pressure. The obtained solid was washed with water and hexane and recrystallized with 200 mL of toluene to obtain 21.4 g of Intermediate C-1-1 at a yield of 60%.

b) Synthesis of Compound C-1-2

15 g (46.55 mmol) of 4-bromo-9-phenylcarbazole (cas: 1097884-37-1) was added to 140 mL of tetrahydrofuran and 70 mL of distilled water in a 500 mL round-bottomed flask, 1.1 equivalent of 3-chlorophenyl boronic acid, 0.03 equivalents of tetrakistriphenylphosphine palladium, and 2 equivalents of potassium carbonate were added thereto, and the mixture was heated and refluxed under a nitrogen atmosphere. After 12 hours, the reaction solution was cooled down, an organic layer was extracted to remove a solvent under a reduced pressure. A compound concentrated therefrom was treated through silica column chromatography to obtain Intermediate C-1-2 at a yield of 85%.

c) Synthesis of Intermediate C-1-3

12 g (33.9 mmol) of Intermediate C-1-2 was added to 150 mL of xylene in a 500 mL round-bottomed flask, 0.05 equivalent of dichlorodiphenylphosphinoferrocene palladium, 1.2 equivalent of bis(pinacolato) diboron, and 2 equivalents of potassium acetate were added thereto, and the mixture was heated and refluxed under a nitrogen atmosphere for 18 hours. The reaction solution was cooled down and then, washed with water through an extraction, an organic layer therefrom was treated with activated carbon and filtered in silica gel, and a filtrate therefrom was concentrated. A solid concentrated therefrom was stirred with a small amount of hexane and filtered to obtain Intermediate C-1-3 at a yield of 75%.

d) Synthesis of Compound C-1

8 g (22.4 mmol) of Intermediate C-1-1 was added to 80 mL of tetrahydrofuran and 40 mL of distilled water in a 500 mL round-bottomed flask, 1.0 equivalent of Intermediate C-1-3, 0.03 equivalent of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 12 g of Compound C-1.

LC/MS calculated for: C45H28N4O Exact Mass: 640.2263 found for: 641.24

Synthesis Example 5: Synthesis of Compound C-2

[Reaction Scheme 5]

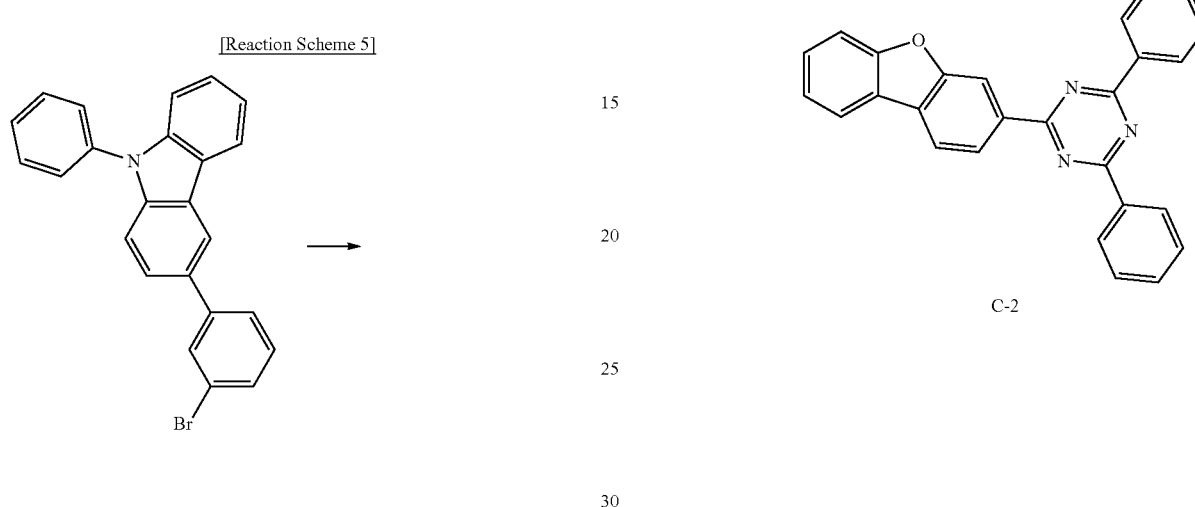

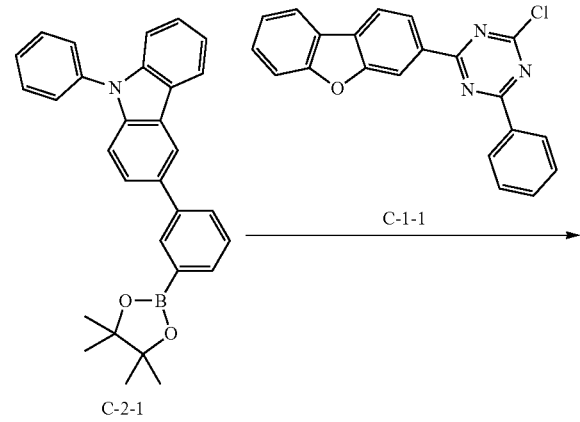

a) Synthesis of Intermediate C-2-1

15 g (46.4 mmol) of 3-(3-bromophenyl)-9-phenylcarbazole (cas: 854952-59-3) was added to 200 mL of toluene in a 500 mL round-bottomed flask, 0.05 equivalent of dichlorodiphenylphosphinoferrocene palladium, 1.2 equivalent of bis(pinacolado) diboron, and 2 equivalents of potassium acetate were added thereto, and the mixture was heated and refluxed under a nitrogen atmosphere for 18 hours. The reaction solution was cooled down and added to 1 L of water in a dropwise fashion to collect a solid. The solid was dissolved in boiling toluene to treat activated carbon and filtered in silica gel, and a filtrate therefrom was concentrated. The concentrated solid was stirred with a small amount of hexane and filtered to obtain Intermediate C-2-1 at a yield of 85%.

b) Synthesis of Compound C-2

8 g (22.4 mmol) of Intermediate C-1-1 according to Synthesis Example 4 was added to 80 mL of tetrahydrofuran and 40 mL of distilled water in a 500 mL round-bottomed flask, 1.0 equivalent of Intermediate C-2-1, 0.03 equivalent of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was washed with 500 mL of water. The solid was recrystallized by using 500 mL of monochlorobenzene to obtain 13 g of Compound C-1.

LC/MS calculated for: C45H28N4O Exact Mass: 640.2263 found for: 641.24

Synthesis Example 6: Synthesis of Compound C-12

[Reaction Scheme 6]

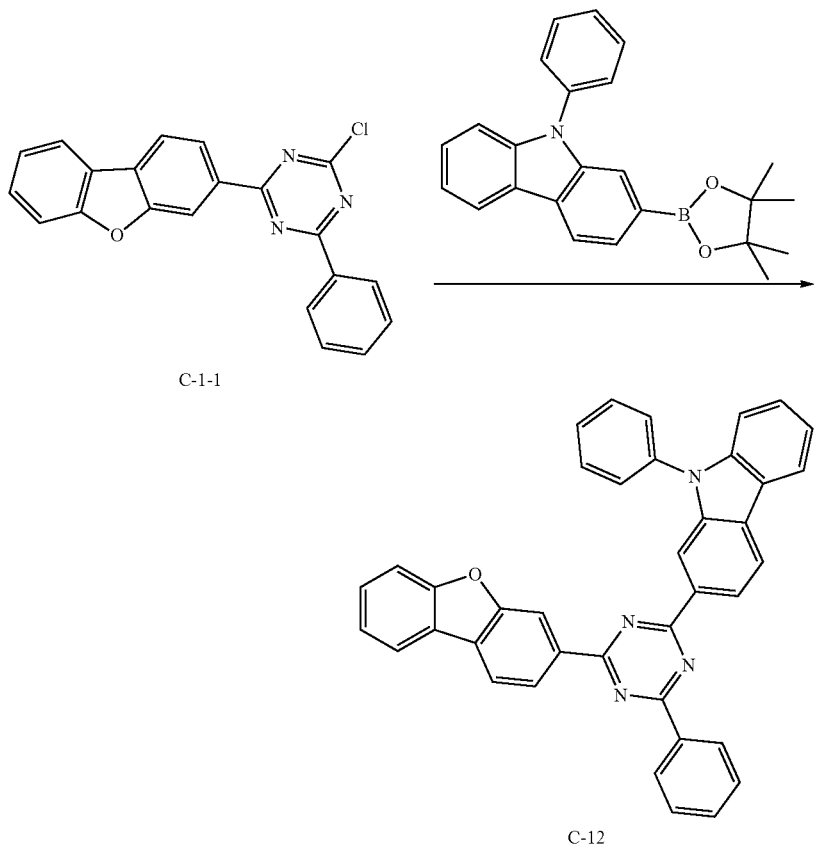

8 g (22.4 mmol) of Intermediate C-1-1 according to Synthesis Example 4 was added to 80 mL of tetrahydrofuran and 40 mL of distilled water in a 500 mL round-bottomed flask, 1.0 equivalent of 9-phenyl-2-(4,4,5,5-tetramethyl-1,3,2-dioxaborolan-2-yl)-carbazole (cas: 1246669-45-3), 0.03 equivalent of tetrakistriphenylphosphine palladium, and 2 equivalents of potassium carbonate were added thereto, and the mixture was heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 11 g of Compound C-12.

LC/MS calculated for: C39H24N4O Exact Mass: 564.1950 found for: 565.20 Synthesis Example 7: Synthesis of Compound C-16

[Reaction Scheme 7]

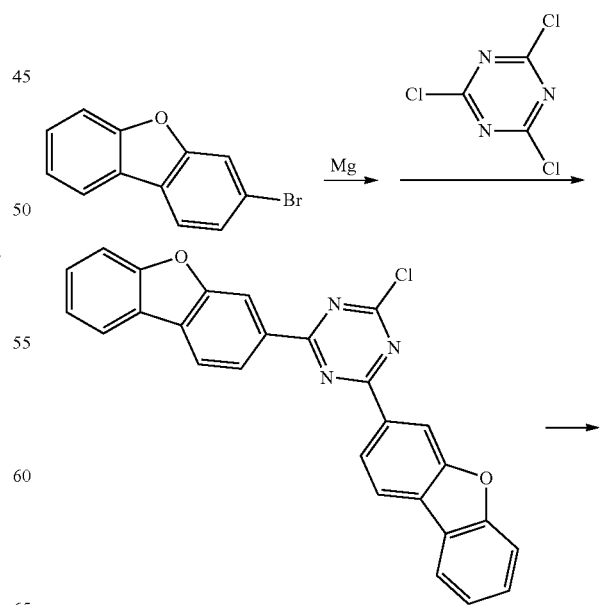

-continued

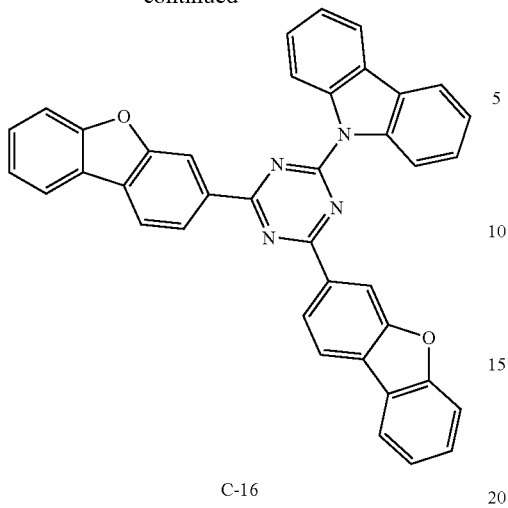

C-16

-continued

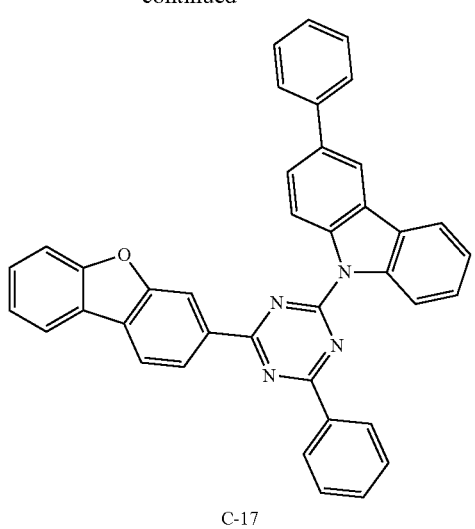

C-17 a) Synthesis of Intermediate C-16-1

Magnesium (7.86 g, 323 mmol) and iodine (1.64 g, 6.46 mmol) were added to 0.1 L of tetrahydrofuran (THF) in a nitrogen environment, the mixture was stirred for 30 minutes, and 3-bromo dibenzofuran (80 g, 323 mmol) dissolved in 0.3 L of THF was slowly added thereto in a dropwise fashion at 0° C. over 30 minutes. The mixed solution was slowly added in a dropwise fashion to 29.5 g (160 mmol) of cyanuric chloride dissolved in 0.5 L of THF at 0° C. over 30 minutes. After heating a reaction up to room temperature, the mixture was stirred for 1 hour and additionally stirred for 12 hours under a reflux condition. After cooling down the reaction, water was slowly added thereto to finish the reaction, and an organic solvent therefrom was concentrated under a reduced pressure to obtain a solid. The solid was stirred with 200 mL of acetone and filtered to obtain Intermediate C-16-1 at a yield of 40%.

b) Synthesis of Compound C-16

Compound C-16 was synthesized according to the same method as Synthesis Example 2 by using Intermediate C-16-1.

LC/MS calculated for: C39H22N4O2 Exact Mass: 578.1743 found for 579.20

Synthesis Example 8: Synthesis of Compound C-17

Compound C-17 was synthesized according to the same method as Synthesis Example 2 by using Intermediate C-1-1 and 3-phenyl-9H-carbazole respectively by 1 equivalent.

LC/MS calculated for: C39H24N4O Exact Mass: 564.1950 found for: 565.20

Synthesis Example 9: Synthesis of Compound C-21

[Reaction Scheme 9]

[Reaction Scheme 8]

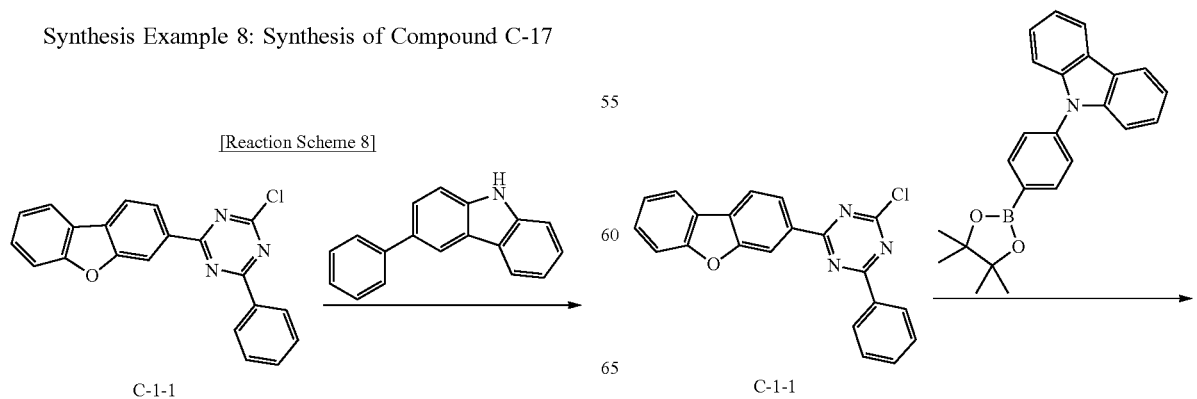

Synthesis Example 10: Synthesis of Compound C-22

[Reaction Scheme 10]

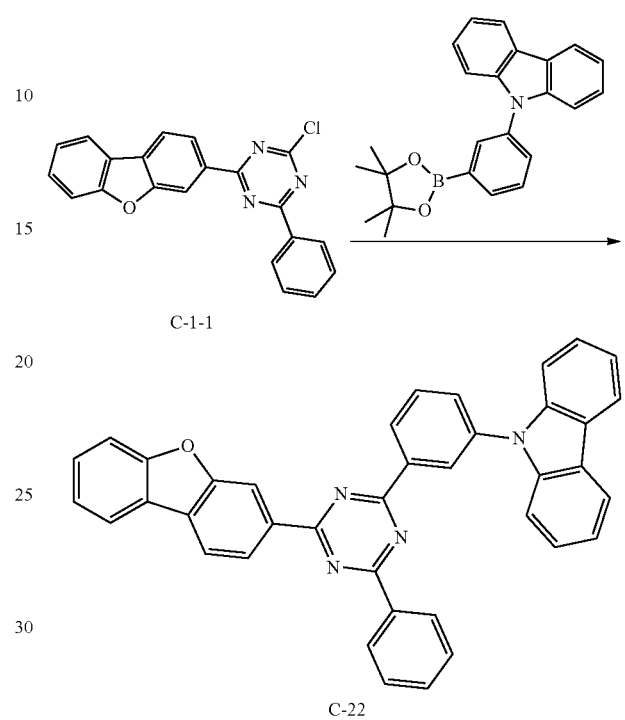

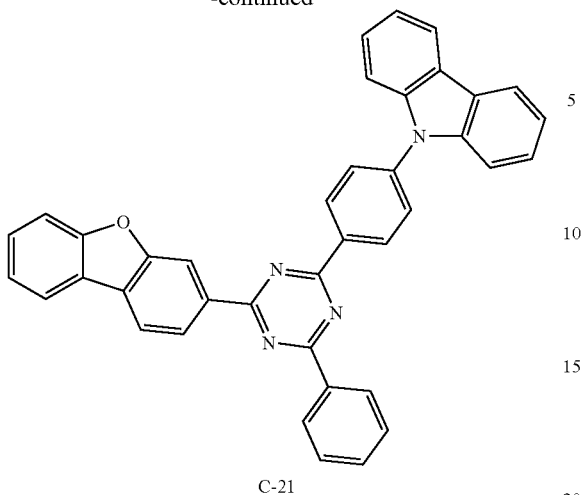

C-21

Compound C-21 was synthesized according to the same method as Synthesis Example 6 by using Intermediate C-1-1 and 9-(4-(4,4,5,5-tetramethyl-1,3,2-dioxaborolan-2-yl)-phenyl)-carbazole (cas: 785051-54-9) respectively by 1.0 equivalent.

LC/MS calculated for: C39H24N4O Exact Mass: 564.1950 found for: 565.20

Compound C-22 was synthesized according to the same method as Synthesis Example 6 by using Intermediate C-1-1 and 9-(3-(4,4,5,5-tetramethyl-1,3,2-dioxaborolan-2-yl)-phenyl)-carbazole (cas: 870119-58-7) respectively by 1.0 equivalent.

LC/MS calculated for: C39H24N4O Exact Mass: 564.1950 found for: 565.20

Synthesis Example 11: Synthesis of Compound C-25

[Reaction Scheme 11]

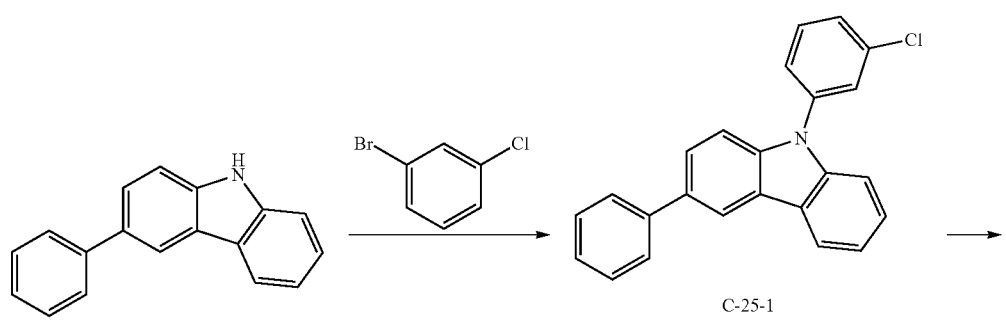

-continued

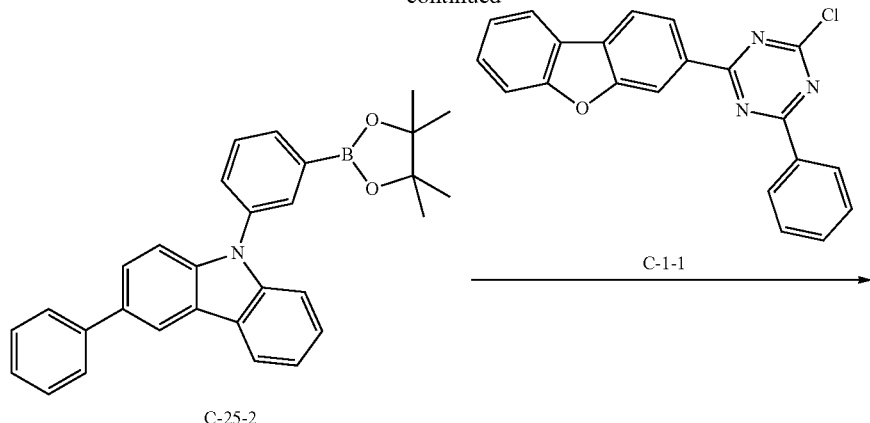

C-25-2

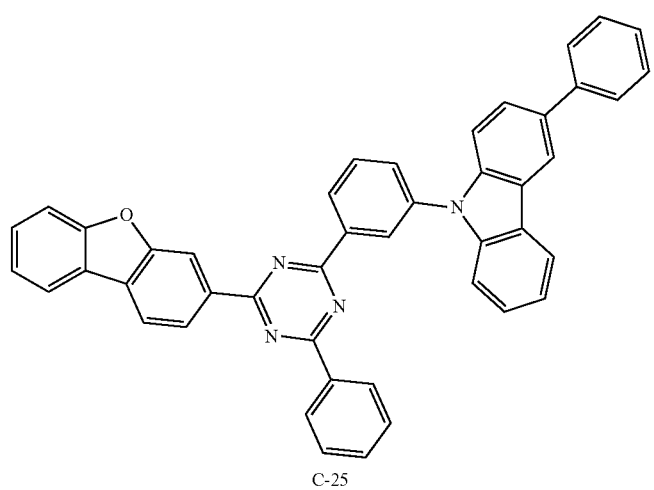

C-25 a) Synthesis of Intermediate C-25-1

Intermediate C-25-1 was synthesized according to the same method as Synthesis Example 2 by using 1 equivalent of 3-phenyl-9H-carbazole and 1.2 equivalent of 3-chloro-1-bromobenzene.

b) Synthesis of Intermediate C-25-2

Intermediate C-25-2 was synthesized according to the same method as a) of Synthesis Example 5 by using Intermediate C-25-1.

c) Synthesis of Compound C-25

Intermediate C-25 was synthesized according to the same method as a) of Synthesis Example 6 by using Intermediate C-25-2 and Intermediate C-1-1 respectively by 1.0 equivalent.

LC/MS calculated for: C45H28N4O Exact Mass: 640.2263 found for: 641.23

Synthesis Example 12: Synthesis of Compound B-14

[Reaction Scheme 12]

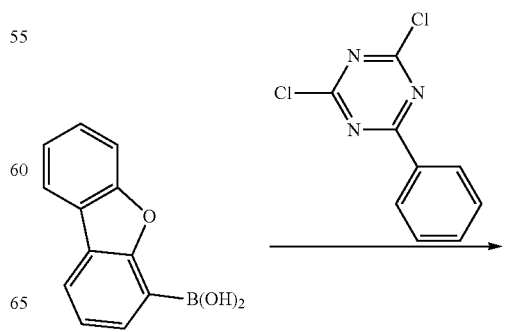

131

-continued

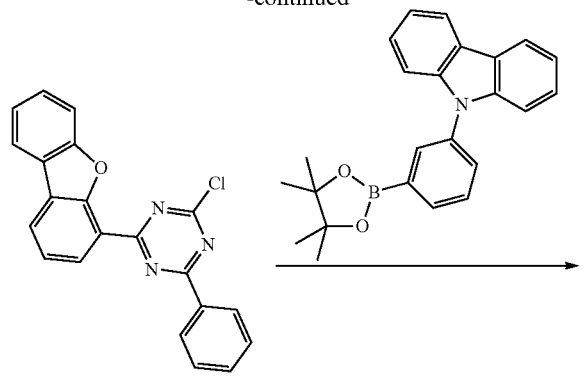

B-14-1

B-14 a) Synthesis of Intermediate B-14-1

Intermediate B-14-1 was synthesized according to the same method as a) of Synthesis Example 4 by using 1 equivalent of 2,4-dichloro-6-phenyltriazine and 0.9 equivalent of dibenzofuran-4-boronic acid.

b) Synthesis of Compound B-14

Intermediate B-14 was synthesized according to the same method as Synthesis Example 6 by using Intermediate B-14-1 and 9-(3-(4,4,5,5-tetramethyl-1,3,2-dioxaborolan-2-yl)-phenyl)-carbazole (cas: 870119-58-7) by respectively 1.0 equivalent.

LC/MS calculated for: C39H24N4O Exact Mass: 564.1950 found for: 565.20

Synthesis Example 13: Synthesis of Compound B-22

132

-continued

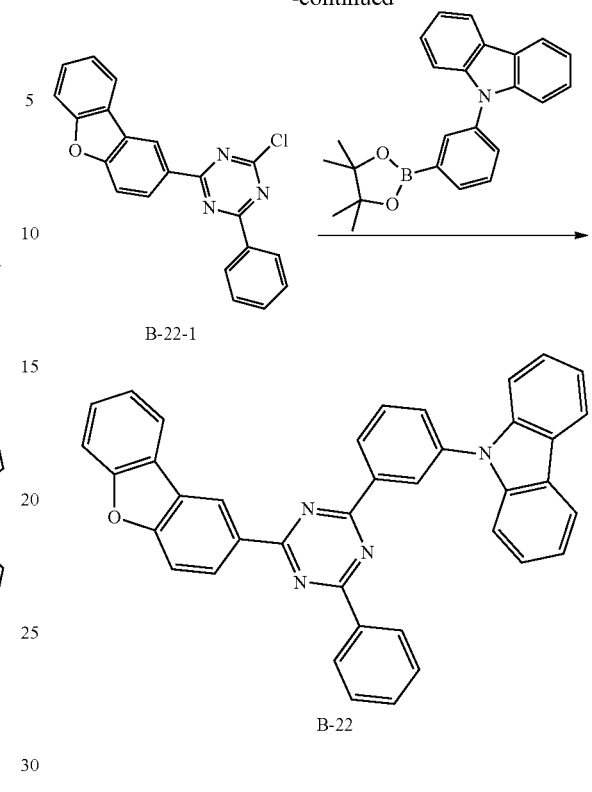

B-22-1

B-22 a) Synthesis of Intermediate B-22-1

Intermediate B-22-1 was synthesized according to the same method as a) of Synthesis Example 4 by using 1 equivalent of 2,4-dichloro-6-phenyltriazine and 0.9 equivalent of dibenzofuran-2-boronic acid.

b) Synthesis of Compound B-22

Compound B-22 was synthesized according to the same method as Synthesis Example 6 by using Intermediate B-22-1 and 9-(3-(4,4,5,5-tetramethyl-1,3,2-dioxaborolan-2-yl)-phenyl)-carbazole (cas: 870119-58-7) respectively by 1.0 equivalent.

LC/MS calculated for: C39H24N4O Exact Mass: 564.1950 found for: 565.21

Synthesis Example 14: Synthesis of Compound B-25

[Reaction Scheme 13]

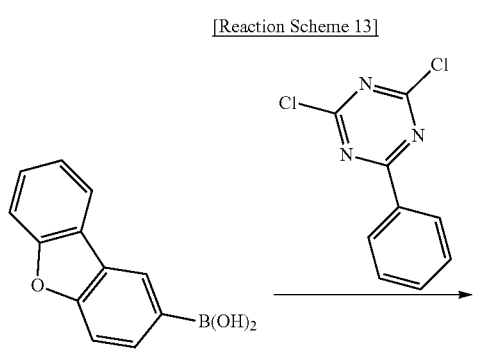

[Reaction Scheme 14]

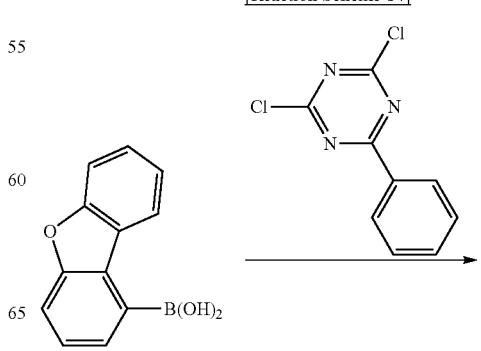

-continued

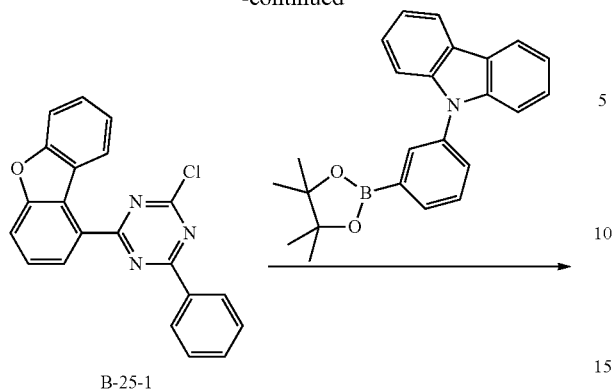

B-25-1

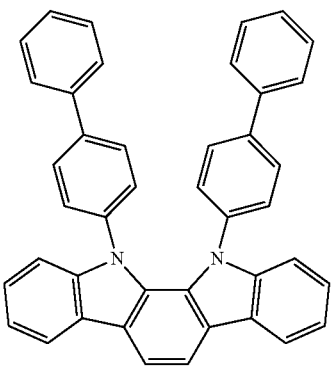

B-25 a) Synthesis of Intermediate B-25-1

Intermediate B-25-1 was synthesized according to the same method as a) of Synthesis Example 4 by using 1 equivalent of 2,4-dichloro-6-phenyltriazine and 0.9 equivalent of dibenzofuran-1-boronic acid.

b) Synthesis of Compound B-25

Compound B-25 was synthesized according to the same method as Synthesis Example 6 by using Intermediate B-25-1 and 9-(3-(4,4,5,5-tetramethyl-1,3,2-dioxaborolan-2-yl)-phenyl)-carbazole (cas: 870119-58-7) respectively by 1.0 equivalent.
LC/MS calculated for: C39H24N4O Exact Mass: 564.1950 found for: 565.20

Preparation of Second Host

D-1

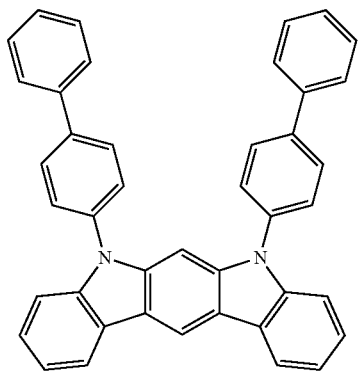

-continued

D-21

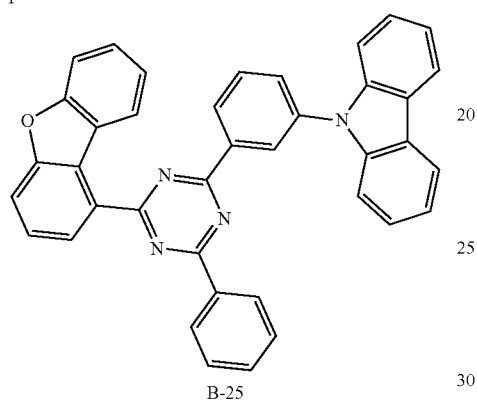

D-41

D-72

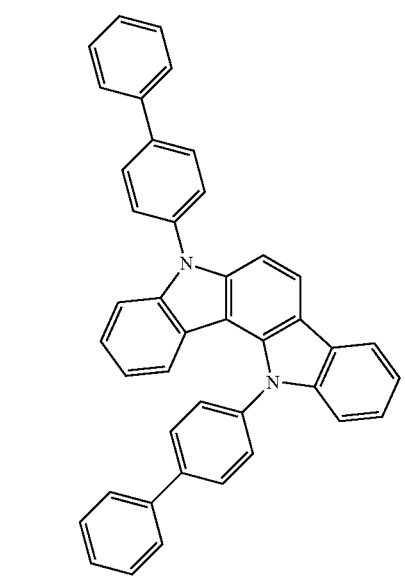

Synthesis Example 15: Synthesis of Compound D-1

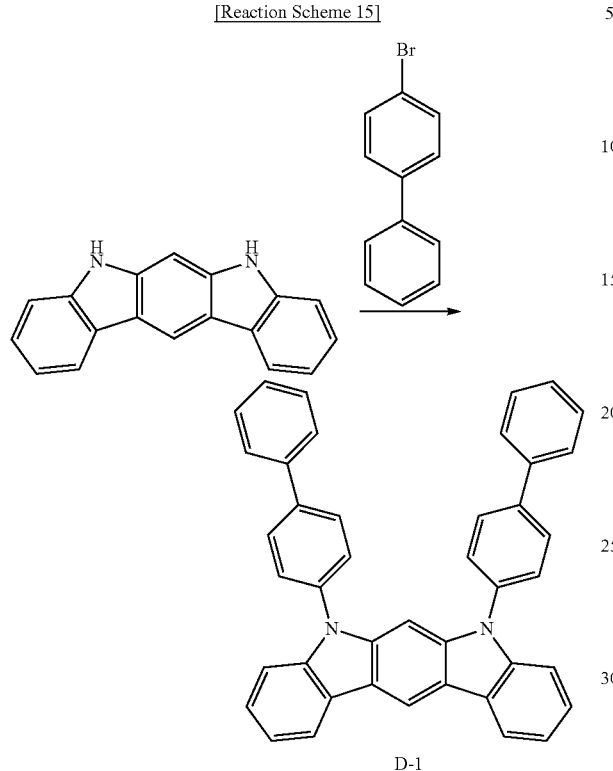

D-1

Compound D-1 was synthesized according to the same method as Synthesis Example 2 by using 1 equivalent of a synthesis intermediate, 5,7-dihydro-indolo[2,3-b]carbazole (cas: 111296-90-3) and 2.5 equivalents of 4-bromo-1,1'-biphenyl (cas: 92-66-0).

LC/MS calculated for: C42H28N2 Exact Mass: 560.2252 found for: 561.24

Synthesis Examples 16 to 18: Synthesis of Compound D-21, Compound D-41 and Compound D-72

Compound D-21, Compound D-41, and Compound D-72 were synthesized according to the same method as the synthesis method of Compound D-1 of Synthesis Example 15 by intermediates 11,12-dihydro-indolo[2,3-a]carbazole (cas: 60511-85-5), 5,8-dihydro-indolo[2,3-c]carbazole (cas: 200339-30-6), 5,12-dihydro-indolo[3,2-a]carbazole (cas: 111296-91-4), respectively.

Preparation of Phosphorescent Dopant

Synthesis Example 19: Synthesis of Compound E-24

Dopant Compound E-24 was prepared through the same reaction as above except for using an indium complex described [Reaction Scheme 16] as a starting material in a method of manufacturing Compound II-1 of US2014-0131676.

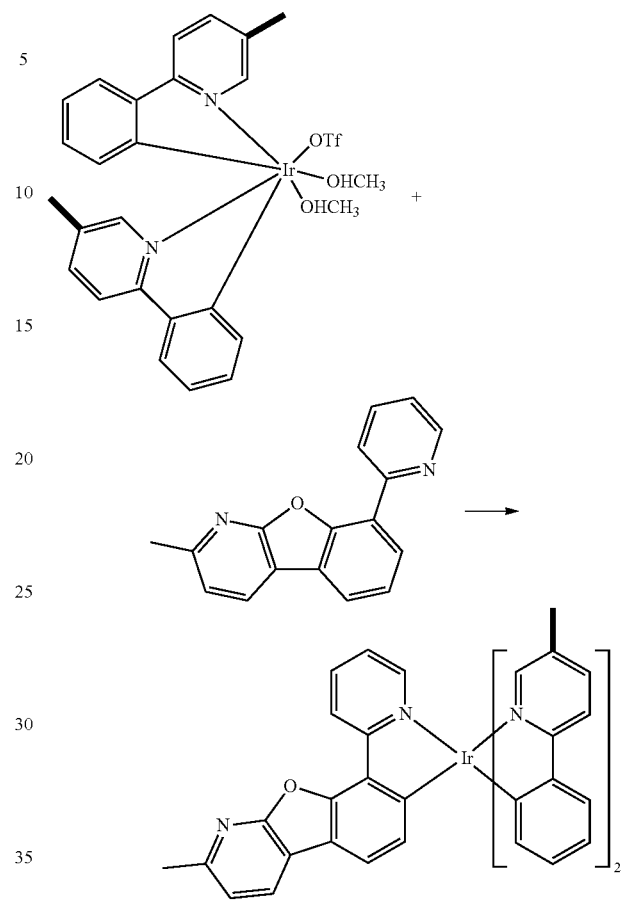

(Manufacture of Organic Light Emitting Diode)

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. On the hole transport layer, a 400 Å-thick light emitting layer was formed by vacuum-depositing Compound C-1 as a first host and Compound D-1 as a second host and 10 wt % of E-24 as a phosphorescent dopant. Herein Compound C-1 and Compound D-1 were used in a weight ratio of 4:6, but their ratio in the following Examples was separately provided. Subsequently, on the light emitting layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1200 Å thick, manufacturing an organic light emitting diode.

The organic light emitting diode had a five-layered organic thin layer, and specifically a structure of ITO/Compound A (700 Å)/Compound B (50 Å)/Compound C (1020 Å)/EML[Compound C-1: Synthesis of Compound D-1: Synthesis of Compound E-24 (10 wt %)] (400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinolone

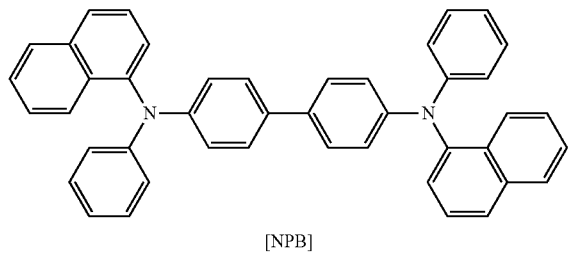

[NPB]

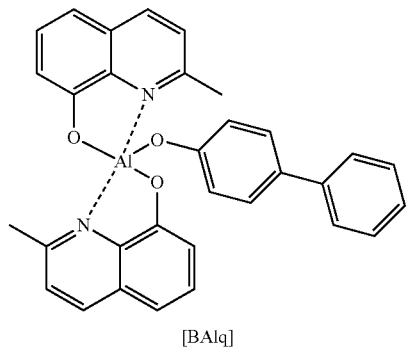

[BAlq]

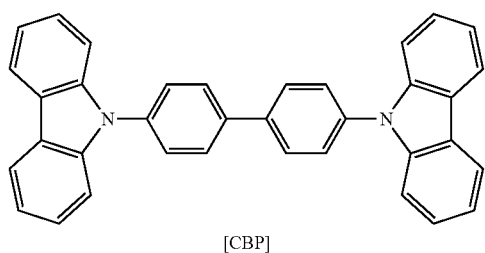

[CBP]

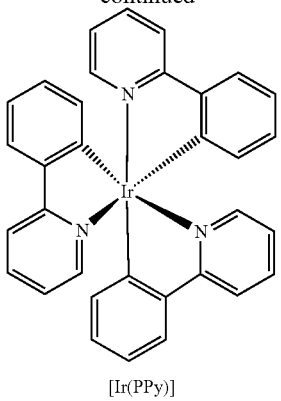

[Ir(PPy)]

Examples 2 to Example 24 and Comparative Examples 1 to 6

Each organic light emitting diodes was manufactured according to the same method as Example 1 except for changing the composition of the first host, the second host, and the phosphorescent dopant into each composition shown in Table 1.

Evaluation 1: Luminous Efficiency and Life-Span Increase Effect

Luminous efficiency and life-span characteristics of the organic light emitting diodes according to Examples 1 to 24 and Comparative Examples 1 to 6 were evaluated. The measurements were specifically performed in the following methods, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and, the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T90 life-spans of the organic light emitting diodes according to Examples 1 to 24 and Comparative Examples 1 to 6 were measured as a time when their luminance decreased down to 90% relative to the initial luminance (cd/m$^2$) after emitting light with 5000 cd/m$^2$ as the initial luminance (cd/m$^2$) and measuring their luminance decrease depending on a time with a Polanonix life-span measurement system.

(5) Measurement of Driving Voltage

A driving voltage of each diode was measured using a current-voltage meter (Keithley 2400) at 15 mA/cm$^2$.

TABLE 1

Device results

|  | First host | Second host | Ratio of first and second hosts | Dopant | Color | Efficiency Cd/A | Life-span T90 | Driving (Vd) |
| --- | --- | --- | --- | --- | --- | --- | --- | --- |
| Comparative Example 1 | C-1 | — | alone | E-24 | green | 56 | 30 | 4.1 |
| Comparative Example 2 | C-1 | CBP | 4:6 | E-24 | green | 61 | 60 | 4.8 |
| Example 1 | C-1 | D-1 | 4:6 | E-24 | green | 67 | 580 | 3.7 |
| Comparative Example 3 | C-1 | D-1 | 4:6 | Ir(ppy)$_3$ | green | 48 | 160 | 4.2 |
| Comparative Example 4 | C-22 | — | alone | E-24 | green | 53 | 40 | 4.0 |
| Comparative Example 5 | C-22 | CBP | 4:6 | E-24 | green | 60 | 80 | 4.7 |
| Example 2 | C-22 | D-1 | 4:6 | E-24 | green | 68 | 620 | 3.7 |
| Comparative Example 6 | C-22 | D-1 | 4:6 | Ir(ppy)$_3$ | green | 49 | 190 | 4.2 |
| Example 3 | C-1 | D-21 | 4:6 | E-24 | green | 63 | 270 | 4.3 |
| Example 4 | C-22 | D-21 | 4:6 | E-24 | green | 65 | 350 | 4.4 |
| Example 5 | C-1 | D-41 | 4:6 | E-24 | green | 65 | 490 | 3.5 |
| Example 6 | C-22 | D-41 | 4:6 | E-24 | green | 66 | 520 | 3.5 |
| Example 7 | C-1 | D-72 | 4:6 | E-24 | green | 69 | 520 | 3.8 |
| Example 8 | C-22 | D-72 | 4:6 | E-24 | green | 67 | 560 | 3.8 |
| Example 9 | C-2 | D-1 | 4:6 | E-24 | green | 70 | 590 | 3.8 |
| Example 10 | C-12 | D-1 | 4:6 | E-24 | green | 64 | 480 | 3.5 |
| Example 11 | C-16 | D-1 | 4:6 | E-24 | green | 65 | 620 | 3.6 |
| Example 12 | C-17 | D-1 | 4:6 | E-24 | green | 67 | 570 | 3.7 |
| Example 13 | C-21 | D-1 | 4:6 | E-24 | green | 64 | 550 | 3.7 |
| Example 14 | C-22 | D-1 | 4:6 | E-24 | green | 68 | 600 | 3.8 |
| Example 15 | C-25 | D-1 | 4:6 | E-24 | green | 69 | 630 | 3.8 |
| Example 16 | B-1 | D-1 | 4:6 | E-24 | green | 68 | 380 | 4.0 |
| Example 17 | B-13 | D-1 | 4:6 | E-24 | green | 67 | 250 | 4.1 |
| Example 18 | B-17 | D-1 | 4:6 | E-24 | green | 67 | 330 | 3.9 |
| Example 19 | B-14 | D-1 | 4:6 | E-24 | green | 65 | 350 | 4.0 |
| Example 20 | B-22 | D-1 | 4:6 | E-24 | green | 64 | 210 | 4.2 |
| Example 21 | B-25 | D-1 | 4:6 | E-24 | green | 62 | 230 | 4.1 |
| Example 22 | B-14 | D-72 | 4:6 | E-24 | green | 66 | 440 | 4.1 |
| Example 23 | B-22 | D-72 | 4:6 | E-24 | green | 63 | 250 | 4.4 |
| Example 24 | B-25 | D-72 | 4:6 | E-24 | green | 64 | 290 | 4.3 |

Referring to Table 1, when a material including DBX and carbazole was used as a first host, and indolocarbazole was used as a second host, an advantage in terms of driving and life-span was obtained, compared with when the first host was used alone or when CBP was used as the second host. In addition, when Ir(ppy)$_3$ as a phosphorescent dopant not including a DBX bone was used, a life-span and efficiency were largely increased, compared with when Compound E-24 as a phosphorescent dopant including a DBX bone was used. Particularly, when the structure of directly linking a position No. 3 of dibenzofuran with triazine as the first host was used, an effect of additionally decreasing a driving voltage but additionally increasing a life-span was obtained.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode
105: organic layer
110: cathode
120: anode
130: light emitting layer
140: hole auxiliary layer

What is claimed is:

1. An organic optoelectronic device, comprising:
an anode and a cathode facing each other; and
an organic layer disposed between the anode and the cathode,
wherein the organic layer includes at least one of a hole injection layer, a hole transport layer, a light emitting layer, and an electron transport layer,
wherein the light emitting layer includes a first host selected from compounds of [Group-1],
a second host selected from compounds of [Group-2] and
a phosphorescent dopant represented by Chemical Formula 4,

[Group-1]
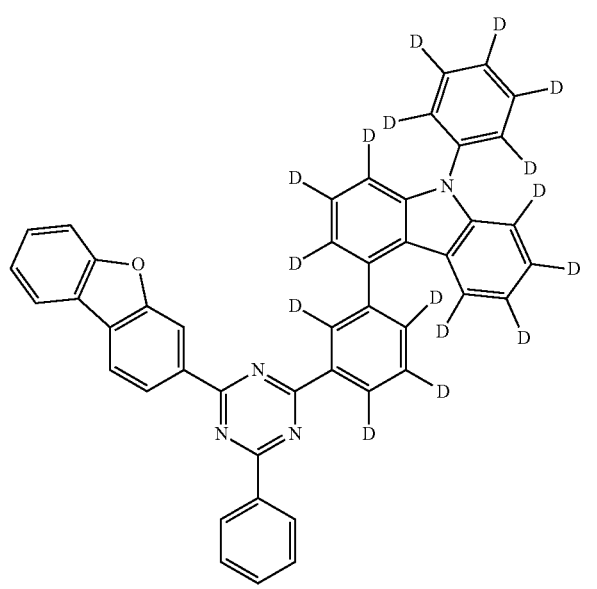
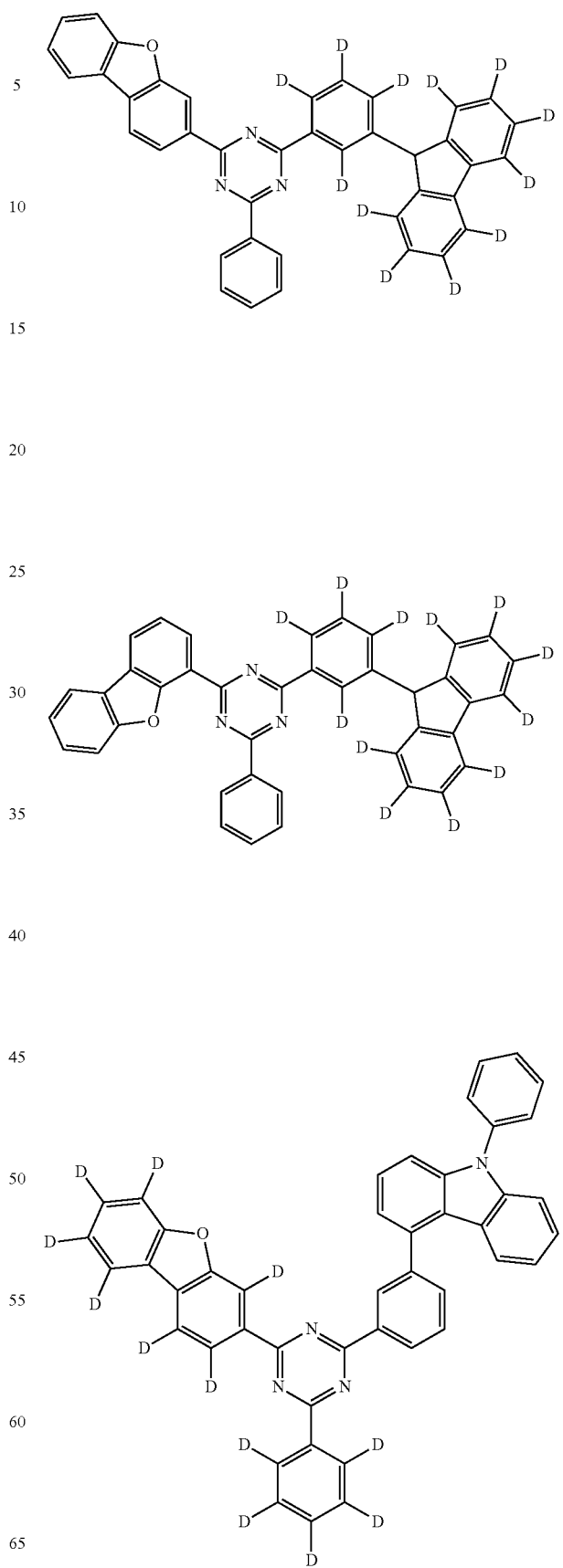

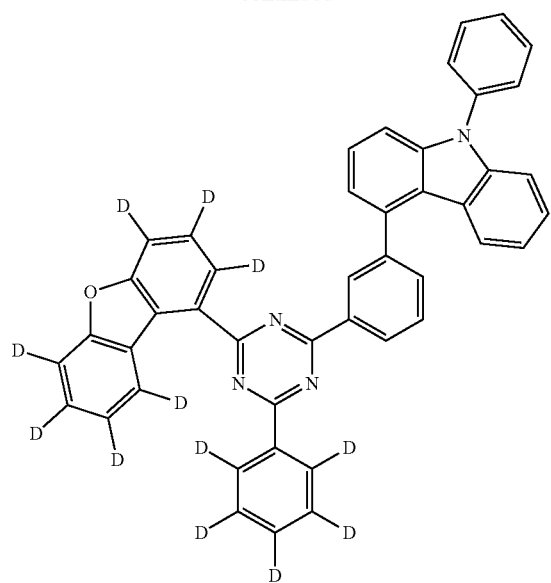
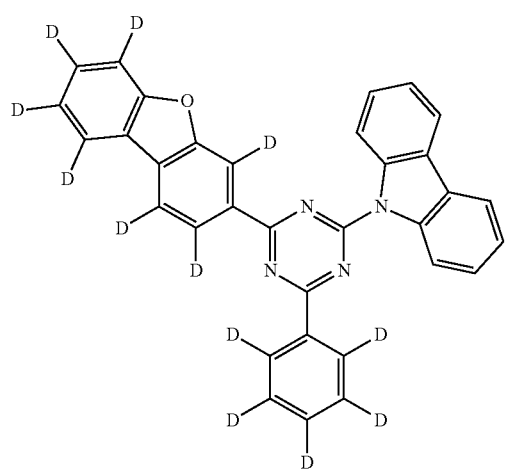
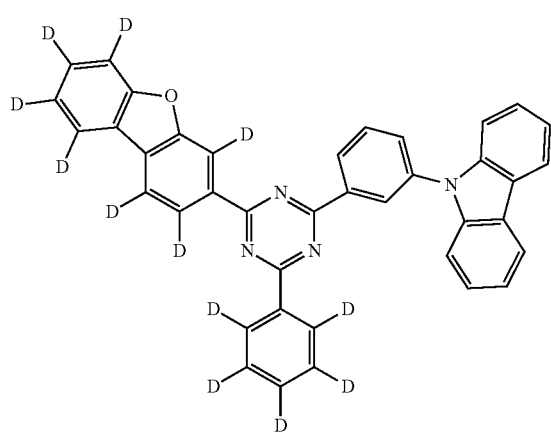
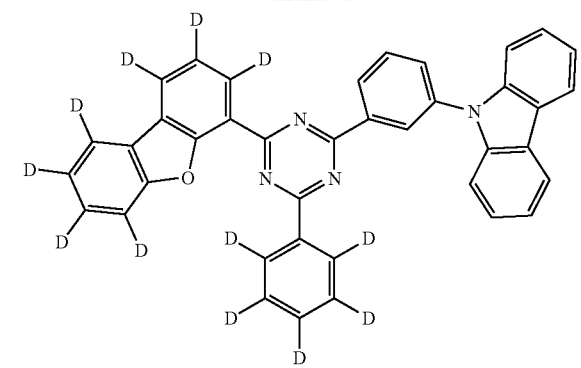
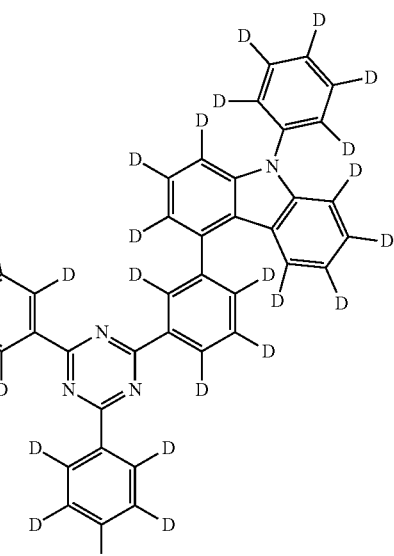
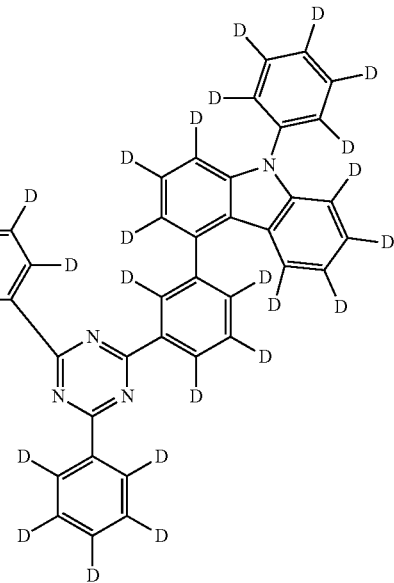

145
-continued
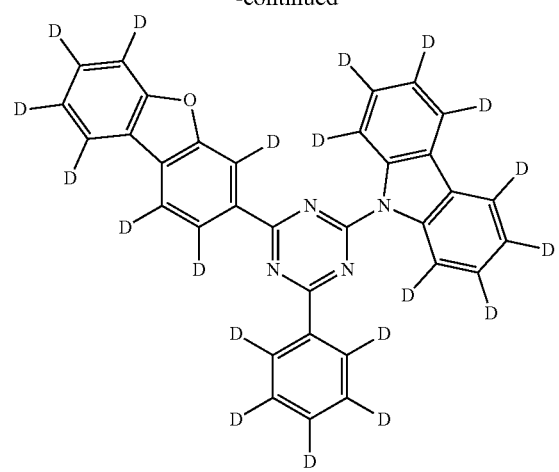
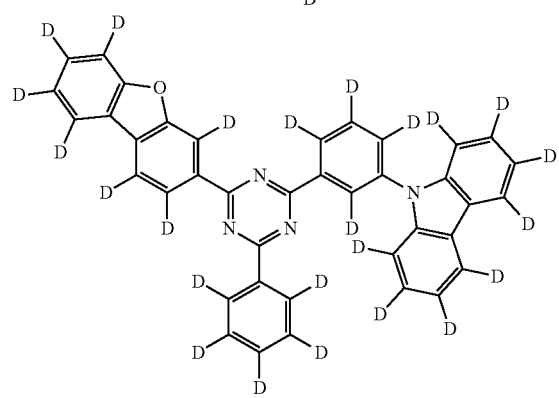
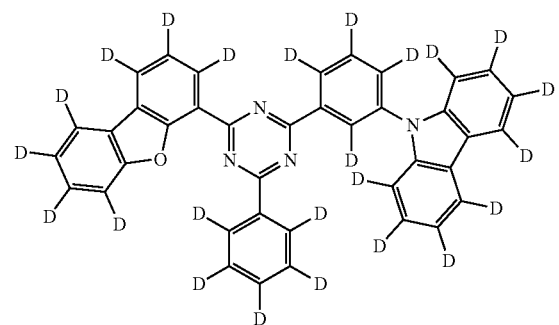
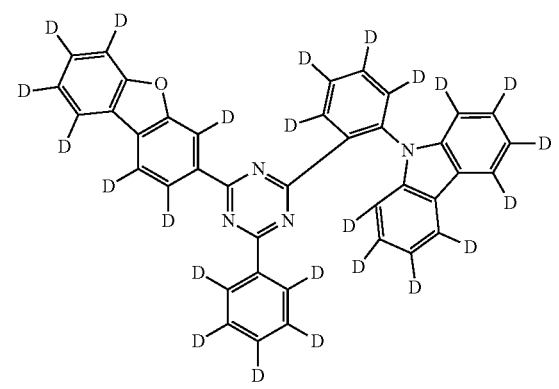
146
-continued
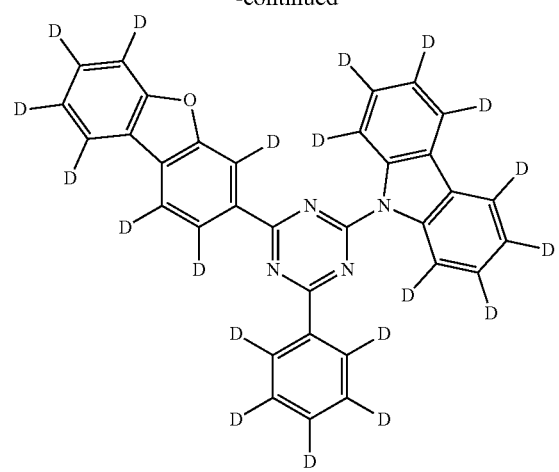
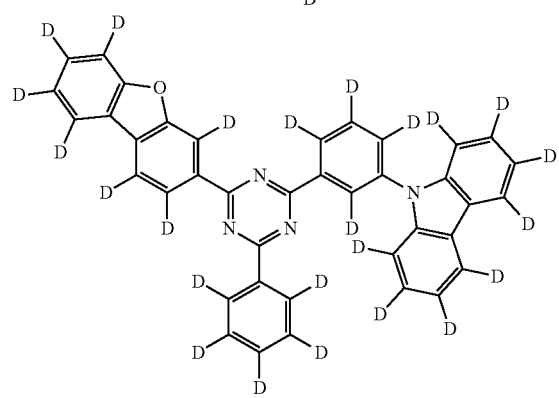
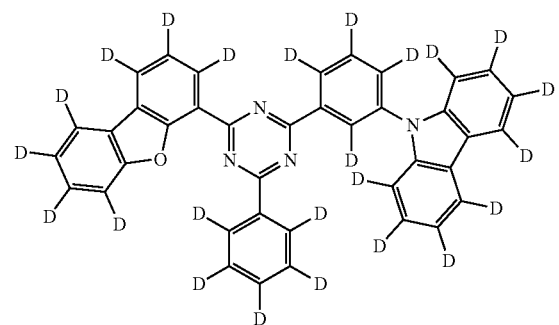
[Group-2]
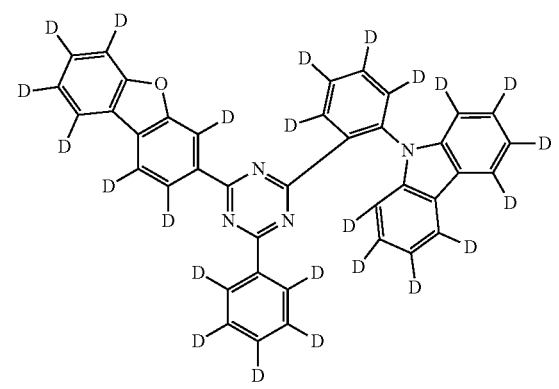

147
-continued
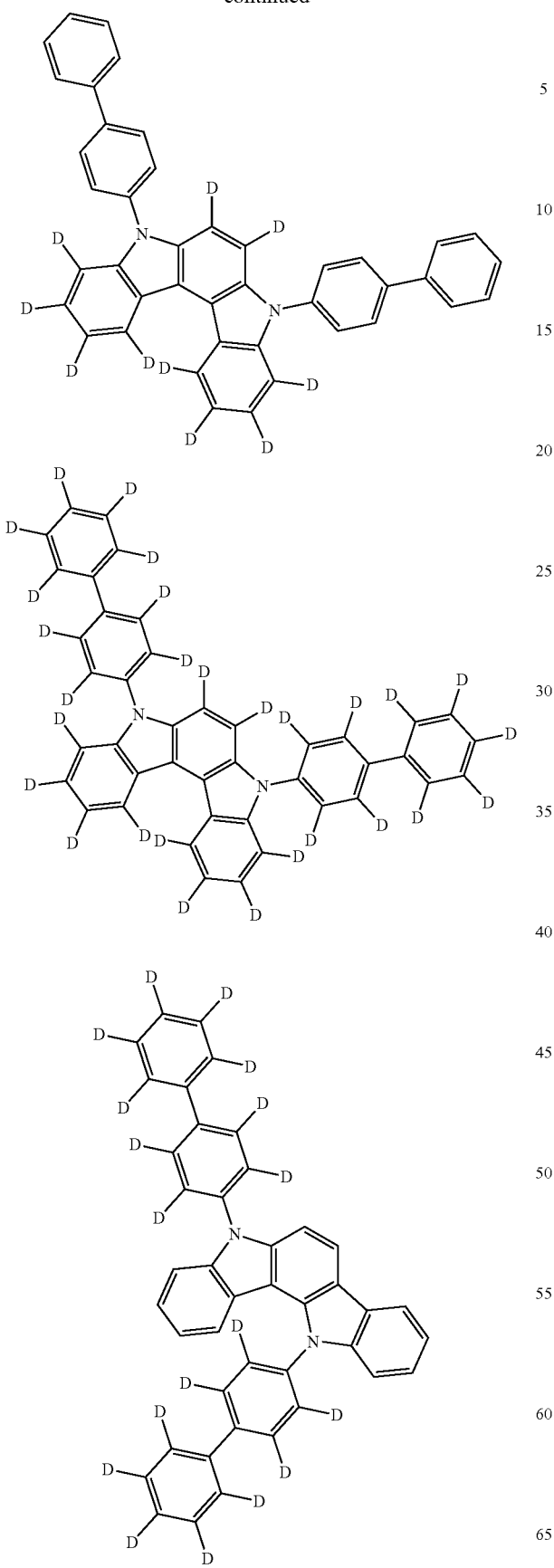
148
-continued
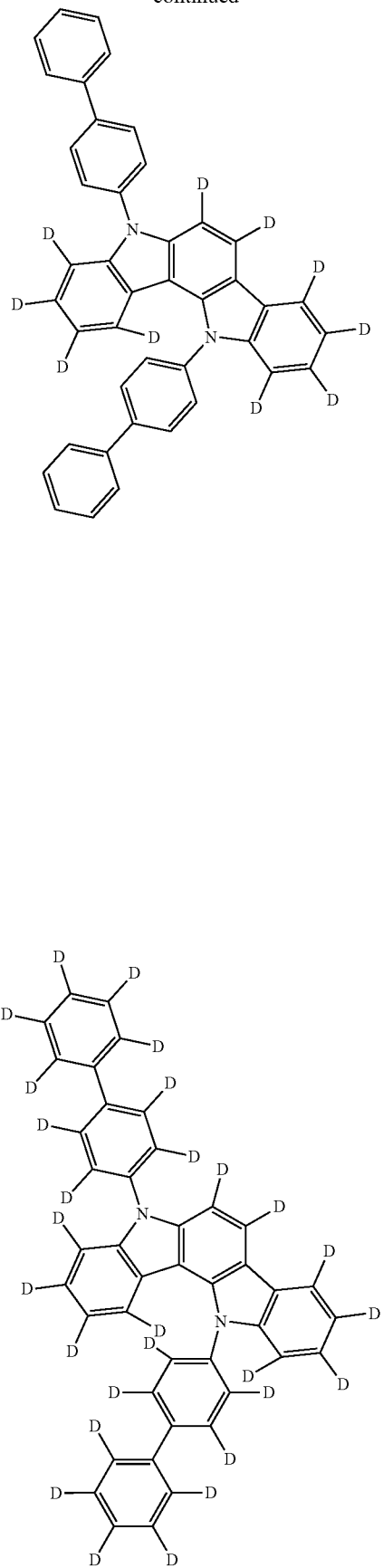

-continued

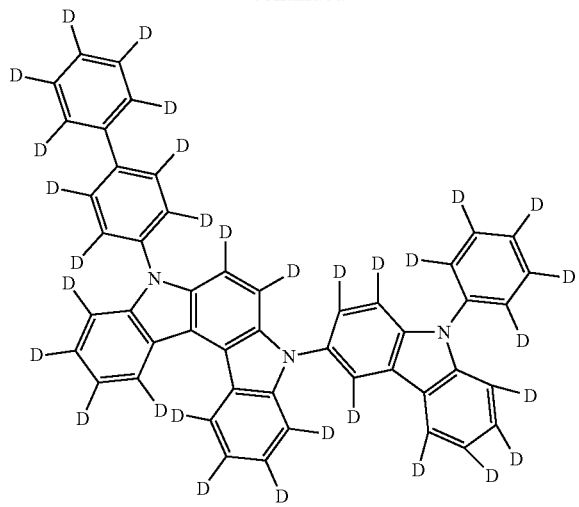

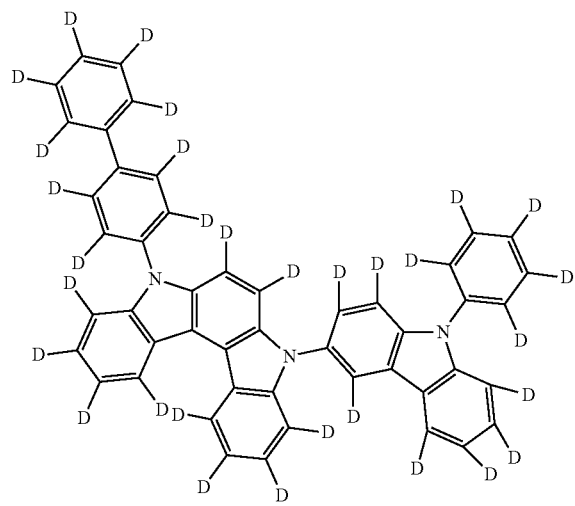

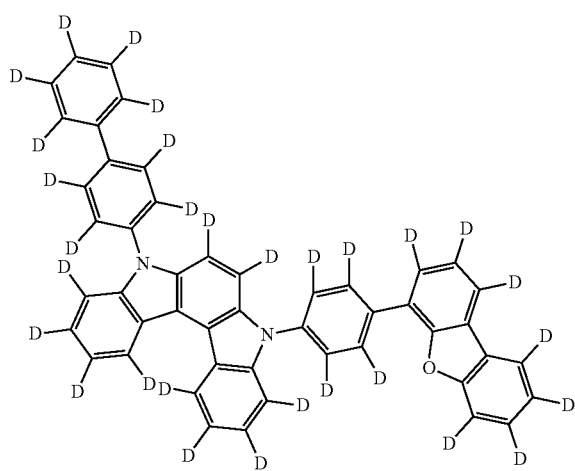

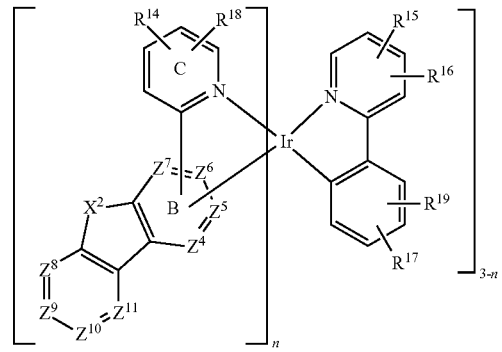

wherein, in Chemical Formula 4, $Z^4$ to $Z^{11}$ are independently N, C or $CR^c$, the ring C is bound to the ring B through a C—C bond, iridium is bound to the ring B through a Ir—C bond, $X^2$ is O or S, $R^c$ and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted $C_3$ to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is an integer ranging from 1 to 3.

2. The organic optoelectronic device of claim 1, wherein Chemical Formula 4 is represented by one of Chemical Formula 4-1 to Chemical Formula 4-6:

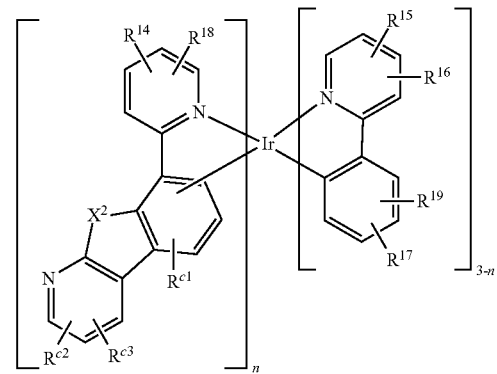

[Chemical Formula 4-2]

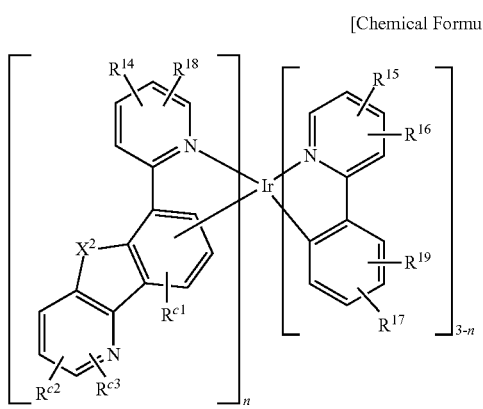

[Chemical Formula 4-5]

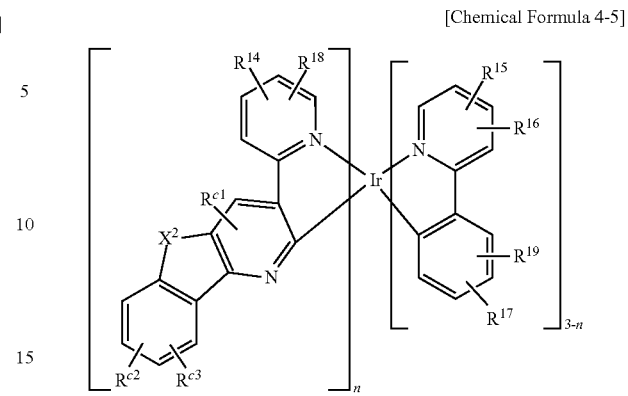

[Chemical Formula 4-3]

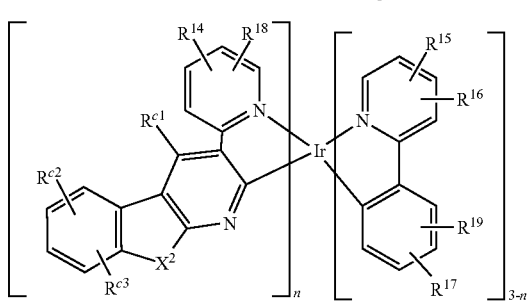

[Chemical Formula 4-6]

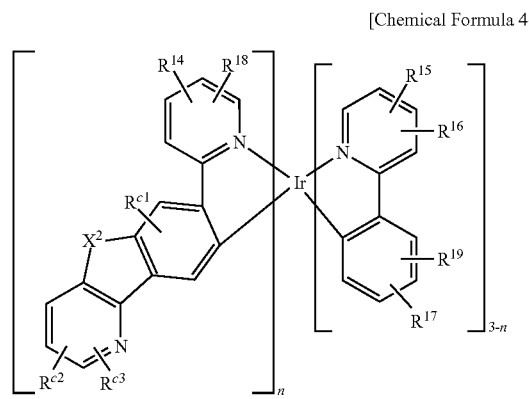

[Chemical Formula 4-4]

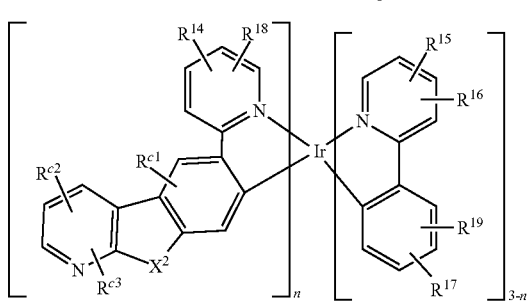

wherein, in Chemical Formula 4-1 to Chemical Formula 4-6, $X^2$ is O or S, $R^{c1}$, $R^{c2}$, $R^{c3}$, and $R^{14}$ to $R^{19}$ are independently hydrogen, deuterium, a halogen, germanium group, a cyano group, a substituted or unsubstituted silyl group, a substituted or unsubstituted C1 to C10 alkyl group, a substituted or unsubstituted C3 to C20 cycloalkyl group, a substituted or unsubstituted C1 to C10 alkylsilyl group, a substituted or unsubstituted C6 to C20 aryl group, or a substituted or unsubstituted C2 to C30 heterocyclic group, and n is an integer ranging from 1 to 3.

3. The organic optoelectronic device of claim 1, wherein Chemical Formula 4 is represented by Chemical Formula 4-1:

[Chemical Formula 4-1]

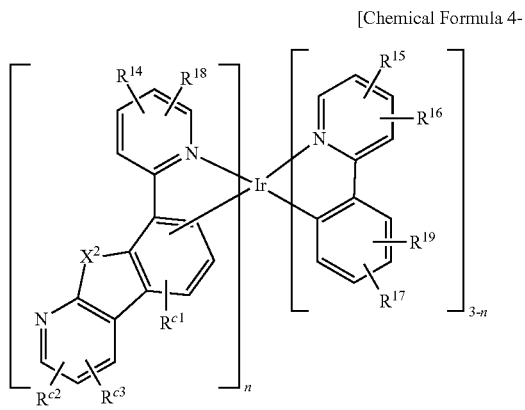

wherein, in Chemical Formula 4-1, $X^2$ is O or S, $R^{c1}$, $R^{c2}$, $R^{c3}$, and $R^{14}$ to $R^{19}$ are independently hydrogen, deuterium, a halogen, a substituted or unsubstituted silyl group, a substituted or unsubstituted C1 to C10 alkyl group, a substituted or unsubstituted C1 to C10 alkylsilyl group, or a substituted or unsubstituted C6 to C20 aryl group, n is an integer ranging from 1 to 3, "substituted" refers to replacement of at least one hydrogen of a substituent or a compound by deuterium, a halogen, a C1 to C4 alkyl group, or a C6 to C12 aryl group.

4. A display device comprising the organic optoelectronic device according to claim 1.

* * * * *